(12) United States Patent
Frank et al.

(10) Patent No.: US 11,986,273 B2
(45) Date of Patent: *May 21, 2024

(54) DETECTING ALCOHOL INTOXICATION FROM VIDEO IMAGES

(71) Applicant: Facense Ltd., Kiryat Tivon (IL)

(72) Inventors: Ari M Frank, Haifa (IL); Arie Tzvieli, Berkeley, CA (US); Ori Tzvieli, Berkeley, CA (US); Gil Thieberger, Kiryat Tivon (IL)

(73) Assignee: Facense Ltd., Kiryat Tivon (IL)

(*) Notice: Subject to any disclaimer, the term of this patent is extended or adjusted under 35 U.S.C. 154(b) by 0 days.

This patent is subject to a terminal disclaimer.

(21) Appl. No.: 17/381,222

(22) Filed: Jul. 21, 2021

(65) Prior Publication Data
US 2021/0345888 A1 Nov. 11, 2021

Related U.S. Application Data

(63) Continuation of application No. 17/005,259, filed on Aug. 27, 2020, now Pat. No. 11,103,139, which is a
(Continued)

(51) Int. Cl.
*G01J 5/00* (2022.01)
*A61B 5/00* (2006.01)
(Continued)

(52) U.S. Cl.
CPC ............ *A61B 5/015* (2013.01); *A61B 5/0075* (2013.01); *A61B 5/165* (2013.01); *A61B 5/6803* (2013.01);
(Continued)

(58) Field of Classification Search
CPC ........ G16H 50/20; G16H 50/30; G16H 10/60; A61B 90/361; A61B 5/02438;
(Continued)

(56) References Cited

U.S. PATENT DOCUMENTS 5,152,979 A * 10/1992 Hunter .................. A61K 31/77
514/723
5,757,002 A 5/1998 Yamasaki et al.
(Continued)

OTHER PUBLICATIONS

U.S. Appl. No. 10/152,869, filed Dec. 11, 2018, Peyrard.
(Continued)

*Primary Examiner* — Gail Kaplan Verbitsky
(74) *Attorney, Agent, or Firm* — Active Knowledge Ltd.

(57) ABSTRACT

Described herein are embodiments of systems and methods that utilize images of a user's face to detect alcohol intoxication. One embodiment of a system to detect alcohol intoxication includes first and second inward-facing head-mounted cameras that are located less than 5 cm from a user's face, are sensitive to wavelengths below 1050 nanometer, and are configured to capture images of respective first and second regions on the user's face. The system also includes a computer that calculates, based on baseline images captured with the cameras while the user was not intoxicated, a baseline pattern of hemoglobin concentrations at regions on the face. The computer also calculates, based on a current set of images captured with the cameras, a current pattern of hemoglobin concentrations at the regions, and detects whether the user is intoxicated based on a deviation of the current pattern from the baseline pattern.

20 Claims, 11 Drawing Sheets

Related U.S. Application Data continuation-in-part of application No. 16/854,883, filed on Apr. 21, 2020, now Pat. No. 10,813,559, and a continuation-in-part of application No. 16/689,929, filed on Nov. 20, 2019, now Pat. No. 11,064,892, and a continuation-in-part of application No. 16/689,959, filed on Nov. 20, 2019, now Pat. No. 10,799,122, said application No. 16/854,883 is a continuation-in-part of application No. 16/453,993, filed on Jun. 26, 2019, now Pat. No. 10,667,697, said application No. 17/005,259 is a continuation-in-part of application No. 16/831,413, filed on Mar. 26, 2020, now Pat. No. 10,791,938, which is a continuation-in-part of application No. 16/551,654, filed on Aug. 26, 2019, now Pat. No. 10,638,938, which is a continuation-in-part of application No. 16/453,993, filed on Jun. 26, 2019, now Pat. No. 10,667,697, which is a continuation-in-part of application No. 16/375,841, filed on Apr. 4, 2019, now Pat. No. 10,376,163, which is a continuation-in-part of application No. 16/156,493, filed on Oct. 10, 2018, now Pat. No. 10,524,667, which is a continuation-in-part of application No. 15/635,178, filed on Jun. 27, 2017, now Pat. No. 10,136,856, said application No. 16/156,493 is a continuation-in-part of application No. 15/231,276, filed on Aug. 8, 2016, now abandoned, and a continuation-in-part of application No. 15/832,855, filed on Dec. 6, 2017, now Pat. No. 10,130,308, which is a continuation-in-part of application No. 15/182,592, filed on Jun. 14, 2016, now Pat. No. 10,165,949, and a continuation-in-part of application No. 15/231,276, filed on Aug. 8, 2016, now abandoned, and a continuation-in-part of application No. 15/284,528, filed on Oct. 3, 2016, now Pat. No. 10,113,913, and a continuation-in-part of application No. 15/635,178, filed on Jun. 27, 2017, now Pat. No. 10,136,856, and a continuation-in-part of application No. 15/722,434, filed on Oct. 2, 2017, now Pat. No. 10,523,852, and a continuation-in-part of application No. 15/182,566, filed on Jun. 14, 2016, now Pat. No. 9,867,546, said application No. 16/156,493 is a continuation-in-part of application No. 15/833,115, filed on Dec. 6, 2017, now Pat. No. 10,130,261, which is a continuation-in-part of application No. 15/182,592, filed on Jun. 14, 2016, now Pat. No. 10,165,949, and a continuation-in-part of application No. 15/231,276, filed on Aug. 8, 2016, now abandoned, and a continuation-in-part of application No. 15/284,528, filed on Oct. 3, 2016, now Pat. No. 10,113,913, and a continuation-in-part of application No. 15/635,178, filed on Jun. 27, 2017, now Pat. No. 10,136,856, and a continuation-in-part of application No. 15/722,434, filed on Oct. 2, 2017, now Pat. No. 10,523,852, said application No. 16/453,993 is a continuation-in-part of application No. 16/147,695, filed on Sep. 29, 2018, now Pat. No. 10,376,153, which is a continuation of application No. 15/182,592, filed on Jun. 14, 2016, now Pat. No. 10,165,949, said application No. 16/689,929 is a continuation-in-part of application No. 16/156,586, filed on Oct. 10, 2018, now Pat. No. 10,524,696, which is a continuation-in-part of application No. 15/832,815, filed on Dec. 6, 2017, now Pat. No. 10,136,852, and a continuation-in-part of application No. 15/859,772, filed on Jan. 2, 2018, now Pat. No. 10,159,411.

(60) Provisional application No. 63/048,638, filed on Jul. 6, 2020, provisional application No. 63/024,471, filed on May 13, 2020, provisional application No. 63/006,827, filed on Apr. 8, 2020, provisional application No. 62/960,913, filed on Jan. 14, 2020, provisional application No. 62/945,141, filed on Dec. 7, 2019, provisional application No. 62/928,726, filed on Oct. 31, 2019, provisional application No. 62/722,655, filed on Aug. 24, 2018, provisional application No. 62/354,833, filed on Jun. 27, 2016, provisional application No. 62/372,063, filed on Aug. 8, 2016, provisional application No. 62/652,348, filed on Apr. 4, 2018, provisional application No. 62/667,453, filed on May 5, 2018, provisional application No. 62/202,808, filed on Aug. 8, 2015, provisional application No. 62/236,868, filed on Oct. 3, 2015, provisional application No. 62/456,105, filed on Feb. 7, 2017, provisional application No. 62/480,496, filed on Apr. 2, 2017, provisional application No. 62/566,572, filed on Oct. 2, 2017, provisional application No. 62/175,319, filed on Jun. 14, 2015.

(51) Int. Cl.
  *A61B 5/01* (2006.01)
  *A61B 5/16* (2006.01)
  *G01J 5/02* (2022.01)
  *G01J 5/12* (2006.01)
  *A61B 5/145* (2006.01)
  *G01J 5/48* (2022.01)

(52) U.S. Cl.
  CPC .......... *A61B 5/6814* (2013.01); *A61B 5/7282* (2013.01); *A61B 5/748* (2013.01); *G01J 5/0265* (2013.01); *G01J 5/12* (2013.01); *A61B 5/0077* (2013.01); *A61B 5/14535* (2013.01); *A61B 2562/0271* (2013.01); *A61B 2562/0276* (2013.01); *A61B 2576/00* (2013.01); *G01J 2005/0077* (2013.01); *G01J 5/485* (2022.01)

(58) Field of Classification Search
  CPC .............. A61B 5/0245; A61B 5/14542; A61B 5/02405; A61B 5/333; A61B 5/015; A61B 5/0075; A61B 5/165; A61B 5/6814; A61B 5/7282; A61B 5/748; A61B 5/0077; A61B 5/14535; A61B 2562/0271; A61B 2562/0276; A61B 2576/00; A61M 2230/50; G01N 2021/6419; G01N 2021/6493; G01N 2033/4975; G01N 21/6458; G01N 21/6486; G01N 33/0036; G01N 33/497; G01N 33/50; G01N 33/5097; G01J 2005/0077; G01J 5/025; G01J 5/00; G01J 5/12
  See application file for complete search history.

(56) References Cited

U.S. PATENT DOCUMENTS

| | | |
|---|---|---|
| 6,819,950 B2 | 11/2004 | Mills |
| 7,384,395 B2 | 6/2008 | Hatlestsad et al. |
| 8,175,670 B2 | 5/2012 | Baker, Jr. et al. |
| 8,251,903 B2 | 8/2012 | LeBoeuf et al. |
| 8,512,253 B2 | 8/2013 | Reichman et al. |
| 8,617,081 B2 | 12/2013 | Mestha et al. |
| 8,768,424 B2 | 7/2014 | Crowe et al. |
| 8,768,438 B2 | 7/2014 | Mestha et al. |
| 8,855,384 B2 | 10/2014 | Kyal et al. |
| 8,977,347 B2 | 3/2015 | Mestha et al. |
| 9,020,185 B2 | 4/2015 | Mestha et al. |
| 9,044,180 B2 | 6/2015 | LeBoeuf et al. |
| 9,220,856 B2 | 12/2015 | Martin et al. |

(56) References Cited

U.S. PATENT DOCUMENTS

| | | |
|---|---|---|
| 9,414,769 B2 | 8/2016 | Karst et al. |
| 9,489,817 B2 | 11/2016 | Gui |
| 9,610,035 B2 | 4/2017 | Aarts et al. |
| 9,805,475 B2 | 10/2017 | Rubinstein et al. |
| 9,808,204 B2 | 11/2017 | LeBoeuf et al. |
| 9,848,780 B1 | 12/2017 | DeBusschere et al. |
| 9,940,710 B2 | 4/2018 | Watanabe |
| 9,980,650 B2 | 5/2018 | Bezemer |
| 2007/0276632 A1 | 11/2007 | Banet et al. |
| 2010/0241011 A1 | 9/2010 | McCombie et al. |
| 2012/0022349 A1 | 1/2012 | Poupko et al. |
| 2012/0029320 A1 | 2/2012 | Watson et al. |
| 2013/0215244 A1 | 8/2013 | Mestha et al. |
| 2014/0213917 A1 | 7/2014 | Hobeika et al. |
| 2015/0005646 A1 | 1/2015 | Balakrishnan et al. |
| 2015/0112606 A1 | 4/2015 | He et al. |
| 2015/0297126 A1 | 10/2015 | Atsumori et al. |
| 2016/0007935 A1 | 1/2016 | Hernandez et al. |
| 2016/0022157 A1 | 1/2016 | Melker et al. |
| 2016/0070122 A1 | 3/2016 | Sales et al. |
| 2016/0098592 A1 | 4/2016 | Lee et al. |
| 2016/0120411 A1 | 5/2016 | Hadley et al. |
| 2016/0167672 A1 | 6/2016 | Krueger |
| 2016/0206216 A1 | 7/2016 | Kirenko |
| 2016/0296124 A1 | 10/2016 | Wegerich et al. |
| 2016/0302677 A1 | 10/2016 | He |
| 2017/0007167 A1 | 1/2017 | Kostic et al. |
| 2017/0011210 A1 | 1/2017 | Cheong et al. |
| 2017/0112376 A1 | 4/2017 | Gill et al. |
| 2017/0202505 A1 | 7/2017 | Kirenko et al. |
| 2017/0367590 A1 | 12/2017 | Sebe et al. |
| 2018/0031372 A1 | 2/2018 | Gill |
| 2018/0042486 A1 | 2/2018 | Yoshizawa et al. |
| 2018/0146870 A1 | 5/2018 | Shemesh et al. |
| 2018/0177416 A1 | 6/2018 | Church et al. |
| 2018/0192950 A1 | 7/2018 | LeBoeuf et al. |
| 2018/0199870 A1 | 7/2018 | Lee et al. |
| 2018/0206733 A1 | 7/2018 | Kasan et al. |
| 2018/0206735 A1 | 7/2018 | Holz et al. |
| 2018/0210547 A1 | 7/2018 | Sarkar |
| 2018/0214079 A1 | 8/2018 | Banet et al. |
| 2018/0314879 A1 | 11/2018 | Khwaja et al. |
| 2019/0021615 A1 | 1/2019 | Rundo et al. |
| 2019/0117096 A1 | 4/2019 | Rundo et al. |
| 2019/0159735 A1 | 5/2019 | Rundo et al. |
| 2019/0174039 A1 | 6/2019 | Jung et al. |
| 2019/0196179 A1 | 6/2019 | Sarkar et al. |
| 2019/0204912 A1 | 7/2019 | Yang et al. |
| 2019/0216340 A1 | 7/2019 | Holz et al. |
| 2019/0313914 A1 | 10/2019 | Kirenko et al. |
| 2020/0156648 A1 | 5/2020 | Zhang et al. |
| 2020/0397306 A1* | 12/2020 | Frank ................ G01J 5/10 |

OTHER PUBLICATIONS

U.S. Appl. No. 10/216,981, filed Feb. 26, 2019, Tzvieli et al.
U.S. Appl. No. 10/317,672, filed Jun. 11, 2019, Sarkar.
U.S. Appl. No. 10/349,887, filed Jul. 16, 2019, Tzvieli et al.
U.S. Appl. No. 10/376,163, filed Aug. 13, 2019, Tzvieli et al.
U.S. Appl. No. 10/506,960, filed Dec. 17, 2019, Kaestle.
U.S. Appl. No. 10/638,938, filed May 5, 2020, Tzvieli et al.
U.S. Appl. No. 10/791,938, filed Oct. 6, 2020, Tzvieli et al.
U.S. Appl. No. 10/799,122, filed Oct. 13, 2020, Tzvieli et al.

* cited by examiner

DETECTING ALCOHOL INTOXICATION FROM VIDEO IMAGES

CROSS-REFERENCE TO RELATED APPLICATIONS

This application is a Continuation of U.S. application Ser. No. 17/005,259, filed Aug. 27, 2020.

U.S. application Ser. No. 17/005,259 claims priority to U.S. Provisional Patent Application No. 62/928,726, filed Oct. 31, 2019, U.S. Provisional Patent Application No. 62/945,141, filed Dec. 7, 2019, U.S. Provisional Patent Application No. 62/960,913, filed Jan. 14, 2020, U.S. Provisional Patent Application No. 63/006,827, filed Apr. 8, 2020, U.S. Provisional Patent Application No. 63/024,471, filed May 13, 2020, and U.S. Provisional Patent Application No. 63/048,638, filed Jul. 6, 2020.

U.S. application Ser. No. 17/005,259 is a Continuation-In-Part of U.S. application Ser. No. 16/689,959, filed Nov. 20, 2019, which claims priority to U.S. Provisional Patent Application No. 62/874,430, filed Jul. 15, 2019.

U.S. application Ser. No. 17/005,259 is also a Continuation-In-Part of U.S. application Ser. No. 16/854,883, filed Apr. 21, 2020, which is a Continuation-In-Part of U.S. application Ser. No. 16/453,993, filed Jun. 26, 2019, now U.S. Pat. No. 10,667,697.

U.S. Ser. No. 17/005,259 is also a Continuation-In-Part of U.S. application Ser. No. 16/831,413, filed Mar. 26, 2020, which is a Continuation-In-Part of U.S. application Ser. No. 16/551,654, filed Aug. 26, 2019, now U.S. Pat. No. 10,638,938. U.S. Ser. No. 16/551,654 is a Continuation-In-Part of U.S. application Ser. No. 16/453,993, filed Jun. 26, 2019. U.S. Ser. No. 16/453,993 is a Continuation-In-Part of U.S. application Ser. No. 16/375,841, filed Apr. 4, 2019. U.S. Ser. No. 16/375,841 is a Continuation-In-Part of U.S. application Ser. No. 16/156,493, now U.S. Pat. No. 10,524,667, filed Oct. 10, 2018. U.S. Ser. No. 16/156,493, is a Continuation-In-Part of U.S. application Ser. No. 15/635,178, filed Jun. 27, 2017, now U.S. Pat. No. 10,136,856, which claims priority to U.S. Provisional Patent Application No. 62/354,833, filed Jun. 27, 2016, and U.S. Provisional Patent Application No. 62/372,063, filed Aug. 8, 2016.

U.S. Ser. No. 16/156,493 is also a Continuation-In-Part of U.S. application Ser. No. 15/231,276, filed Aug. 8, 2016, which claims priority to U.S. Provisional Patent Application No. 62/202,808, filed Aug. 8, 2015, and U.S. Provisional Patent Application No. 62/236,868, filed Oct. 3, 2015.

U.S. Ser. No. 16/156,493 is also a Continuation-In-Part of U.S. application Ser. No. 15/832,855, filed Dec. 6, 2017, now U.S. Pat. No. 10,130,308, which claims priority to U.S. Provisional Patent Application No. 62/456,105, filed Feb. 7, 2017, and U.S. Provisional Patent Application No. 62/480,496, filed Apr. 2, 2017, and U.S. Provisional Patent Application No. 62/566,572, filed Oct. 2, 2017. U.S. Ser. No. 15/832,855 is a Continuation-In-Part of U.S. application Ser. No. 15/182,592, filed Jun. 14, 2016, now U.S. Pat. No. 10,165,949, a Continuation-In-Part of U.S. application Ser. No. 15/231,276, filed Aug. 8, 2016, a Continuation-In-Part of U.S. application Ser. No. 15/284,528, filed Oct. 3, 2016, now U.S. Pat. No. 10,113,913, a Continuation-In-Part of U.S. application Ser. No. 15/635,178, filed Jun. 27, 2017, now U.S. Pat. No. 10,136,856, and a Continuation-In-Part of U.S. application Ser. No. 15/722,434, filed Oct. 2, 2017.

U.S. Ser. No. 15/832,855 is a Continuation-In-Part of U.S. application Ser. No. 15/182,566, filed Jun. 14, 2016, now U.S. Pat. No. 9,867,546, which claims priority to U.S. Provisional Patent Application No. 62/175,319, filed Jun. 14, 2015, and U.S. Provisional Patent Application No. 62/202,808, filed Aug. 8, 2015.

U.S. Ser. No. 15/182,592 claims priority to U.S. Provisional Patent Application No. 62/175,319, filed Jun. 14, 2015, and U.S. Provisional Patent Application No. 62/202,808, filed Aug. 8, 2015.

U.S. Ser. No. 15/284,528 claims priority to U.S. Provisional Patent Application No. 62/236,868, filed Oct. 3, 2015, and U.S. Provisional Patent Application No. 62/354,833, filed Jun. 27, 2016, and U.S. Provisional Patent Application No. 62/372,063, filed Aug. 8, 2016.

U.S. Ser. No. 16/156,493 is also a Continuation-In-Part of U.S. application Ser. No. 15/833,115, filed Dec. 6, 2017, now U.S. Pat. No. 10,130,261. U.S. Ser. No. 15/833,115 is a Continuation-In-Part of U.S. application Ser. No. 15/182,592, a Continuation-In-Part of U.S. application Ser. No. 15/231,276, filed Aug. 8, 2016, a Continuation-In-Part of U.S. application Ser. No. 15/284,528, a Continuation-In-Part of U.S. application Ser. No. 15/635,178, and a Continuation-In-Part of U.S. application Ser. No. 15/722,434, filed Oct. 2, 2017.

U.S. Ser. No. 16/453,993 is also a Continuation-In-Part of U.S. application Ser. No. 16/147,695, filed Sep. 29, 2018. U.S. Ser. No. 16/147,695 is a Continuation of U.S. application Ser. No. 15/182,592, filed Jun. 14, 2016, which claims priority to U.S. Provisional Patent Application No. 62/175,319, filed Jun. 14, 2015, and U.S. Provisional Patent Application No. 62/202,808, filed Aug. 8, 2015.

U.S. application Ser. No. 17/005,259 is a Continuation-In-Part of U.S. Ser. No. 16/689,929, filed Nov. 20, 2019, that is a Continuation-In-Part of U.S. Ser. No. 16/156,586, filed Oct. 10, 2018, that is a Continuation-In-Part of U.S. application Ser. No. 15/832,815, filed Dec. 6, 2017, which claims priority to U.S. Provisional Patent Application No. 62/456,105, filed Feb. 7, 2017, and U.S. Provisional Patent Application No. 62/480,496, filed Apr. 2, 2017, and U.S. Provisional Patent Application No. 62/566,572, filed Oct. 2, 2017. U.S. Ser. No. 16/156,586 is also a Continuation-In-Part of U.S. application Ser. No. 15/859,772 Jan. 2, 2018, now U.S. Pat. No. 10,159,411.

BACKGROUND

Alcohol abuse in the workplace can be a serious issue for health, safety and work performance. Drinking alcohol alters a person's perception and can have a serious effect on the ability to perform a job correctly and safely. This can be a very dangerous in various situations, such as driving, operating machinery, and practically any profession in which mistakes can cause serious illness, injury or even death. Thus, there is a need for a relatively inexpensive and unobtrusive way to accurately detect whether a person is intoxicated, and preferably to do so without interrupting the person's activities.

SUMMARY

Described herein are embodiments of systems and methods that utilize images of a user's face in order to detect temperature changes on a user's face for various purposes such as detecting fever, estimating core body temperature, detecting intoxication, and additional applications. The images may be captured using different hardware setups. In some embodiments, the images are captured using one or more inward-facing head-mounted cameras (e.g., one or more cameras attached to, or embedded in, smartglasses frames).

In one embodiment, the system is able to detect whether the user is intoxicated, optionally without using a thermal camera. In another embodiment, the system is able to detect whether the user has a fever, and/or the user's core body temperature, without receiving a temperature reading of the skin area above the temporal artery.

Some of the embodiments described herein have one or more of the following advantages: there is no need to detect the region of skin above the temporal artery, the system may operate well without measuring the temperature of the region of skin above the temporal artery, and the images captured by the camera sensitive to wavelengths below 1050 nanometer may be indicative of extent of thermal interference from the environment.

Some aspects of this disclosure involve utilization of sensors that are physically coupled to smartglasses in order to conveniently, and optionally continuously, monitor users. Smartglasses are generally comfortable to wear, lightweight, and can have extended battery life. Thus, they are well suited as an instrument for long-term monitoring of patient's physiological signals and activity, in order to determine whether the user has a fever and/or whether the user is intoxicated.

One aspect of this disclosure involves a system configured to detect alcohol intoxication. In one embodiment, the system includes first and second inward-facing head-mounted cameras (denoted $Cam_{1\&2}$). $Cam_{1\&2}$ are located less than 5 cm from a user's face, are sensitive to wavelengths below 1050 nanometer, and are configured to capture images of respective first and second regions on the user's face. Optionally, the middles of the first and second regions are at least 4 cm apart. In one example, the first region is located above the user's eyes, and the second region is located below the user's eyes. In another example, the middle of the first region is located less than 4 cm from the vertical symmetric axis of the user's face, and the middle of the second region is located more than 4 cm from the vertical symmetric axis.

The system also includes a computer, which is configured to perform the following: calculate, based on baseline images captured with $Cam_{1\&2}$ while the user was sober, a baseline pattern comprising values indicative of first and second baseline hemoglobin concentrations at the first and second regions, respectively; calculate, based on a current set of images captured with $Cam_{1\&2}$, a current pattern comprising values indicative of first and second current hemoglobin concentrations at the first and second regions, respectively; and detect whether the user is intoxicated based on a deviation of the current pattern from the baseline pattern. Optionally, the computer calculates the values indicative of the baseline and current hemoglobin concentrations based on detecting imaging photoplethysmogram signals in the baseline and the current set of images.

In one embodiment, the computer also calculates, based on additional baseline images captured with $Cam_{1\&2}$ while the user was intoxicated, an intoxication-baseline pattern comprising values indicative of first and second fever hemoglobin concentrations at the first and second regions, respectively. In this embodiment, the computer bases the detection of whether the user is intoxicated also on a deviation of the current pattern from the intoxication-baseline pattern.

In one embodiment, the baseline images and the current set of images comprise a first channel corresponding to wavelengths that are mostly below 580 nanometers and a second channel corresponding to wavelengths mostly above 580 nanometers; the baseline pattern comprises: (i) first values, derived based on the first channel in the baseline images, which are indicative of the first and second baseline hemoglobin concentrations at the first and second regions, respectively, and (ii) second values, derived based on the second channel in the baseline images, which are indicative of third and fourth baseline hemoglobin concentrations at the first and second regions, respectively. The current pattern comprises: (i) third values, derived based on the first channel in the current set of images, which are indicative of the first and second current hemoglobin concentrations at the first and second regions, respectively, and (ii) fourth values, derived based on the second channel in the current set of images, which are indicative of third and fourth current hemoglobin concentrations at the first and second regions, respectively. Optionally, having separate values for different wavelengths enables to account for interference from the environment when detecting whether the user has the fever because temperature interference from the environment is expected to affect the third values more than the fourth values. Optionally, the computer calculates a confidence in a detection of intoxication based on the deviation of the current pattern from the baseline pattern, such that the confidence decreases as the difference between the third values and the fourth values increases.

In some embodiments, the computer may detect additional physiological signals or conditions based on the deviation of the current pattern from the baseline pattern. In one example, the computer detects blushing based on the deviation of the current pattern from the baseline pattern, and presents an alert to the user about the blushing. In another embodiment, the computer utilizes one or more calibration measurements of the user's core body temperature, taken by a different device, prior to a certain time, to calculate the user's core body temperature based on a certain set of images that were taken by $Cam_{1\&2}$ after the certain time.

Another aspect of this disclosure includes a method for detecting alcohol intoxication, which includes the following steps: In Step 1, receiving, from first and second inward-facing head-mounted cameras ($Cam_{1\&2}$) sensitive to wavelengths below 1050 nanometer, images of respective first and second regions on a user's face. Optionally, the middles of the first and second regions are at least 4 cm apart. In Step 2, calculating, based on baseline images captured with $Cam_{1\&2}$ while the user was sober, a baseline pattern comprising values indicative of first and second baseline hemoglobin concentrations at the first and second regions, respectively. In Step 3, calculating, based on a current set of images captured with $Cam_{1\&2}$, a current pattern comprising values indicative of first and second current hemoglobin concentrations at the first and second regions, respectively. And in Step 4, detecting whether the user is intoxicated based on a deviation of the current pattern from the baseline pattern.

In one embodiment, the method for detecting fever optionally includes the following steps: calculating, based on additional baseline images captured with $Cam_{1\&2}$ while the user had a fever, a fever-baseline pattern comprising values indicative of first and second fever hemoglobin concentrations at the first and second regions, respectively; and basing the detecting of whether the user is intoxicated also on a deviation of the current pattern from the fever-baseline pattern.

BRIEF DESCRIPTION OF THE DRAWINGS

The embodiments are herein described by way of example only, with reference to the following drawings.

DETAILED DESCRIPTION

Figure 1A:
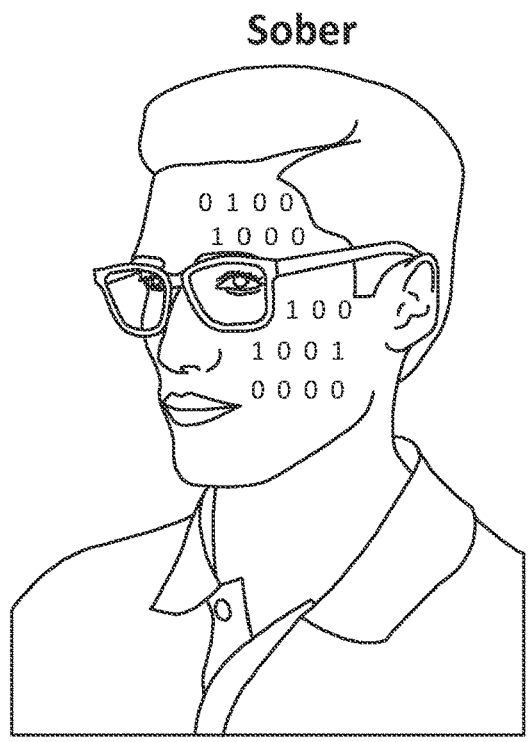
FIG. 1a illustrates an example of a hemoglobin concentration pattern of a sober person.

Herein the terms "photoplethysmogram signal", "photoplethysmographic signal", "photoplethysmography signal", and other similar variations are interchangeable and refer to the same type of signal. A photoplethysmogram signal may be referred to as a "PPG signal", or an "iPPG signal" when specifically referring to a PPG signal obtained from a camera. The terms "photoplethysmography device", "photoplethysmographic device", "photoplethysmogram device", and other similar variations are also interchangeable and refer to the same type of device that measures a signal from which it is possible to extract the photoplethysmogram signal. The photoplethysmography device may be referred to as "PPG device".

Sentences in the form of "a sensor configured to measure a signal indicative of a photoplethysmogram signal" refer to at least one of: (i) a contact PPG device, such as a pulse oximeter that illuminates the skin and measures changes in light absorption, where the changes in light absorption are indicative of the PPG signal, and (ii) a non-contact camera that captures images of the skin, where a computer extracts the PPG signal from the images using an imaging photoplethysmography (iPPG) technique. Other names known in the art for iPPG include: remote photoplethysmography (rPPG), remote photoplethysmographic imaging, remote imaging photoplethysmography, remote-PPG, and multi-site photoplethysmography (MPPG).

A PPG signal is often obtained by using a pulse oximeter, which illuminates the skin and measures changes in light absorption. Another possibility for obtaining the PPG signal is using an imaging photoplethysmography (iPPG) device. As opposed to contact PPG devices, iPPG does not require contact with the skin and is obtained by a non-contact sensor, such as a video camera.

A time series of values measured by a PPG device, which is indicative of blood flow changes due to pulse waves, is typically referred to as a waveform (or PPG waveform to indicate it is obtained with a PPG device). It is well known that PPG waveforms show significant gender-related differences, age-related differences, and health-related differences. As a result, the PPG waveforms of different people often display different characteristics (e.g., slightly different shapes and/or amplitudes). In addition, the PPG waveform depends on the site at which it is measured, skin temperature, skin tone, and other parameters.

The analysis of PPG signals usually includes the following steps: filtration of a PPG signal (such as applying bandpass filtering and/or heuristic filtering), extraction of feature values from fiducial points in the PPG signal (and in some cases may also include extraction of feature values from non-fiducial points in the PPG signal), and analysis of the feature values.

One type of features that is often used when performing calculations involving PPG signals involves fiducial points related to the waveforms of the PPG signal and/or to functions thereof (such as various derivatives of the PPG signal). There are many known techniques to identify the fiducial points in the PPG signal, and to extract the feature values. The following are some non-limiting examples of how to identify fiducial points.

Figure 2A:
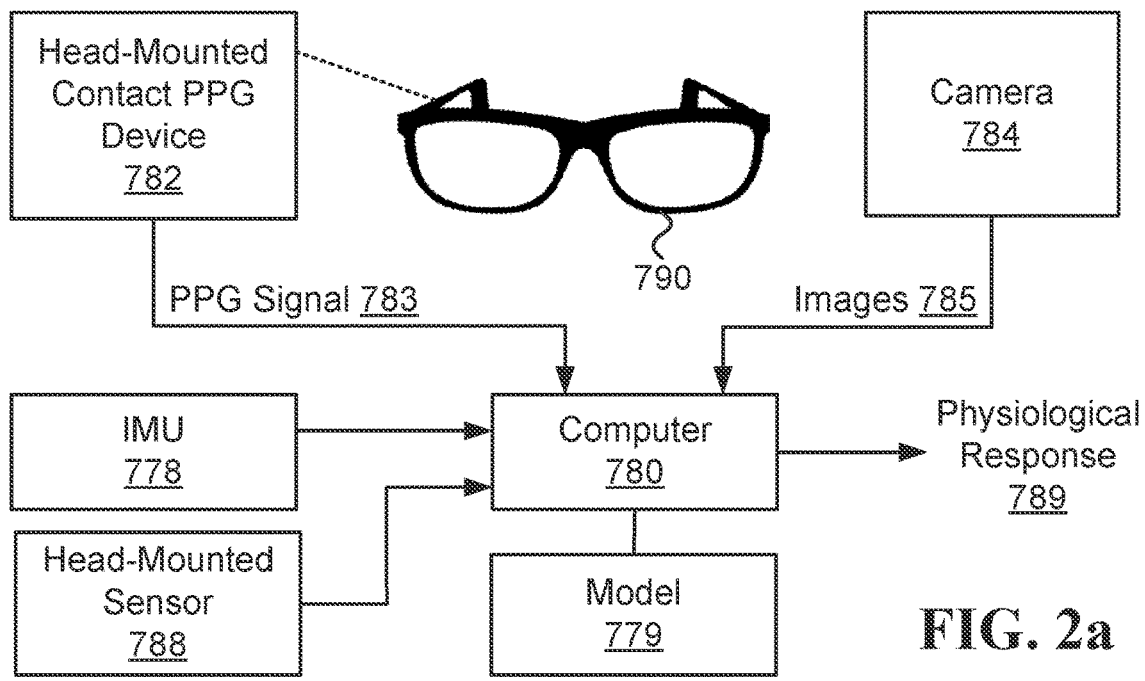
FIG. 2a illustrates an embodiment of a system that utilizes multiple PPG signals, measured using different types of sensors, to detect a physiological response.
Figure 2B:
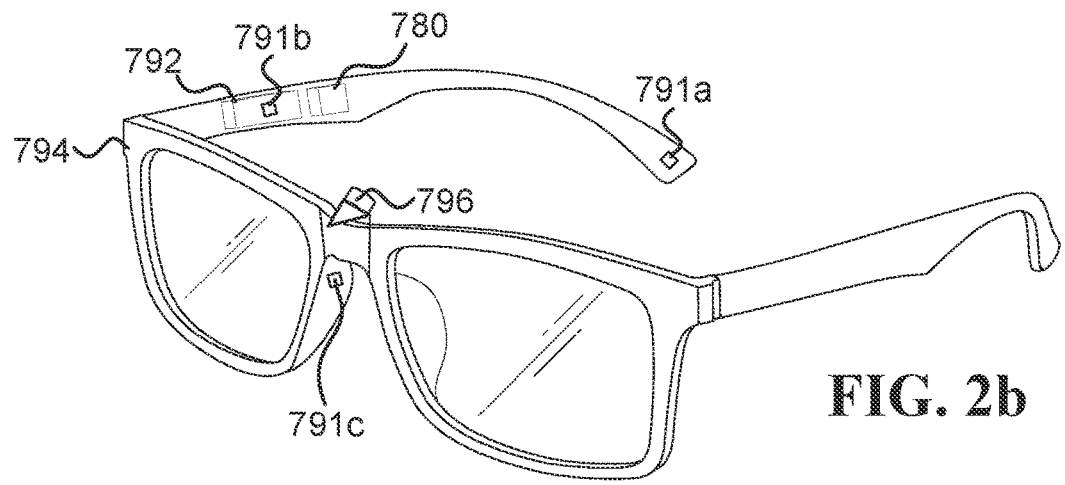
FIG. 2b illustrates smartglasses that include a camera and several contact PPG devices.
Figure 2C:
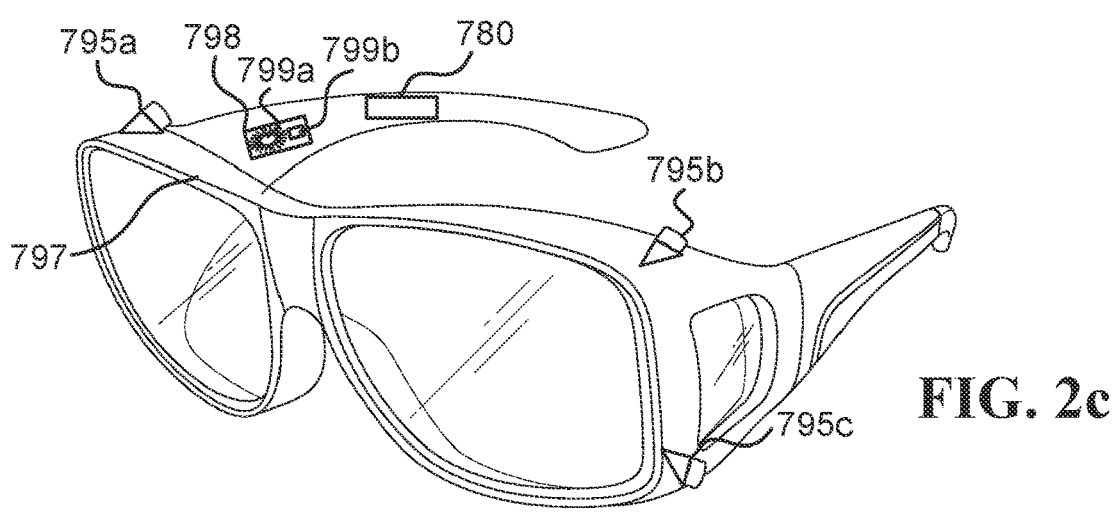
FIG. 2c illustrates smartglasses that include at least first, second, and third inward-facing cameras.
Figure 2D:
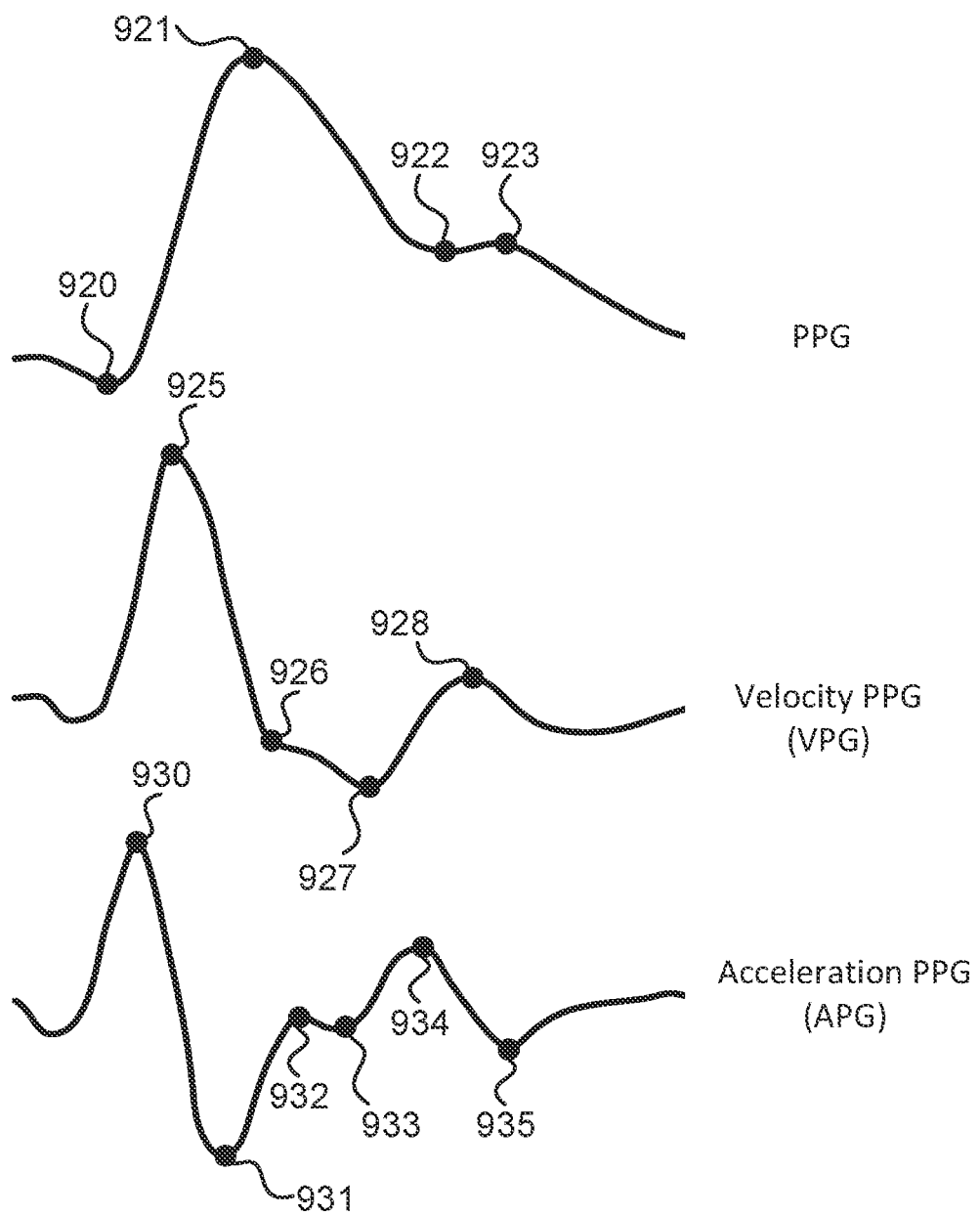
FIG. 2d is a schematic illustration of some of the various fiducial points for PPG signals often used in the art.

FIG. 2d is a schematic illustration of some of the various fiducial points often used in the art (and described below). These examples of fiducial points include fiducial points of the PPG signal, fiducial points in the first derivative of the PPG signal (velocity photoplethysmogram, VPG), and fiducial points in the second derivative of the PPG signal (acceleration photoplethysmogram, APG).

Fiducial points in the PPG signal may include: the systolic notch 920, which is the minimum at the PPG signal onset; the systolic peak 921, which is the maximum of the PPG signal; the dicrotic notch 922, which coincident with e 934 (see below at the second derivative of the PPG signal); and the diastolic peak 923, which is the first local maximum of the PPG signal after the dicrotic notch and before 0.8 of the duration of the cardiac cycle, or if there is no such local maximum, then the first local maximum of the second derivative after e and before 0.8 of the duration of the cardiac cycle.

Fiducial points in the first derivative of the PPG signal (velocity photoplethysmogram, VPG) may include: the maximum slope peak in systolic of VPG 925; the local minima slope in systolic of VPG 926; the global minima slope in systolic of VPG 927; and the maximum slope peak in diastolic of VPG 928.

Fiducial points in the second derivative of the PPG signal (acceleration photoplethysmogram, APG) may include: a 930, which is the maximum of APG prior to the maximum of VPG; b 931, which is the first local minimum of APG following a; c 932, which is the greatest maximum of APG between b and e, or if no maxima then the first of (i) the first maximum of VPG after e, and (ii) the first minimum of APG after e; d 933, which is the lowest minimum of APG after c and before e, or if no minima then coincident with c; e 934, which is the second maximum of APG after maximum of VPG and before 0.6 of the duration of the cardiac cycle, unless the c wave is an inflection point, in which case take the first maximum; and f 935, which is the first local minimum of APG after e and before 0.8 of the duration of the cardiac cycle.

Fiducial points in the third derivative of the PPG signal (PPG''') may include: the first local maximum of PPG''' after b; and the last local minimum of PPG''' before d, unless c=d, in which case take the first local minimum of PPG''' after d, and if there is a local maximum of the PPG signal between this point and the dicrotic notch then use it instead.

Feature values of the PPG signal may also be extracted from relationships in the PPG signal and/or its derivatives. The following are some non-limiting examples such possible feature values: pulse width, peak to peak time, ratio of areas before and after dicrotic notch in a complete cycle, baseline wander (BW), which is the mean of the amplitudes of a beat's peak and trough; amplitude modulation (AM), which is the difference between the amplitudes of each beat's peak and trough; and frequency modulation (FM), which is the time interval between consecutive peaks.

Examples of additional features that can be extracted from the PPG signal, together with schematic illustrations of the feature locations on the PPG signal, can be found in the following three publications: (i) Peltokangas, Mikko, et al. "Parameters extracted from arterial pulse waves as markers of atherosclerotic changes: performance and repeatability." IEEE journal of biomedical and health informatics 22.3 (2017): 750-757; (ii) Ahn, Jae Mok. "New aging index using signal features of both photoplethysmograms and acceleration plethysmograms." Healthcare informatics research 23.1 (2017): 53-59; (iii) Charlton, Peter H., et al. "Assessing mental stress from the photoplethysmogram: a numerical study." Physiological measurement 39.5 (2018): 054001, and (iv) Peralta, Elena, et al. "Optimal fiducial points for pulse rate variability analysis from forehead and finger photoplethysmographic signals." Physiological measurement 40.2 (2019): 025007.

Although the above mentioned references describe manual feature selection, the features may be selected using any appropriate feature engineering technique, including using automated feature engineering tools that help data scientists to reduce data exploration time, and enable non-experts, who may not be familiar with data science and/or PPG characteristics, to quickly extract value from their data with little effort.

Unless there is a specific reference to a specific derivative of the PPG signal, phrases of the form of "based on the PPG signal" refer to the PPG signal and any derivative thereof, including the first derivative of the PPG signal, the second derivative of the PPG signal, and the third derivative of the PPG signal. For example, a sentence in the form of "a computer configured to detect a physiological signal based on the PPG signal" is to be interpreted as "a computer configured to detect a physiological signal based on at least one of: the PPG signal, a first derivative of the PPG signal, a second derivative of the PPG signal, a the third derivative of the PPG signal, and/or any other derivative of the PPG signal".

Algorithms for filtration of the PPG signal, extraction of feature values from fiducial points in the PPG signal, and analysis of the feature values extracted from the PPG signal are well known in the art, and can be found for example in the following references: (i) Allen, John. "Photoplethysmography and its application in clinical physiological measurement." Physiological measurement 28.3 (2007): R1, and also in the thousands of references citing this reference; (ii) Elgendi, Mohamed. "On the analysis of fingertip photoplethysmogram signals." Current cardiology reviews 8.1 (2012): 14-25, and also in the hundreds of references citing this reference; (iii) Holton, Benjamin D., et al. "Signal recovery in imaging photoplethysmography." Physiological measurement 34.11 (2013): 1499, and also in the dozens of references citing this reference, (iv) Sun, Yu, and Nitish Thakor. "Photoplethysmography revisited: from contact to noncontact, from point to imaging." IEEE Transactions on Biomedical Engineering 63.3 (2015): 463-477, and also in the dozens of references citing this reference, (v) Kumar, Mayank, Ashok Veeraraghavan, and Ashutosh Sabharwal. "DistancePPG: Robust non-contact vital signs monitoring using a camera." Biomedical optics express 6.5 (2015): 1565-1588, and also in the dozens of references citing this reference, (vi) Wang, Wenjin, et al. "Algorithmic principles of remote PPG." IEEE Transactions on Biomedical Engineering 64.7 (2016): 1479-1491, and also in the dozens of references citing this reference, and (vii) Rouast, Philipp V., et al. "Remote heart rate measurement using low-cost RGB face video: a technical literature review." Frontiers of Computer Science 12.5 (2018): 858-872, and also in the dozens of references citing this reference.

Various embodiments described herein involve calculations based on machine learning approaches. Herein, the terms "machine learning approach" and/or "machine learning-based approaches" refer to learning from examples using one or more approaches. Examples of machine learning approaches include: decision tree learning, association rule learning, regression models, nearest neighbors classifiers, artificial neural networks, deep learning, inductive logic programming, support vector machines, clustering, Bayesian networks, reinforcement learning, representation learning, similarity and metric learning, sparse dictionary learning, genetic algorithms, rule-based machine learning, and/or learning classifier systems.

Herein, a "machine learning-based model" is a model trained using one or more machine learning approaches. For brevity's sake, at times, a "machine learning-based model" may simply be called a "model". Referring to a model as being "machine learning-based" is intended to indicate that the model is trained using one or more machine learning approaches (otherwise, "model" may also refer to a model generated by methods other than machine learning).

Herein, "feature values" (also known as feature vector, feature data, and numerical features) may be considered input to a computer that utilizes a model to perform the calculation of a value, such as a value indicative of one or more vital signs of a user. It is to be noted that the terms "feature" and "feature value" may be used interchangeably when the context of their use is clear. However, a "feature" typically refers to a certain type of value, and represents a property, while "feature value" is the value of the property with a certain instance (i.e., the value of the feature in a certain sample).

It is to be noted that when it is stated that feature values are generated based on data comprising multiple sources, it means that for each source, there is at least one feature value that is generated based on that source (and possibly other data). For example, stating that feature values are generated from an image capturing first and second regions ($IM_{ROI1}$ and $IM_{ROI2}$, respectively) means that the feature values include at least a first feature value generated based on $IM_{ROI1}$ and a second feature value generated based on $IM_{ROI2}$.

In addition to feature values generated based on measurements taken by sensors mentioned in a specific embodiment, at least some feature values utilized by a computer of the specific embodiment may be generated based on additional sources of data that were not specifically mentioned in the specific embodiment. Some examples of such additional sources of data include: (i) contextual information such as the time of day (e.g., to account for effects of the circadian rhythm), day of month (e.g., to account for effects of the lunar rhythm), day in the year (e.g., to account for seasonal effects), and/or stage in a menstrual cycle; (ii) information about the user being measured such as sex, age, weight, height, body build, genetics, medical records, and/or intake of substances; (iii) measurements of the environment, such as temperature, humidity level, noise level, elevation, air quality, a wind speed, precipitation, and infrared radiation; and/or (iv) values of physiological signals of the user obtained by sensors that are not mentioned in the specific embodiment, such as an electrocardiogram (ECG) sensor, an electroencephalography (EEG) sensor, a galvanic skin response (GSR) sensor, a movement sensor, an acoustic sensor, and/or a temperature sensor.

A machine learning-based model of a specific embodiment may be trained, in some embodiments, based on data collected in day-to-day, real world scenarios. As such, the data may be collected at different times of the day, while users perform various activities, and in various environmental conditions. Utilizing such diverse training data may enable a trained model to be more resilient to the various effects that different conditions can have on the measurements, and consequently, be able to achieve better detection of a required parameter in real world day-to-day scenarios.

The machine learning-based model may be personalized for a specific user. For example, after receiving a verified diagnosis of an extent of a physiological condition (such as blood pressure level, extent of a cardiovascular disease, extent of a pulmonary disease, extent of a migraine attack, etc.), the computed can use the verified diagnosis as labels and generate from a physiological measurement (such as the PPG signal, the temperature signal, the movement signal, and/or the audio signal) feature values to train a personalized machine learning-based model for the user. Then the computer can utilize the personalized machine learning-based model for future calculations of the extent of the physiological condition based on feature values.

Sentences in the form of "inward-facing head-mounted camera" refer to a camera configured to be worn on a user's head and to remain pointed at its ROI, which is on the user's face, also when the user's head makes angular and lateral movements (such as movements with an angular velocity above 0.1 rad/sec, above 0.5 rad/sec, and/or above 1 rad/sec). A head-mounted camera (which may be inward-facing and/or outward-facing) may be physically coupled to a frame worn on the user's head, may be physically coupled to eyeglasses using a clip-on mechanism (configured to be attached to and detached from the eyeglasses), may be physically coupled to a hat or a helmet, or may be mounted to the user's head using any other known device that keeps the camera in a fixed position relative to the user's head also when the head moves. Sentences in the form of "sensor physically coupled to the frame" mean that the sensor moves with the frame, such as when the sensor is fixed to (or integrated into) the frame, and/or when the sensor is fixed to (or integrated into) an element that is physically coupled to the frame, and/or when the sensor is connected to the frame with a clip-on mechanism.

Sentences in the form of "a frame configured to be worn on a user's head" or "a frame worn on a user's head" refer to a mechanical structure that loads more than 50% of its weight on the user's head. For example, an eyeglasses frame may include two temples connected to two rims connected by a bridge; the frame in Oculus Rift™ includes the foam placed on the user's face and the straps; and the frame in Google Glass™ is similar to an eyeglasses frame. Additionally or alternatively, the frame may connect to, be affixed within, and/or be integrated with, a helmet (e.g., a safety helmet, a motorcycle helmet, a combat helmet, a sports helmet, a bicycle helmet, etc.), goggles, and/or a brainwave-measuring headset.

Sentences in the form of "a frame configured to be worn on a user's head in a consistent manner" refer to a frame that is located in the same position relative to the head when worn repeatedly, and thus sensors attached to that frame are most likely to be positioned each time at the same location relative to the head. For example, eyeglasses frames, goggles, and helmets are all included under the definition of a frame that is worn in a consistent manner. However, a flexible headband, or adhesive sensors that are placed manually one by one, are not worn in a consistent manner, because these sensors are most likely to be positioned each time in a different location relative to the head.

The term "smartglasses" refers to any type of a device that reminds eyeglasses, and includes a frame configured to be worn on a user's head in a consistent manner, and includes electronics to operate one or more sensors. The frame may be an integral part of the smartglasses, and/or an element that is connected to the smartglasses. Examples of smartglasses include: any type of eyeglasses with electronics (whether prescription or plano), sunglasses with electronics, safety goggles with electronics, sports goggle with electronics, augmented reality devices, virtual reality devices, and mixed reality devices. In addition, the term "eyeglasses frame" refers to one or more of the following devices, whether with or without electronics: smartglasses, prescription eyeglasses, plano eyeglasses, prescription sunglasses, plano sunglasses, safety goggles, sports goggle, an augmented reality device, virtual reality devices, and a mixed reality device.

The term "smart-helmet" refers to a helmet that includes a frame configured to be worn on a user's head in a consistent manner, and includes electronics to operate one or more sensors. The frame may be an integral part of the smart-helmet, and/or an element that is connected to the smart-helmet. Examples of smart-helmets include: a safety helmet with electronics, a motorcycle helmet with electronics, a combat helmet with electronics, a sports helmet with electronics, and a bicycle helmet with electronics.

Examples of electronics that may be included in smartglasses and/or a smart-helmet include one or more of the following electronic components: a computer, a microcontroller, a processor, a memory, and a communication interface. The electronics of the smartglasses and/or smarthelmets may be integrated in various ways. For example, the electronics may be integrated into the package of one of the sensors, such as a camera housing that is physically coupled to a helmet, where the housing includes the imaging sensor and its processor, memory, power supply and wireless communication unit. In another example, the electronics may be integrated into the frame, such as a microcontroller, power supply and wireless communication unit that are integrated into an eyeglasses frame, and configured to operate a PPG device and a microphone that are physically coupled to the frame.

The term "Visible-light camera" refers to a non-contact device designed to detect at least some of the visible spectrum, such as a video camera with optical lenses and CMOS or CCD sensor. The term "thermal camera" refers to a non-contact device that measures electromagnetic radiation having wavelengths longer than 2500 nanometer (nm) and does not touch its region of interest (ROI). A thermal camera may include one sensing element (pixel), or multiple sensing elements that are also referred to herein as "sensing pixels", "pixels", and/or focal-plane array (FPA). A thermal camera may be based on an uncooled thermal sensor, such as a thermopile sensor, a microbolometer sensor (where microbolometer refers to any type of a bolometer sensor and its equivalents), a pyroelectric sensor, or a ferroelectric sensor.

A reference to a "camera" herein may relate to various types of devices. In one example, a camera may be a visible-light camera. In another example, a camera may capture light in the ultra-violet range. In another example, a camera may capture near infrared radiation (e.g., wavelengths between 750 and 2000 nm). And in still another example, a camera may be a thermal camera.

When a camera is inward-facing and head-mounted, challenges faced by systems known in the art that are used to acquire images, which include non-head-mounted cameras, may be simplified and even eliminated with some of the embodiments described herein. Some of these challenges may involve dealing with complications caused by movements of the user, image registration, region of interest (ROI) alignment, tracking based on hot spots or markers, and motion compensation.

The term "temperature sensor" refers to a device that measures temperature and/or temperature change. The temperature sensor may be a contact thermometer (such as a thermistor, a thermocouple), and/or a non-contact thermal cameras (such as a thermopile sensor, a microbolometer sensor, a pyroelectric sensor, or a ferroelectric sensor). Some examples of temperature sensors useful to measure skin temperature include: thermistors, thermocouples, thermoelectric effect, thermopiles, microbolometers, and pyroelectric sensors. Some examples of temperature sensors useful to measure environment temperature include: thermistors, resistance temperature detectors, thermocouples; thermopiles, and semiconductor-based sensors.

The term "movement sensor" refers to a sensor comprising one or more of the following components: a 3-axis gyroscope, a 3-axis accelerometer, and a 3-axis magnetometer. The movement sensor may also include a sensor that measures barometric pressure.

The term "acoustic sensor" refers to a device that converts sound waves into an electrical signal. An acoustic sensor can be a microphone, such as a dynamic microphone that works via electromagnetic induction, a piezoelectric microphone that uses the phenomenon of piezoelectricity, a fiber-optic microphone that converts acoustic waves into electrical signals by sensing changes in light intensity, a Micro-Electrical-Mechanical System (MEMS) microphone (such as silicon MEMS and piezoelectric MEMS), and/or other sensors that measure sound waves, such as described in the following examples: (i) Han, Jae Hyun, et al. "Basilar membrane-inspired self-powered acoustic sensor enabled by highly sensitive multi tunable frequency band." Nano Energy 53 (2018): 198-205, describes a self-powered flexible piezoelectric acoustic sensor having high sensitivity, (ii) Rao, Jihong, et al. "Recent Progress in Self-Powered Skin Sensors." Sensors 19.12 (2019): 2763. describes various self-powered acoustic skin sensors, such as an integrated triboelectric nanogenerator (TENG) with a polymer tube that can pick up and recover human throat voice even in an extremely noisy or windy environment, and (iii) Scanlon, Michael V. Acoustic sensor for voice with embedded physiology. Army Research Lab Adelphi Md., 1999, describes a gel-coupled acoustic sensor able to collect information related to the function of the heart, lungs, and changes in voice patterns.

Herein, the term "blood pressure" is indicative of one or more of the following: the systolic blood pressure of the user, the diastolic blood pressure of the user, and the mean arterial pressure (MAP) of the user. It is specifically noted that the term "blood pressure" is not limited to the systolic and diastolic blood pressure pair.

The terms "substance intake" or "intake of substances" refer to any type of food, beverage, medications, drugs, smoking/inhaling, and any combination thereof.

Blood flow in the face can cause certain facial coloration due to concentration of hemoglobin in various vessels such as arterioles, capillaries, and venules. In some embodiments described herein, coloration at a certain facial region, and/or changes thereto (possibly due to varying volume of blood in the certain region at different stages of cardiac pulses), can represent a hemoglobin concentration pattern at the certain region. This pattern can change because of various factors that can affect blood flow and/or vascular dilation, such as the external temperature, core body temperature, the emotional state, consumption of vascular dilating substances, and more. Embodiments described herein utilize analysis of images of the user's face, in which a hemoglobin concentration pattern can be detected, in order to detect various phenomena that may influence facial temperature, such as having a fever, being intoxicated, and/or in order to estimate physiological parameters such as the core body temperature.

In some embodiments, a hemoglobin concentration pattern calculated from images refers to a color mapping of various portions of the area captured in the images (e.g., the mapping provides the colors of different pixels in the images). In one example, the color mapping provides values that are average intensities of one or more colors of the pixels over a period of time during which the images were taken (e.g., values from one or more channels in the images). In another example, the color mapping provides values that are average intensities of one or more colors of the pixels over a period of time during which the images were taken (e.g., values of the maximum of one or more channels in the images). In yet another example, a hemoglobin concentration pattern may be a function of one or more colors (channels) of the pixels over a period of time during which the images were taken.

In other embodiments, a hemoglobin concentration pattern may refer to time series data, such as a sequence of images representing a progression of a pulse wave in the area. Different physiological conditions, such as different skin or core body temperatures or emotional responses, may produce different sequences of representative images, which depend on the structure of the facial blood vessels of the user and their dilation.

In still other embodiments, a hemoglobin concentration pattern may refer to a contour map, representing the extent to which pixels at a certain wavelength (e.g., corresponding to the color red) have at least a certain value. Since the extent of hemoglobin concentration is correlated with an increase in intensity of certain colors (e.g., red), a hemoglobin concentration pattern for more dilated blood vessels will have different contour map than the contour map observed in a hemoglobin concentration pattern for that blood vessels when it is more contracted.

A hemoglobin concentration pattern, such as one of the examples described above, may be calculated, in some embodiments, from images by a computer, such as computer 340 (described below). Optionally, the hemoglobin concentration pattern may be utilized to generate one or more feature values that are used in a machine learning-based approach by the computer for various applications, such as detecting fever, calculating core body temperature, detecting intoxication, and/or other applications described below. In other embodiments, the hemoglobin concentration pattern may be utilized to calculate additional values used to represent the extent of facial blood flow and/or extent of vascular dilation, which may be evaluated, e.g., by comparing the extent of blood flow and/or vascular dilation to thresholds in order to detect whether the user has a fever, estimate core body temperature, detect alcohol intoxication, and/or for other applications described herein.

In one embodiment, a hemoglobin concentration pattern may be converted to a value representing the proportion of the area in which the intensities of pixels reach a threshold. In one example, the intensities being evaluated may be average intensities (e.g., average pixel intensities in the images). In another example, the intensities being evaluated may be maximum intensities corresponding to times of systolic peaks (e.g., as determined by detecting the spread of a pulse wave in the area captured in the images, and/or using a reference signal from a different source such as a PPG sensor that is not the camera that captured the images).

In another embodiment, a hemoglobin concentration pattern may be compared with one or more reference hemoglobin concentration patterns that may correspond to specific physiological conditions (e.g., having a fever, not having a fever, or a specific core body temperature). Optionally, the reference patterns may be based on previously taken images of the user, which were taken at times for which the user's core body temperature was known (e.g., based on a measurement using a thermometer). Optionally, similarity of a hemoglobin concentration pattern to a reference pattern may be utilized to generate one or more feature values utilized in a machine learning approach, as described below. Optionally, the extent of similarity of a hemoglobin concentration pattern to a reference pattern may be utilized to determine whether the user has a certain condition (e.g., fever), as described below.

Various embodiments described herein involve a computer that calculates a hemoglobin concentration pattern. Optionally, values in a hemoglobin concentration pattern may be mapped to specific regions on the face, such that the hemoglobin concentration pattern may be considered a layer or grid that can be mapped onto the face in a predetermined manner.

There are various ways in which a hemoglobin concentration pattern may be calculated in embodiments described herein. Optionally, calculating a hemoglobin concentration pattern involves processing the images, for example, in order to accentuate the color of one or more channels in the images, and/or accentuate the changes to colors of one or more channels in the images (e.g., accentuating color changes caused by blood flow from cardiac pulses). Additionally or alternatively, calculating a hemoglobin pattern may involve calculating a representation of the pattern by assigning values to regions in the images and/or to a representation of regions on the face. Optionally, the values may represent extents of one or more color channels at the different regions. Optionally, the values may represent changes to extents of one or more color channels at the different regions. Optionally, the values may include time series data representing temporal changes to extents of one or more color channels at each of at least some of the different regions.

The following are some examples of processing methods that may be applied to images in order to calculate a hemoglobin concentration pattern based on images. In some embodiments, one or more of the processing methods may be applied by the computer before hemoglobin concentration patterns are used for calculations and/or detections (e.g., prior to detecting fever, intoxication, and/or estimating core body temperature). For example, the images may be processed using one or more of the methods described below, prior to their utilization by the computer to calculate hemoglobin concentration patterns used for the calculations and/or detections. In some embodiments, one or more of the processing methods may be applied by the computer as part of the calculations and/or detections. For example, some layers and/or portions of a deep learning network used by the computer for the calculations and/or detections may implement processing operations of the images (which are involved in calculating the hemoglobin concentration patterns), while other portions of the deep learning network are used to perform the calculations and/or detections on values representing the hemoglobin concentration patterns.

Various preprocessing approaches may be utilized in order to assist in calculating hemoglobin concentration patterns based on images. Some non-limiting examples of the preprocessing approaches that may be used include: normalization of pixel intensities (e.g., to obtain a zero-mean unit variance time series signal), and conditioning a time series signal by constructing a square wave, a sine wave, or a user defined shape, such as that obtained from an ECG signal or a PPG signal as described in U.S. Pat. No. 8,617,081, titled "Estimating cardiac pulse recovery from multi-channel source data via constrained source separation". Additionally or alternatively, images may undergo various preprocessing to improve the signal, such as color space transformation (e.g., transforming RGB images into a monochromatic color or images in a different color space), blind source separation using algorithms such as independent component analysis (ICA) or principal component analysis (PCA), and various filtering techniques, such as detrending, bandpass filtering, and/or continuous wavelet transform (CWT). Various preprocessing techniques known in the art that may assist in extracting an iPPG signal from the images are discussed in Zaunseder et al. (2018), "Cardiovascular assessment by imaging photoplethysmography-a review", Biomedical Engineering 63(5), 617-634. An example of preprocessing that may be used in some embodiments is given in U.S. Pat. No. 9,020,185, titled "Systems and methods for non-contact heart rate sensing", which describes how times-series signals obtained from video of a user can be filtered and processed to separate an underlying pulsing signal by, for example, using an ICA algorithm.

Another approach that may be utilized as part of preprocessing and/or calculation of hemoglobin concentration patterns involves Eulerian video magnification, as described in Wu, Hao-Yu, et al. "Eulerian video magnification for revealing subtle changes in the world." ACM transactions on graphics (TOG) 31.4 (2012): 1-8, and also in the hundreds of references citing this reference. The goal of Eulerian video magnification is to reveal temporal variations in videos that are difficult or impossible to see with the naked eye and display them in an indicative manner. This method takes a standard video sequence as input, and applies spatial decomposition, followed by temporal filtering to the frames. The resulting signal is then amplified to reveal hidden information. This method is successfully applied in many applications in order to visualize the flow of blood as it fills the face and also to amplify and reveal small motions.

Figure 1B:
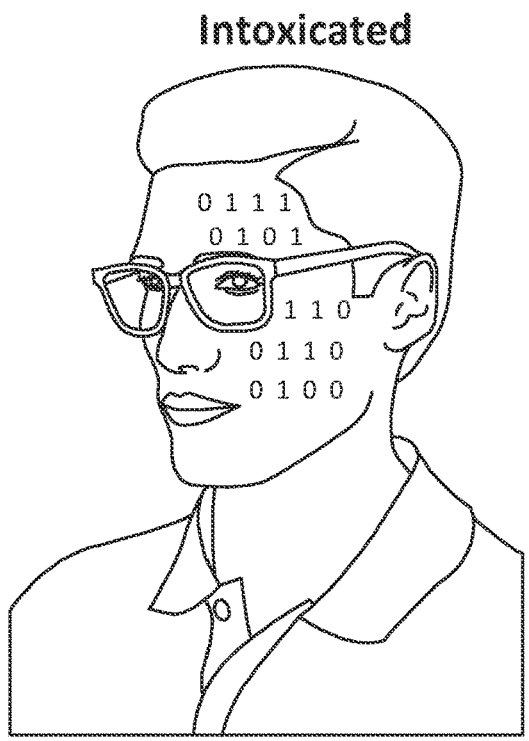
FIG. 1b illustrates an example of the hemoglobin concentration pattern of the same person when intoxicated.

In one embodiment, calculating a hemoglobin concentration pattern may involve assigning values to regions on the face and/or in the images that are binary values. FIG. 1a illustrates an example of a hemoglobin concentration pattern of a sober person where certain regions have a value "0" because the color of the red channel in the certain regions is below a certain threshold, and other regions have a value "1" because the color of the red channel in the other regions is above the threshold. FIG. 1b illustrates an example of the hemoglobin concentration pattern of the same person when intoxicated, and as a result the face is redder in certain locations.

In another embodiment, calculating a hemoglobin concentration pattern may involve assigning values to regions on the face and/or in the images, which are continuous. In one example, in a first hemoglobin concentration pattern, the pattern may include values in a two-dimensional grid corresponding to average intensities and/or maximum intensities of colors from one or more channels. In another example, in a second hemoglobin concentration pattern, the pattern may include values obtained after processing the images using techniques described herein for extracting iPPG signals. Thus, the pattern, in this example, may include values representing statistics of PPG signals at different regions on the face (e.g., the pattern may include values that are the average or maximum of the PPG signals at the different regions). In another example, the pattern may include averages of values of certain fiducial points (e.g., systolic peaks and/or dicrotic notches) extracted from PPG signals at different regions using iPPG techniques known in the art.

In yet another embodiment, calculating a hemoglobin concentration pattern may involve assigning values to regions on the face and/or in the images, which are a time series. In one example, in a hemoglobin concentration pattern, the pattern may include values in a two-dimensional grid, where each position in the gird is a time series that represents a shape of a PPG pulse wave at the location on the face corresponding to the position. Optionally, the time series for the position may be extracted from images corresponding to multiple pulse waves (and thus represent a typical PPG shape of a pulse wave at location on the face).

Figure 1C:
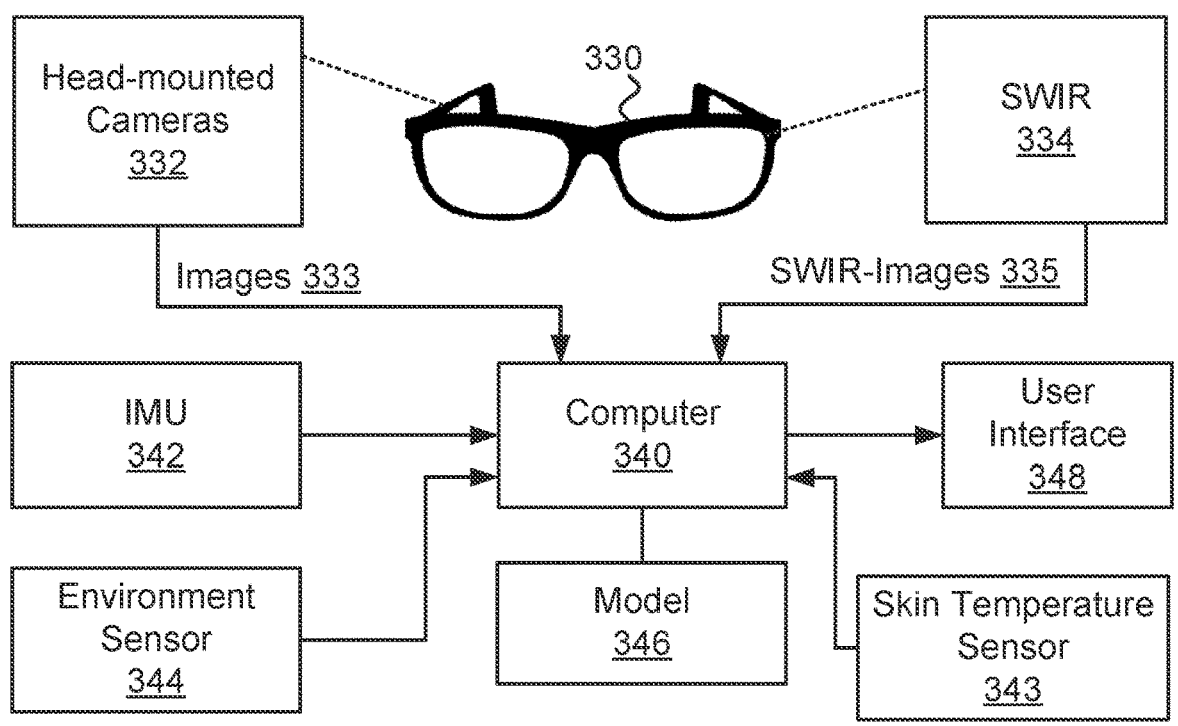
FIG. 1c is a schematic illustration of components of a system configured to detect fever and/or intoxication.

FIG. 1c is a schematic illustration of components of a system configured to detect fever and/or intoxication (e.g., due to alcohol consumption). In one embodiment, the system includes at least first and second head-mounted inward-facing cameras 332 that take images 333 of respective first and second regions on a user's face. Henceforth, for the sake of brevity, "the first and second head-mounted inward-facing cameras 332" will be referred to as "the cameras 332". Optionally, the cameras 332 are physically coupled to a frame of smartglasses 330. The system also includes a computer 340, which may or may not be physically coupled to the frame of the smartglasses 330. The system may include additional elements such as a movement sensor, an inertial measurement unit (IMU) 342, a skin temperature sensor 343, an environment sensor 344 that is configured to measure temperature and/or humidity of the environment, and/or a user interface 348.

In one embodiment, the computer 340 calculates, based on baseline images captured with the cameras 332 while the user did not have a fever, a baseline pattern comprising values indicative of first and second baseline hemoglobin concentrations at the first and second regions on the user's face, respectively. Additionally, the computer 340 calculates, based on a current set of images captured with the cameras 332, a current pattern comprising values indicative of first and second current hemoglobin concentrations at the first and second regions, respectively. In this embodiment, the computer 340 detects whether the user has a fever based on a deviation of the current pattern from the baseline pattern.

In some embodiments, the user is considered to have a fever if the user's body temperature rises above a predetermined extent beyond the baseline ("normal") body temperature for the user. For example, if the user's body temperature rises by 1.5° C. or more above normal, the user is considered to have a fever. In other embodiments, the user is considered to have a fever if the user's body temperature rises above a predetermined threshold (which may or may not be specific to the user, and may or may not depend on the hour of the day because the normal temperature may be a function of the hour of the day). For example, if the user's body temperature rises above 38° C., the user is considered to have a fever.

In another embodiment, the computer 340 calculates, based on baseline images captured with the cameras 332 while the user was sober, a baseline pattern comprising values indicative of first and second baseline hemoglobin concentrations at the first and second regions on the user's face, respectively. Additionally, the computer 340 calculates, based on a current set of images captured with the cameras 332, a current pattern comprising values indicative of first and second current hemoglobin concentrations at the first and second regions, respectively. In this embodiment, the computer 340 detects whether the user is intoxicated based on a deviation of the current pattern from the baseline pattern.

In some embodiments, the user is considered to be intoxicated (from alcohol) if the user's Blood Alcohol Level (BAC) is above a predetermined threshold. For example, the user may be considered intoxicated if the BAC is above 0.05%, 0.08%, or 0.1%. In other embodiments, the user may be considered intoxicated if the user consumed at least a certain amount of alcohol during a preceding window of time. For example, the user may be considered intoxicated if the user consumed at least two standard drinks (e.g., two bottles of beer with 5% alcohol content) during a period of two hours or less. In still other embodiments, the user may be considered intoxicated if the user is assessed to exhibit behavior consistent with intoxication and/or is considered unable to care for the safety of oneself or others.

The smartglasses 330 are configured to be worn on a user's head. Optionally, various sensors and/or cameras that are physically coupled to the smartglasses 330, e.g., by being attached to and/or embedded in the frame of the smartglasses 330, are used to measure the user while the user wears the smartglasses 330. Optionally, at least some of the sensors and/or cameras that are physically coupled to the smartglasses 330 may be utilized to measure the environment in which the user is in. In one example, the smartglasses 330 are eyeglasses with sensors and electronics attached thereto and/or embedded therein. In another example, the smartglasses 330 may be an extended reality device (i.e., an augmented realty device, a virtual reality device, and/or mixed reality device). In some embodiments, the cameras 332 are physically coupled to the frame of the smartglasses 330.

Each camera from among the cameras 332 is located less than 10 cm from the face of the user (to whose head the cameras are mounted). Additionally, the first and second head-mounted inward-facing cameras 332 are configured to capture images of respective first and second regions on the user's face (i.e., the first camera captures images of the first region and the second camera captures images of the second region). The first and second regions do not completely overlap.

Having multiple inward-facing head-mounted cameras close to the face can confer the advantage of covering many regions on the face, while still having an aesthetic head-mounted system (due to the close distances of the cameras from the face) and stable and sharp images (due to the cameras capturing the same regions even when the user makes angular motions). In some embodiments, the cameras 332 may be at closers distances to the face. In one example, each of the cameras 332 is less than 5 cm from the user's face. In another example, each of the cameras 332 is less than 2 cm from the user's face.

The locations, orientations, and/or optical properties of the first and second head-mounted inward-facing cameras 332 can cause them to capture images of different respective first and second regions. Optionally, each of the first and second regions contains an area of at least 1 cm$^2$ of skin on the user's face. Optionally, each of the first and second regions contains an area of at least 4 cm$^2$ of skin on the user's face.

In some embodiments, the middle of the first region is not at the same location as the middle of the second region. In one example, the middles of the first and second regions are at least 1 cm apart. In another example, the middles of the first and second regions are at least 4 cm apart. In yet another example, the middles of the first and second regions are at least 8 cm apart.

Herein, the middle of a region is the average co-ordinate of points in the region (e.g., when points in the region can be described as residing in a two- or three-dimensional space).

In one example, the first region is located above the user's eyes, and the second region is located below the user's eyes. Optionally, in this example, the first and second regions do not overlap. In another example, the middle of the first region is located less than 4 cm from the vertical symmetric axis of the user's face, and the middle of the second region is located more than 4 cm from the vertical symmetric axis. Optionally, in this example, the first and second regions do overlap.

The first and second head-mounted inward-facing cameras 332 are small and lightweight. In some embodiments, each of the cameras 332 weighs below 10 g and even below 2 g. In one example, each of these cameras is a multi-pixel video camera having a CMOS or a CCD sensor. The video camera may capture images at various rates. In one example, the images 333 include images captured at a frame rate of at least 3 frames per second (fps). In another example, the images 333 include images captured at a frame rate of at least 30 fps. In still another example, the images 333 include images captured at a frame rate of at least 256 fps. Images taken by the cameras 332 may have various resolutions. In one example, the images 333 include images that have a resolution of at least 8×8 pixels. In another example, the images 333 include images that have a resolution of at least 32×32 pixels. In yet another example, the images 333 include images that have a resolution of at least 640×480 pixels.

In some embodiments, at least one of the cameras 332 may capture light in the near infrared spectrum (NIR). Optionally, such a camera may include optics and sensors that capture light rays in at least one of the following NIR spectrum intervals: 700-800 nm, 700-900 nm, 700-1,050 nm. Optionally, the sensors may be CCD sensors designed to be sensitive in the NIR spectrum and/or CMOS sensors designed to be sensitive in the NIR spectrum.

In one example, the cameras 332 are mounted between 5 mm and 50 mm away from the user's head. Examples of camera sensors that are sensitive to wavelengths below 1050 nm include CCD and CMOS sensors, which are sensitive to wavelengths in at least a portion of the range of 350 nm to 1050 nm.

In some embodiments, the system may include an optical emitter configured to direct electromagnetic radiation at the first and/or second regions. Optionally, the optical emitter comprises one or more of the following: a laser diode (LD), a light-emitting diodes (LED), and an organic light-emitting diode (OLED). It is to be noted that when embodiments described in this disclosure utilize optical emitters directed at a region of interest (ROI), such as an area appearing in images 333, the optical emitter may be positioned in various locations relative to the ROI. In some embodiments, the optical emitter may be positioned essentially directly above the ROI, such that electromagnetic radiation is emitted at an angle that is perpendicular (or within 10 degrees from being perpendicular) relative to the ROI. Optionally, a camera may be positioned near the optical emitter in order to capture the reflection of electromagnetic radiation from the ROI. In other embodiments, the optical emitter may be positioned such that it is not perpendicular to the ROI. Optionally, the optical emitter does not occlude the ROI. In one example, the optical emitter may be located at the top of a frame of a pair of eyeglasses, and the ROI may include a portion of the forehead. In another example, optical emitter may be located on an arm of a frame of a pair of eyeglasses and the ROI may be located above the arm or below it.

Due to the position of the cameras 332 relative to the face, in some embodiments, there may be an acute angle between the optical axis of a camera from among these cameras and the area captured by images taken by said camera (e.g., when the camera is fixed to an eyeglasses frame and the area is on, and/or includes a portion of, the forehead or a cheek). In order to improve the sharpness of images captured by said camera, the camera may be configured to operate in a way that takes advantage of the Scheimpflug principle. In one embodiment, a camera from among the cameras 332 includes a sensor and a lens; the sensor plane is tilted by a fixed angle greater than 20 relative to the lens plane according to the Scheimpflug principle in order to capture a sharper image when the smartglasses are worn by the user (where the lens plane refers to a plane that is perpendicular to the optical axis of the lens, which may include one or more lenses). In another embodiment, the camera includes a sensor, a lens, and a motor; the motor tilts the lens relative to the sensor according to the Scheimpflug principle. The tilt improves the sharpness of images when the smartglasses are worn by the user.

In some embodiments, the system may include a shortwave infrared (SWIR 334) inward-facing head-mounted camera that is configured to detect wavelengths in at least a portion of the range of 700 nm to 2500 nm. One example of a SWIR sensor suitable for this embodiment is Indium Gallium Arsenide (inGaAs) sensor. Optionally, the computer 340 is configured to detect whether the user has the fever also based on a deviation of a current SWIR pattern from a baseline SWIR pattern taken while the user did not have a fever. Optionally, the current SWIR pattern is generated based on images taken with the SWIR 334 at a current time, while the baseline SWIR pattern is generated based on SWIR-images 335 taken with the SWIR 334 during one or more previous periods, while the user did not have a fever. In some embodiments, at least some of the feature values, described further below, which are generated based on images from among the images 333 may be generated for the SWIR-images 335. Thus, SWIR-images 335 may be utilized, in some embodiments, as inputs for a detection of whether the user has a fever and/or is intoxicated.

Variations in the reflected ambient light may introduce artifacts into images collected with inward-facing cameras that can add noise to these images and make detections and/or calculations based on these images less accurate. In some embodiments, the system includes an outward-facing camera, which is coupled to the smartglasses, and takes images of the environment. Optionally, this outward-facing camera is located less than 10 cm from the user's face and weighs below 5 g. Optionally, the outward-facing camera may include optics that provide it with a wide field of view.

The computer 340 is configured, in some embodiments, to detect a certain condition (e.g., whether the user has a fever or whether the user is intoxicated) based on a deviation of a current pattern from a baseline pattern.

In different embodiments, a reference to "the computer 340" may refer to different components and/or a combination of components. In some embodiments, the computer 340 may include a processor located on a head-mounted device, such as the smartglasses 330. In other embodiments, at least some of the calculations attributed to the computer 340 may be performed on a remote processor, such as the user's smartphone and/or a cloud-based server. Thus, references to calculations being performed by the "computer 340" should be interpreted as calculations being performed utilizing one or more computers, with some of these one or more computers possibly being of a head-mounted device to which the cameras 332 are coupled.

The current pattern is calculated, by the computer 340, based on current images, from among the images 333, captured by the cameras 332. The current images are taken during some times that fall during a window leading up to a current time. Optionally, the window is at most five second long. Optionally, the window is at most 30 seconds long. Optionally, the window is at most 5 minutes long. Optionally, the window is at most one hour long. The current images taken during the window are utilized by the computer 340 to calculate the current pattern, which is indicative of at least first and second current hemoglobin concentrations at the first and second regions, respectively. It is to be noted that images taken during the window need not be taken continuously throughout the window, rather they may be taken intermittently or sporadically during the window.

As discussed below, extents of reflection and absorption of light through the skin may depend on the wavelength of the light. Thus, in some embodiments, patterns of hemoglobin concentration may include values calculated based on different channels of the same images. Thus, in the detection of fever and/or intoxication, the baseline pattern and/or current pattern may include multiple sets of values derived from multiple different channels.

The baseline pattern is calculated, by the computer 340, based on baseline images from among the images 333, captured by the cameras 332. Optionally, the baseline images were taken previously (prior to when the current images were taken) while the user was not in a state being detected. In one embodiment, in which the computer 340 detects whether the user has a fever, the baseline images were taken while the user did not have a fever. In another embodiment, in which the computer 340 detects whether the user is intoxicated, the baseline images were taken while the user was sober (or assumed to be sober).

Windows during which baseline images were taken may have different lengths, and end prior to the current time. Optionally, windows during which baseline images are taken end before the current window begins. In one example, the baseline images may have been taken at different times during a window spanning several hours. In another example, the baseline images include images taken at different times during a window spanning several days/weeks/months, such that the baseline images include images taken on different days/weeks/months, respectively.

In some embodiments, the computer 340 may receive indications indicative of times in which the user is in a baseline state (e.g., without a fever or not intoxicated). Optionally, at least some of the baseline images are selected based on the indications. For example, images taken by the cameras 332 are included in the baseline images if there is an indication indicating the user was in a baseline state within temporal proximity to when they were taken. In one example, images taken within a window spanning from an hour before to an hour after a time for which there is an indication that the user was in a baseline state, are included in the baseline images. In another example, images taken within a window spanning from five minutes before to five minutes after a time for which there is an indication that the user was in a baseline state, are included in the baseline images. In yet another example, images taken within a window spanning from 30 seconds before to 30 seconds after a time for which there is an indication that the user was in a baseline state, are included in the baseline images.

The indications indicative of the times in which the user is in a baseline state may come from one or more sources. In some embodiments, indications may be self-reported. For example, the user may provide indications indicating when he/she were sober and/or without a fever. In other embodiments, some other person such as a caregiver, physician, supervisor, and/or guardian may provide such indications. In still other embodiments, indications may be received from sensors that measure the user, which are not the cameras 332. In one example, temperature measurements taken by an oral thermometer and/or a non-head-mounted thermal camera are used to determine whether the user has a fever. In another example, analysis of the user's movements (e.g., as measured by the IMU 342) and/or voice patterns (as recorded with microphones) are used to determine whether the user is intoxicated or not (e.g., using machine learning methods known in the art).

In some embodiments, images taken in a certain context are assumed to be taken in a baseline state. In one example, images taken in the daytime at school/work, while the user behaved as expected from a sober/healthy person, are assumed to be taken while the user was not intoxicated and/or without a fever. In another example, all images taken while there is no indication that the user was not in a baseline state, are assumed to be taken in the baseline state. In this example, it may be assumed (for most normative people) that most of the time the user does not have a fever and/or is not intoxicated.

The baseline images are utilized by the computer 340 to calculate the baseline pattern, which is indicative of at least first and second baseline hemoglobin concentrations at the first and second regions, respectively. In one example, the baseline pattern is indicative of first and second baseline hemoglobin concentrations at the first and second regions characteristic of times at which the user does not have a fever, or is not intoxicated.

In addition to a baseline pattern indicating hemoglobin concentrations characteristic of times in which the user is in a baseline state, in some embodiments, the computer 340 may utilize a detected-state pattern indicating hemoglobin concentrations characteristic of times in which the user is in the detected state (e.g., has a fever and/or is intoxicated). Optionally, detection of whether the user is in the detected state is done by a deviation of the current pattern from the detected-state pattern. Optionally, the detected-state pattern is calculated by the computer 340 based on additional images, from among the images 333, taken at times at which there was an indication that the user was in a certain state (e.g., had a fever and/or was intoxicated). Optionally, the indications may be self-reported, provided by another person, and/or a result of analysis of sensor measurements, as described above.

In one embodiment, the computer 340 calculates, based on additional baseline images captured with the cameras 332 while the user had a fever, a fever-baseline pattern comprising values indicative of first and second fever hemoglobin concentrations at the first and second regions, respectively. The computer 340 then bases the detection of whether the user has the fever also on a deviation of the current pattern from the fever-baseline pattern (in addition to the deviation from the baseline pattern).

In one embodiment, the computer 340 calculates, based on additional baseline images captured with the cameras 332 while the user was intoxicated, an intoxication-baseline pattern comprising values indicative of first and second intoxication hemoglobin concentrations at the first and second regions, respectively. The computer 340 then bases the detection of whether the user is intoxicated also based on a deviation of the current pattern from the intoxication-baseline pattern in addition to the deviation from the baseline pattern).

Detection of reflections of light at different wavelengths can be used to account for thermal interference by the environment. In some embodiments, accounting for thermal inference relies on the following three observations:
(i) blue and green wavelengths penetrate the skin less deeply compared to red and near-infrared wavelengths, (ii) the capillaries are closer to the skin surface compared to the arterioles, and (iii) the PPG amplitude is proportional to the skin temperature, probably because both blood viscosity and vasoconstriction increase with the increase in skin temperature. Additionally, we will examine the ratio $R_{depth}$, which is defined as follows $$R_{depth} = \frac{\text{reflected light from the capillaries}}{\text{reflected light from the arterioles}}$$

Based on the aforementioned observations, it is to be expected that $R_{depth}$ will be greater for the blue and green wavelengths compared to the red and near-infrared wavelengths. This means that temperature interference from the environment is expected to influence the hemoglobin concentration pattern derived from the blue and green wavelengths more than it influences the hemoglobin concentration pattern derived from the red and near-infrared wavelengths.

In one embodiment, because environment heating increases vasodilation whilst environment cooling decreases blood flow to the skin, and because temperature interference from the environment is expected to influence a hemoglobin concentration pattern derived from the blue and/or green wavelengths more than it influences a hemoglobin concentration pattern derived from the red and/or near-infrared wavelengths, the system can improve its accuracy when estimating temperatures, such as the core body temperature and/or detecting fever based on the level of discrepancy between (i) a hemoglobin concentration pattern derived from a first channel corresponding to wavelengths mostly below 580 nanometers, such as the blue and/or green reflections, and (ii) the hemoglobin concentration pattern derived from a second channel corresponding to wavelengths mostly above 580 nanometers, such as the red and/or near-infrared reflections.

It is noted that most optical filters are not perfect, and the meaning of the sentence "channel corresponding to wavelengths mostly below 580 nanometers" is that the filter suppresses red and near-infrared at least twice as much, compared to blue and/or green. Similarly, the meaning of the sentence "channel corresponding to wavelengths mostly above 580 nanometers" is that the filter suppresses blue and green at least twice as much, compared to red and/or near-infrared.

For example, when a temperature corresponding to hemoglobin concentration pattern derived from the blue and/or green wavelengths is higher than a predetermined threshold compared to a temperature corresponding to the hemoglobin concentration pattern derived from the red and/or near-infrared wavelengths, this may indicate that the user is in a hot environment (such as being close to a heater or in direct sunlight), and/or that the user has just arrived from a hot environment (such as entering a cold building from a hot summer street). In another example, when a temperature corresponding to hemoglobin concentration pattern derived from the blue and/or green wavelengths is lower than a predetermined threshold from the temperature corresponding to the hemoglobin concentration pattern derived from the red and/or near-infrared wavelengths, this may indicate that the user is in a cold environment, and/or that the user is being exposed to a wind that cools the skin.

In one embodiment, the baseline images and the current set of images comprise a first channel corresponding to wavelengths that are mostly below 580 nanometers and a second channel corresponding to wavelengths mostly above 580 nanometers; the baseline pattern comprises: (i) first values, derived based on the first channel in the baseline images, which are indicative of the first and second baseline hemoglobin concentrations at the first and second regions, respectively, and (ii) second values, derived based on the second channel in the baseline images, which are indicative of third and fourth baseline hemoglobin concentrations at the first and second regions, respectively. Optionally, the current pattern comprises: (i) third values, derived based on the first channel in the current set of images, which are indicative of the first and second current hemoglobin concentrations at the first and second regions, respectively, and (ii) fourth values, derived based on the second channel in the current set of images, which are indicative of third and fourth current hemoglobin concentrations at the first and second regions, respectively. Having separate values for different wavelengths enables to account for interference from the environment when detecting whether the user has the fever because temperature interference from the environment is expected to affect the third values more than it affects the fourth values.

In another embodiment, the baseline images and the current set of images comprise a first channel corresponding to wavelengths that are mostly below 580 nanometers and a second channel corresponding to wavelengths mostly above 580 nanometers; the baseline pattern comprises: (i) first values, derived based on the first channel in the baseline images, which are indicative of the first and second baseline hemoglobin concentrations at the first and second regions, respectively, and (ii) second values, derived based on the second channel in the baseline images, which are indicative of third and fourth baseline hemoglobin concentrations at the first and second regions, respectively. The current pattern comprises: (i) third values, derived based on the first channel in the current set of images, which are indicative of the first and second current hemoglobin concentrations at the first and second regions, respectively, and (ii) fourth values, derived based on the second channel in the current set of images, which are indicative of third and fourth current hemoglobin concentrations at the first and second regions, respectively. Optionally, the computer 340 calculates a confidence in a detection of the fever based on the deviation of the current pattern from the baseline pattern, such that the confidence decreases as the difference between the third values and the fourth values increases. For example, the confidence is a value proportional to said deviation. Having separate values for different wavelengths enables to account for interference from the environment when calculating said confidence because temperature interference from the environment is expected to affect the third values more than it affects the fourth values.

In some embodiments, the computer 340 calculates the values indicative of the baseline and current hemoglobin concentrations based on detecting facial flushing patterns in the baseline and current images. In one example, the facial flushing patterns are calculated based on applying decorrelation stretching to the images (such as using a three color space), then applying K-means clustering (such as three clusters corresponding to the three color space), and optionally repeating the decorrelation stretching using a different color space. In another example, the facial flushing patterns are calculated based on applying decorrelation stretching to the images (such as using a three color space), and then applying a linear contrast stretch to further expand the color range.

There are various computational approaches that may be utilized by the computer 340 in order to detect whether the user has a fever, and/or is intoxicated, based on a deviation of a current pattern from a baseline pattern.

In one embodiment, the computer 340 calculates a value indicative of a magnitude of the deviation of the current pattern from the baseline pattern. For example, when both patterns include numerical values, the values in corresponding regions in both patterns may be subtracted from each other. In FIG. 1a and FIG. 1b, this may be interpreted as calculating the difference in the number of "1"s in both patterns. Optionally, if the subtraction of the baseline pattern from the current pattern reaches a certain threshold, the user is assumed to be in a certain state (e.g., has a fever and/or is intoxicated).

In another embodiment, the computer 340 calculates a value indicative of the deviation between the current pattern and the baseline pattern based on vector representations of the patterns. For example, if each of the patterns may be represented as a vector in a multi-dimensional space, the deviation may be calculated using one or more techniques known in the art for calculating distances between vectors, such as a dot product, Euclidean distance, or a distance according to some other norm. Optionally, if the distance has at least a certain value, the user is assumed to be in a certain state (e.g., has a fever and/or is intoxicated).

In yet another embodiment, if the difference between a vector representation of the current pattern and a vector representation of the baseline pattern is in a certain direction, the computer 340 detects the user is in a certain state corresponding to the certain direction. For example, there may be a predetermined direction of change for patterns when the user becomes intoxicated.

In still another embodiment, in which the current pattern and the baseline pattern include time series data, the computer 340 utilizes methods known in the art for comparison of time series, such as dynamic time warping, in order to calculate an extent of deviation of the current pattern from the baseline pattern.

In some embodiments, the computer 340 may utilize the fever-baseline pattern and/or the intoxication-baseline pattern, which are discussed above, in order to detect whether the user has a fever and/or is intoxicated. In one example, if the current pattern is more similar to the fever-baseline pattern than it is to the baseline pattern, the computer 340 detect the user has a fever. In another example, if a first difference between the current pattern and the intoxication-baseline pattern is below a first threshold, while a second difference between the current pattern and the baseline pattern is above a second threshold, the computer 340 detects the user is intoxicated.

Detection of whether the user has a fever and/or is intoxicated may involve utilization of machine learning approaches. In some embodiments, baseline images and/or current images may be utilized by the computer 340 to generate feature values that are used in a machine learning-based approach by the computer 340 to detect whether the user has a fever and/or is intoxicated. In some embodiments, the computer 340 calculates the feature values based on data that includes at least some of the images 333 (and possibly other data) and utilizes a model 346 to calculate, based on the feature values, a value indicative of whether the user has a fever and/or a value indicative of whether the user is intoxicated.

In one embodiment, the value calculated by the computer 340 based on the feature values is a binary value. For example, the value is "1" if the user has a fever and "0" if the user does not have a fever. In some embodiments, the value calculated by the computer 340 based on the feature values is a scalar. For example, the calculated value may be an estimation of the user's core body temperature and/or an estimation of the increase of the user's core body temperature. In such embodiments, if the calculated value reaches a threshold, the user is considered to have a fever. In a similar fashion, a binary value may be calculated in the case of intoxication, and detecting intoxication may be done if a calculated value indicative of an intoxication level of the user reaches a predetermined threshold.

Generally, machine learning-based approaches utilized by embodiments described herein involve training a model on samples, with each sample including: feature values generated based on images taken by the cameras 332, and optionally other data, which were taken during a certain period, and a label indicative of an extent of fever and/or intoxication (during the certain period). Optionally, a label may be provided manually by the user and/or other sources described above as providing indications about the state of the user (e.g., indications of a fever level and/or intoxication level, described above). Optionally, a label may be extracted based on analysis of electronic health records of the user, generated while being monitored at a medical facility.

In some embodiments, the model 346 may be personalized for a user by training the model on samples that include: feature values generated based on measurements of the user, and corresponding labels indicative of the extent of fever and/or intoxication of the user while the measurements were taken. In some embodiments, the model 346 may be generated based on measurements of multiple users, in which case, the model 346 may be considered a general model. Optionally, a model generated based on measurements of multiple users may be personalized for a certain user by being retrained on samples generated based on measurements of the certain user.

There are various types of feature values that may be generated by the computer 340 based on input data, which may be utilized to calculate a value indicative of whether the user has a fever and/or is intoxicated. Some examples of feature values include "raw" or minimally processed values based on the input data (i.e., the features are the data itself or applying generic preprocessing functions to the data). Other examples of feature values include feature values that are based on higher-level processing, such a feature values determined based on domain-knowledge. In one example, feature values may include values of the patterns themselves, such as values included in the current pattern, the baseline pattern, the fever-baseline pattern, and/or the intoxication-baseline pattern. In another example, feature values may include values that are functions of patterns, such as values that represent a deviation of the current pattern from the baseline pattern.

In one non-limiting example, feature values generated by the computer 340 include pixel values from the images 333. In another non-limiting example, feature values generated by the computer 340 include timings and intensities corresponding to fiducial points identified in iPPG signals extracted from the images 333. In yet another non-limiting example, feature values generated by the computer 340 include binary values representing the baseline pattern and the current pattern.

The following are some examples of the various types of feature values that may be generated based on images from among the images 333 by the computer 340. In one embodiment, one or more of the feature values may be various low-level features derived from images, such as features generated using Gabor filters, local binary patterns (LBP) and their derivatives, algorithms such as SIFT and/or SURF (and their derivatives), image keypoints, histograms of oriented gradients (HOG) descriptors, and products of statistical procedures such independent component analysis (ICA), principal component analysis (PCA), or linear discriminant analysis (LDA). Optionally, one or more of the feature values may derived from multiple images taken at different times, such as volume local binary patterns (VLBP), cuboids, and/or optical strain-based features. In one example, one or more of the feature values may represent a difference between values of pixels at one time t at a certain location on the face and values of pixels at a different location at some other time t+x (which can help detect different arrival times of a pulse wave).

In some embodiments, at least some feature values utilized by the computer 340 describe properties of the cardiac waveform in an iPPG signal derived from images from among the images 333. To this end, the computer 340 may employ various approaches known in the art to identify landmarks in a cardiac waveform (e.g., systolic peaks, diastolic peaks), and/or extract various types of known values that may be derived from the cardiac waveform, as described in the following examples.

In one embodiment, at least some of the feature values generated based on the iPPG signal may be indicative of waveform properties that include: systolic-upstroke time, diastolic time, and the time delay between the systolic and diastolic peaks, as described in Samria, Rohan, et al. "Non-invasive cuffless estimation of blood pressure using Photoplethysmography without electrocardiograph measurement." 2014 IEEE REGION 10 SYMPOSIUM. IEEE, 2014.

In another embodiment, at least some of the feature values generated based on the iPPG signal may be derived from another analysis approach to PPG waveforms, as described in US Patent Application US20180206733, entitled "Device, method and system for monitoring and management of changes in hemodynamic parameters". This approach assumes the cardiac waveform has the following structure: a minimum/starting point (A), which increases to a systolic peak (B), which decreases to a dicrotic notch (C), which increases to a dicrotic wave (D), which decreases to the starting point of the next pulse wave (E). Various features that may be calculated by the computer 340, which are suggested in the aforementioned publication, include: value of A, value of B, value of C, value of D, value of E, systol area that is the area under ABCE, diastol area that is the area under CDE, and the ratio between BC and DC.

In still another embodiment, the computer 340 may utilize the various approaches described in Elgendi, M. (2012), "On the analysis of fingertip photoplethysmogram signals", Current cardiology reviews, 8(1), 14-25, in order to generate at least some of the feature values bases on the iPPG signal. This reference surveys several preprocessing approaches for PPG signals as well as a variety of feature values that may be utilized. Some of the techniques described therein, which may be utilized by the computer 340, include calculating feature values based on first and second derivatives of PPG signals.

In some embodiments, at least some of the feature values may represent calibration values of a user, which are values of certain parameters such as waveform properties described above when the user had a known state (e.g., while it was known that the user was without a fever and/or sober).

In some embodiments, the computer 340 may utilize one or more feature values indicative of the user's heart rate. Optionally, these feature values may be derived from images from among the images 333, e.g., by performing calculations on iPPG signals extracted from the images. In one example, a time series signal is generated from video images of a subject's exposed skin, and a reference signal is used to perform a constrained source separation (which is a variant of ICA) on the time series signals to obtain the PPG signal; peak-to-peak pulse points are detected in the PPG signal, which may be analyzed to determine parameters such as heart rate, heart rate variability, and/or to obtain peak-to-peak pulse dynamics.

In some embodiments, one or more of the feature values utilized by the computer 340 to calculate a value indicative of whether the user has a fever and/or is intoxicated may be generated based on additional inputs from sources other than the cameras 332.

Stress is a factor that can influence the diameter of the arteries, and thus influence the blood flow and resulting hemoglobin concentration patterns. In one embodiment, the computer 340 is further configured to: receive a value indicative of a stress level of the user, and generate at least one of the feature values based on the received value. Optionally, the value indicative of the stress level is obtained using a thermal camera. In one example, the system may include an inward-facing head-mounted thermal camera configured to take measurements of a periorbital region of the user, where the measurements of a periorbital region of the user are indicative of the stress level of the user. In another example, the system includes an inward-facing head-mounted thermal camera configured to take measurements of a region on the forehead of the user, where the measurements of the region on the forehead of the user are indicative of the stress level of the user. In still another example, the system includes an inward-facing head-mounted thermal camera configured to take measurements of a region on the nose of the user, where the measurements of the region on the nose of the user are indicative of the stress level of the user.

Hydration is a factor that affects blood viscosity, which can affect the speed at which blood flows in the body, and consequently may affect blood flow and hemoglobin concentration patterns. In one embodiment, the computer 340 is further configured to: receive a value indicative of a hydration level of the user, and generate at least one of the feature values based on the received value. Optionally, the system includes an additional camera configured to detect intensity of radiation that is reflected from a region of exposed skin of the user, where the radiation is in spectral wavelengths chosen to be preferentially absorbed by tissue water. In one example, said wavelengths are chosen from three primary bands of wavelengths of approximately 1100-1350 nm, approximately 1500-1800 nm, and approximately 2000-2300 nm. Optionally, measurements of the additional camera are utilized by the computer 340 as values indicative of the hydration level of the user.

Momentary physical activity can affect the blood flow of the user (e.g., due to the increase in the heart rate that it involves). In order to account for this factor, in some embodiments, the computer 340 may generate one or more feature values representing the extent of the user's movement from measurements of the IMU 342.

The user's skin temperature may affect blood viscosity, thus it may influence facial hemoglobin concentration patterns. Some embodiments may include the skin temperature sensor 343, which may be a head-mounted sensor. The skin temperature sensor 343 measures temperature of a region comprising skin on the user's head ($T_{skin}$). Optionally, the computer 340 generates one or more feature values based on $T_{skin}$, such as feature values indicating average skin temperature or a difference from baseline skin temperature.

The temperature and/or humidity in the environment may also be a factor that is considered in some embodiments. The temperature and/or humidity level in the environment can both impact the user's skin temperature and cause a physiologic response involved in regulating the user's body temperature, which may affect observed hemoglobin concentration patterns. Some embodiments may include the environment sensor 344, which may optionally, be head-mounted (e.g., physically coupled to smartglasses). The environment sensor 344 measures an environmental temperature and/or humidity. In one embodiment, the computer 340 may generate one or more feature values based on the temperature and/or humidity in the environment, such as feature values indicating average environment temperature and/or humidity, maximal environment temperature and/or humidity, or a difference from baseline environment temperature and/or humidity.

Training the model 346 may involve utilization of various training algorithms known in the art (e.g., algorithms for training neural networks, and/or other approaches described herein). After the model 346 is trained, feature values may be generated for certain measurements of the user (e.g., current images and baseline images), for which the value of the corresponding label (e.g., whether the user has a fever and/or whether the user is intoxicated) is unknown. The computer 340 can utilize the model 346 to calculate a value indicative of whether the user has a fever and/or whether the user is intoxicated, based on these feature values.

In some embodiments, the model 346 may be generated based on data that includes measurements of the user (i.e., data that includes images taken by the cameras 332). Additionally or alternatively, in some embodiments, the model 346 may be generated based on data that includes measurements of one or more other users (such as users of different ages, weights, sexes, body masses, and health states). In order to achieve a robust model, which may be useful for detecting fever and/or intoxication in various conditions, in some embodiments, the samples used to train the model 346 may include samples based on measurements taken in different conditions. Optionally, the samples are generated based on measurements taken on different days, while in different locations, and/or while different environmental conditions persisted. In a first example, the model 346 is trained on samples generated from a first set of measurements taken while the user was indoors and not in direct sunlight, and is also trained on other samples generated from a second set of measurements taken while the user was outdoors, in direct sunlight. In a second example, the model 346 is trained on samples generated from a first set of measurements taken during daytime, and is also trained on other samples generated from a second set of measurements taken during nighttime. In a third example, the model 346 is trained on samples generated from a first set of measurements taken while the user was moving, and is also trained on other samples generated from a second set of measurements taken while the user was sitting.

Utilizing the model 346 to detect whether the user has a fever and/or whether the user is intoxicated may involve computer 340 performing various operations, depending on the type of model. The following are some examples of various possibilities for the model 346 and the type of calculations that may be accordingly performed by the computer 340, in some embodiments, in order to detect whether the user has a fever and/or whether the user is intoxicated: (a) the model 346 comprises parameters of a decision tree. Optionally, the computer 340 simulates a traversal along a path in the decision tree, determining which branches to take based on the feature values. A value indicative of whether the user has a fever and/or whether the user is intoxicated may be obtained at the leaf node and/or based on calculations involving values on nodes and/or edges along the path; (b) the model 346 comprises parameters of a regression model (e.g., regression coefficients in a linear regression model or a logistic regression model). Optionally, the computer 340 multiplies the feature values (which may be considered a regressor) with the parameters of the regression model in order to obtain the value indicative of whether the user has a fever and/or whether the user is intoxicated; and/or (c) the model 346 comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer 340 provides the feature values as inputs to the neural network, computes the values of the various activation functions and propagates values between layers, and obtains an output from the network, which is the value indicative of whether the user has a fever and/or whether the user is intoxicated.

In some embodiments, a machine learning approach that may be applied to calculating a value indicative of whether the user has a fever and/or whether the user is intoxicated based on images may be characterized as "deep learning". In one embodiment, the model 346 may include parameters describing multiple hidden layers of a neural network. Optionally, the model may include a convolution neural network (CNN). In one example, the CNN may be utilized to identify certain patterns in the video images, such as hemoglobin concentration patterns. Due to the fact that calculations are performed on sequences images display a certain pattern of change over time (i.e., across multiple frames), these calculations may involve retaining state information that is based on previous images in the sequence. Optionally, the model may include parameters that describe an architecture that supports such a capability. In one example, the model may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In addition to detecting whether the user has a fever and/or whether the user is intoxicated, in some embodiments, the computer 340 may utilize the images 333 to detect additional physiological signals and/or conditions.

In one embodiment, the computer 340 calculates, based on the current set of images, a current heart rate and/or a current respiration rate of the user. For example, the computer 340 may utilize one or more techniques described herein or known in the art for calculating heart rate and/or respiration from iPPG signals. The computer 340 can then utilize the current heart rate and/or the current respiration rate of the user, to detect whether the user has a fever, and other conditions such as hyperthermia or hypothermia, also based on deviations of the current heart rate and/or the current respiration rate from a baseline heart rate and/or baseline respiration rate of the user, respectively. In one example, the computer 340 may utilize a machine learning approach similar to the one described above, but instead of using the model 346, the computer 340 uses a different model trained with labels corresponding to extents of hyperthermia or hypothermia (using feature values similar to the ones described above with respect to the model 346).

In another embodiment, the computer 340 may utilize one or more calibration measurements of the user's core body temperature, taken by a different device (e.g., a thermometer), prior to a certain time, to calculate the user's core body temperature based on a certain set of images that were taken by the cameras 332 after the certain time. For example, the computer 340 may utilize a model trained similarly to the model 346, but also includes feature values describing patterns observed for known core body temperatures. In another example, the calibration measurements can be used to adjust values predicted by the computer 340 when making estimations of the extent of fever using the model 346.

In one embodiment, the computer 340 calculates the user's core body temperature based on the deviation of the current pattern from the baseline pattern. For example, in this embodiment, the model 346 is trained with labels that are indicative of the user's core body temperature.

In yet another embodiment, the computer 340 may detect blushing based on the deviation of the current pattern from the baseline pattern. In one example, the computer 340 may utilize a machine learning approach similar to the one described above, but instead of using the model 346, the computer 340 uses a different model trained with labels corresponding to extents of blushing by the user. In this example, blushing may be identified using image analysis techniques known in the art.

The user interface 348 may be utilized to present values calculated by the computer 340, such as indications whether the user has a fever or whether the user is intoxicated. Optionally, the user interface 348 is a component of a device of the user, such as a smartphone's screen or an augmented reality display.

In one embodiment, the computer 340 detects blushing based on the deviation of the current pattern from the baseline pattern, and presents an alert to the user about the blushing via the user interface 348. In one example, the computer 340 provides a biofeedback for the user to enable the user to learn to control the blushing. Optionally, the biofeedback updates the user about the level of blushing in real time, and by that increases the awareness of the user to the blushing and gradually enables the user to learn to control his/her blushing.

In another embodiment, the computer 340 enables the user to share an intoxication history of the user, upon receiving a permission from the user. For example, the user may be able to decide to share his/her intoxication history with a certain person in order to increase the trust, or not share his/her intoxication history with the certain person if the certain persons does not share in return his/her intoxication history with the user.

The following is an additional embodiment of a system configured to detect alcohol intoxication. This embodiment includes memory, a communication interface, and a processor. The processor is configured to: receive baseline images of a user's face, captured by a video camera while the user was sober; calculate, based on the baseline images, a baseline hemoglobin concentration pattern comprising at least 3 points indicative of hemoglobin concentrations on the user's face; receive current images of the user; calculate, based on the current images, a current hemoglobin concentration pattern comprising the at least 3 points indicative of hemoglobin concentrations on the user's face; and detect whether the user is intoxicated based on a deviation of the current hemoglobin concentration pattern from the baseline hemoglobin concentration pattern. Optionally, the video camera is an inward-facing head-mounted camera (HCAM) that is mounted more than 5 mm away from the user's head and is sensitive to wavelengths below 1050 nanometer.

The following method for detecting fever may be used by systems modeled according to FIG. 1c. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, receiving, from first and second inward-facing head-mounted cameras ($Cam_{1\&2}$) sensitive to wavelengths below 1050 nanometer, images of respective first and second regions on a user's face. Optionally, the middles of the first and second regions are at least 4 cm apart.

In Step 2, calculating, based on baseline images captured with $Cam_{1\&2}$ while the user did not have a fever, a baseline pattern comprising values indicative of first and second baseline hemoglobin concentrations at the first and second regions, respectively.

In Step 3, calculating, based on a current set of images captured with $Cam_{1\&2}$, a current pattern comprising values indicative of first and second current hemoglobin concentrations at the first and second regions, respectively.

And in Step 4, detecting whether the user has a fever based on a deviation of the current pattern from the baseline pattern.

In one embodiment, the method for detecting fever optionally includes the following steps: calculating, based on additional baseline images captured with $Cam_{1\&2}$ while the user had a fever, a fever-baseline pattern comprising values indicative of first and second fever hemoglobin concentrations at the first and second regions, respectively; and basing the detecting of whether the user has the fever also on a deviation of the current pattern from the fever-baseline pattern.

In one embodiment, the baseline images and the current set of images comprise a first channel corresponding to wavelengths that are mostly below 580 nanometers and a second channel corresponding to wavelengths mostly above 580 nanometers; the baseline pattern comprises: (i) first values, derived based on the first channel in the baseline images, which are indicative of the first and second baseline hemoglobin concentrations at the first and second regions, respectively, and (ii) second values, derived based on the second channel in the baseline images, which are indicative of third and fourth baseline hemoglobin concentrations at the first and second regions, respectively. The current pattern comprises: (i) third values, derived based on the first channel in the current set of images, which are indicative of the first and second current hemoglobin concentrations at the first and second regions, respectively, and (ii) fourth values, derived based on the second channel in the current set of images, which are indicative of third and fourth current hemoglobin concentrations at the first and second regions, respectively. Optionally, method for detecting fever includes a step of calculating a confidence in a detection of the fever based on the deviation of the current pattern from the baseline pattern, such that the confidence decreases as the difference between the third values and the fourth values increases.

FIG. 2a illustrates an embodiment of a system that utilizes multiple PPG signals, measured using different types of sensors, to detect a physiological response. In one embodiment, the system includes at least a head-mounted contact PPG device 782, a camera 784, and a computer 780.

In one embodiment, the head-mounted contact PPG device 782 (also referred to as PPG device 782) measures a signal indicative of a PPG signal 783 at a first region of interest ($ROI_1$) on a user's body (also referred to as PPG signal 783). $ROI_1$ includes a region of exposed skin on the user's head, and the PPG device 782 includes one or more light sources configured to illuminate $ROI_1$. For example, the one or more light sources may include light emitting diodes (LEDs) that illuminate $ROI_1$. Optionally, the one or more LEDs include at least two LEDs, wherein each illuminates $ROI_1$ with light at a different wavelength. In one example, the at least two LEDs include a first LED that illuminates $ROI_1$ with green light and a second LED that illuminates $ROI_1$ with an infrared light. Optionally, the PPG device 782 includes one or more photodetectors configured to detect extents of reflections from $ROI_1$.

The camera 784 captures images 785 of a second region of interest ($ROI_2$) on the user's head. The camera is located more than 10 mm away from the user's head. Optionally, the camera is located more than 20 mm away from the user's head. Optionally, the camera 784 is a head-mounted camera. In some embodiments, the camera 784 may utilize a light source to illuminate $ROI_2$. Optionally, the light source is configured to illuminate at least a portion of $ROI_2$, and the camera 784 is located more than 15 cm away from the user's head.

In another embodiment, the system illustrated in FIG. 2a does not include a light source that illuminates $ROI_2$ and the camera 784 may be considered a "passive" camera.

In some embodiments, the camera 784 is not head-mounted. Optionally, the images 785 taken by the non-head mounted camera are synchronized with the PPG signal 783 (e.g., based on synchronizing the clocks of the PPG device 782 and the camera 784, and/or based on time stamps added by the PPG device 782 and time stamps added by the camera 784). Optionally, the system achieves data synchronization that is better than 35 milliseconds between the PPG signal and the iPPG signals. Optionally, the system achieves data synchronization better than 1 millisecond between the PPG signal and the iPPG signals. Examples of cameras that are not head-mounted, which may be synchronized with the head-mounted PPG device 782 include: a smartphone camera, a tablet camera, a laptop camera, and/or webcam.

In some embodiments, references to the camera 784 involve more than one camera. Optionally, the camera 784 may refer to two or more inward-facing head-mounted cameras, and $ROI_2$ includes two or more regions on the user's head that are respectively captured by the two or more inward-facing head-mounted cameras. Optionally, the two or more regions include regions on different sides of the user's head.

Optionally, $ROI_2$ covers a larger area of exposed skin than $ROI_1$. In one example, the area of $ROI_2$ is at least ten times larger than the area of $ROI_1$. In one example, the PPG device 782 does not obstruct the field of view of the camera 784 to $ROI_2$.

In some embodiments, various devices, such as the PPG device 782, the camera 784, and/or the computer 780, may be physically coupled to a frame of smartglasses or to a smart-helmet, which is designed to measure the user in day-to-day activities, over a duration of weeks, months, and/or years. FIG. 2b and FIG. 2c illustrate smartglasses that may be utilized to realize the invention described herein.

FIG. 2b illustrates smartglasses that include camera 796 and several contact PPG devices. The contact PPG devices correspond to the PPG device 782 and are used to measure the PPG signal 783. The contact PPG devices may be coupled at various locations on the frame 794, and thus may come in contact with various regions on the user's head. For example, contact PPG device 791a is located on the right temple tip, which brings it to contact with a region behind the user's ear (when the user wears the smartglasses). Contact PPG device 791b is located on the right temple of the frame 794, which puts it in contact with a region on the user's right temple (when wearing the smartglasses). It is to be noted that in some embodiments, in order to bring the contact PPG device close such that it touches the skin, various apparatuses may be utilized, such as spacers (e.g., made from rubber or plastic), and/or adjustable inserts that can help bridge a possible gap between the frame's temple and the user's face. Such an apparatus is spacer 792 which brings contact PPG device 791*b* in contact with the user's temple when the user wears the smartglasses. Another possible location for a contact PPG device is the nose bridge, as contact PPG device 791*c* is illustrated in the figure. It is to be noted the contact PPG device 791*c* may be embedded in the nose bridge (or one of its components), and/or physically coupled to a part of the nose bridge.

FIG. 2*c* illustrates smartglasses that include at least first, second, and third inward-facing cameras, each of which may correspond to the camera 784. The figure illustrates a frame 797 to which a first inward-facing camera 795*a* is coupled above the lens that is in front of the right eye, and a second inward-facing camera 795*b* that is coupled to the frame 797 above the lens that is in front of the left eye. The figure also illustrates a third inward facing camera 795*c* that is on the left side of the frame 797 and configured to capture images of lower portions of the user's face (e.g., portions of the left cheek).

The computer 780 is configured, in some embodiments, to detect a physiological response based on: (i) imaging photoplethysmogram signals (iPPG signals) recognizable in the images 785, and (ii) correlations between the PPG signal 783 and the iPPG signals. Some examples of physiological responses that may be detected include: an allergic reaction, a stroke, a migraine, stress, a certain emotional response, pain, and blood pressure (i.e., calculating the blood pressure value). Optionally, the computer 780 forwards an indication of a detection of the physiological response 789 to a device of the user and/or to another computer system. Examples of computers that may be utilized to perform this detection are computer 400 or computer 410 illustrated in FIG. 21*a* and FIG. 21*b*, respectively.

Herein, sentences of the form "iPPG signal is recognizable in images" refer to effects of blood volume changes due to pulse waves that may be extracted from a series of images of the region. These changes may manifest as color changes to certain regions (pixels) in the images, and may be identified and/or utilized by a computer (e.g., in order to generate a signal indicative of the blood volume at the region). However, these changes need not necessarily be recognizable to the naked eye (e.g., because of their subtlety, the short duration in which they occur, or involvement of light outside of the visible spectrum). For example, blood flow may cause facial skin color changes (FSCC) that corresponds to different concentrations of oxidized hemoglobin due to varying volume of blood at a certain region due to different stages of a cardiac pulse, and/or the different magnitudes of cardiac output.

Herein, detecting the physiological response may mean detecting that the user is experiencing the physiological response, and/or that there is an onset of the physiological response. In the case of the physiological response being associated with one or more values (e.g., blood pressure), detecting the physiological response may mean calculating the one or more values.

In some embodiments, detecting the physiological response may involve calculating one or more of the following values: an indication of whether or not the user is experiencing the physiological response (e.g., whether or not the user is having a stroke), a value indicative of an extent to which the user is experiencing the physiological response (e.g., a level of pain or stress felt by the user), a duration since the onset of the physiological response (a duration since a migraine has started), and a duration until an onset of the physiological response.

In some embodiments, the computer 780 detects the physiological response utilizing previously taken PPG signals of the user (taken with the PPG device 782) and/or previously taken images (taken with the camera) in which previous iPPG signals are recognizable. Having such previous values can assist the computer 780 to detect changes to blood flow that may be indicative of certain physiological responses. In some embodiments, previously taken PPG signals and/or images are used to generate baseline values representing baseline properties of the user's blood flow. Optionally, calculating the baseline values may be done based on previously taken PPG signals and/or images that were measured at least an hour before taking the PPG signal 783 and/or the images 785. Optionally, calculating the baseline values may be done based on previously taken PPG signals and/or images that were measured at least a day before the PPG signal 783 and/or the images 785. Some examples of baseline values may include baseline physiological signal values (e.g., baseline heart rate, blood pressure, or heart rate variability). Other examples of baseline values may include typical values of fiducial points in PPG signals (e.g., magnitudes of systolic peaks) and/or typical relationships between different fiducial points (e.g., typical distance between systolic peaks and dicrotic notches, and the like).

A baseline value may be calculated in various ways. In a first example, the baseline is a function of the average measurements of the user (which include previously taken PPG signals and/or iPPG signals recognizable in previously taken images described above). In a second example, the baseline value may be a function of the situation the user is in, such that previous measurements taken during similar situations are weighted higher than previous measurements taken during less similar situations. A PPG signal may show different characteristics in different situations because of the different mental and/or physiological states of the user in the different situations. As a result, a situation-dependent baseline can improve the accuracy of detecting the physiological response. In a third example, the baseline value may be a function of an intake of some substances (such as food, beverage, medications, and/or drugs), such that previous measurements taken after consuming similar substances are weighted higher than previous measurements taken after not consuming the similar substances, and/or after consuming less similar substances. A PPG signal may show different characteristics after the user consumes different substances because of the different mental and/or physiological states the user may enter after consuming the substances, especially when the substances include things such as medications, drugs, alcohol, and/or certain types of food. As a result, a substance-dependent baseline can improve the accuracy of detecting the physiological response.

There are various ways in which the computer 780 may utilize correlations between the PPG signal 783 and the iPPG signals to detect the physiological response. In some embodiments, the computer 780 may rely on the fact that due to the proximity of $ROI_1$ and $ROI_2$ (both being on the head and consequently, close by) the appearances of pulse waves at the different ROIs is highly correlated. This fact may be utilized by the computer 780 to identify fiducial points in the PPG signal 783, which is often a strong signal, and then to identify the corresponding fiducial points in the correlated iPPG signals (that are noisier than the PPG signal). Additionally or alternatively, when a using machine learning-based approach, at least some of the feature values used by the computer 780 may reflect values related to correlations between the PPG signal 783 and the iPPG signals (e.g., values of similarity and/or offsets between the PPG signal 783 and the iPPG signals). Both uses of correlations are elaborated on further below.

It is to be noted that because the PPG device 782 touches and occludes $ROI_1$, while the camera 784 does not occlude $ROI_2$, the PPG signal 783 extracted from the PPG device 782 usually has a much better signal-to-noise (SNR) compared to the iPPG signals extracted from the images 785 of $ROI_2$. In addition, due to the shorter distance between the PPG device 782 and $ROI_1$, and especially in embodiments where the camera 784 is a passive camera (i.e., does not include a light source to illuminate ROI), the PPG signal 783 will typically suffer much less from illumination changes compared to the iPPG signals.

Furthermore, because both $ROI_1$ and $ROI_2$ are on the user's head, and because the PPG device 782 and the camera 784 measure the user essentially simultaneously, manifestation of the pulse arrival in the PPG signal 783 and the iPPG signals are typically highly correlated (e.g., the signals exhibit highly correlated pulse arrival times). This correlation enables the computer 780 to utilize pulse fiducial points identified in the PPG signal 783 (which is less noisy than the iPPG signals) to extract information from iPPG signals more efficiently and accurately.

In one embodiment, the computer 780 extracts from the PPG signal 783 one or more values that may serve as a basis to correlate between the PPG signal 783 and the iPPG signals. Optionally, the extracted values are indicative of one or more of the following PPG waveform fiducial points: a systolic peak, a dicrotic notch, a diastolic peak. Optionally, the extracted values may be indicative of a timing of a certain fiducial point (i.e., when it manifests in the PPG signal 783), and/or the magnitude of the PPG signal 783 at the time corresponding to the certain fiducial point. Additionally or alternatively, the extracted values may be indicative of other waveform properties such as an interbeat interval, and a systolic-diastolic peak-to-peak time.

Due to the camera 784 not being in contact with $ROI_2$, it is often the case that direct identification of the fiducial points in the iPPG signals may be difficult, e.g., due to the excessive noise in the signal because of movements and ambient light. Knowing an identification of fiducial points in the PPG signal 783, such as times of systolic peaks, dicrotic notches, and diastolic peaks, provides useful information for determining when these events are to be expected to manifest in the iPPG signals. The timings of the occurrences of these fiducial points in the PPG signal 783 can serve as a basis according to which fiducial points can be determined in the iPPG signals.

In one embodiment, times corresponding to fiducial points, as determined based on the PPG signal 783, are also used for fiducial points in the iPPG signals. Thus, the magnitudes of the fiducial points in the iPPG signals are taken essentially at the same times of the fiducial points in the PPG signal 783. Such an approach can be especially accurate when $ROI_1$ and $ROI_2$ are close to each other, thus it is likely that manifestation of pulse waves occurs at very similar times in $ROI_1$ and $ROI_2$, so when, for example, there is a systolic peak in the PPG signal 863, there is also one approximately at the same time in the iPPG signals.

In another embodiment, times corresponding to fiducial points, as determined based on the PPG signal 783, may also be used to determine fiducial points in the iPPG signals, by applying a certain offset to the times. This certain offset may be used to account for the difference between the distances/ route blood travels in order to reach $ROI_2$ as opposed to the distance/route blood travels in order to reach $ROI_1$.

In one example, an offset used between when a fiducial point (e.g., a systolic peak) occurs in the PPG signal 783, and when it manifests in each of the iPPG signals may be a fixed offset (e.g., an offset that is a function of the relative location of $ROI_2$ from $ROI_1$). In another example, different sub-regions of $ROI_2$ (e.g., corresponding to different pixels in the images 785) may have different offsets that are calculated empirically relative to the timings of the PPG signal. In still another example, the iPPG signals are extracted from the images based on values of time-segments in which the iPPG signals were expected to appear as a function of the locations of respective regions of the iPPG signals relative to the location of the contact PPG device.

An offset used between when a fiducial point (e.g., a systolic peak) occurs in the PPG signal 783, and when it manifests in in each of the iPPG signals may be adjusted to account for blood velocity. For example, the offset may be inversely proportional to the heart rate and/or blood pressure determined from the PPG signal 783. When the heart rate and/or blood pressure increase, this is usually correlated with a higher velocity of blood flow, which will tend to reduce the difference in manifestations of a pulse wave in $ROI_1$ and $ROI_2$.

It is to be noted that offsets used between times of fiducial points identified in the PPG signal 783 and the iPPG signals may be user-specific and learned overtime. For example, histograms of the offsets between the maxima in the PPG signal 783 and the maxima of each of the iPPG signals, as observed over multiple pulses of the user, can be aggregated. Based on these histograms, the most frequent offset can be used to represent the difference between when systolic peaks occur in the PPG signal 783 and when it manifests in each of the iPPG signals.

In another embodiment, times corresponding to fiducial points, as determined based on the PPG signal 783, may be used to set a range of times during which the same fiducial point is expected to manifest in an iPPG signal (from among the iPPG signals). For example, if a systolic peak is observed at time t in the PPG signal 783, a manifestation of a systolic peak will be extracted from a time that falls in [t+a, t+b], where a<b, and the values of a and b are set to correspond to the minimum and maximum offsets between manifestations of systolic peaks in $ROI_1$ and a sub-region of $ROI_2$ to which the iPPG signal corresponds. As discussed above, the values a and b may also be adjusted according to values such as the heart rate and/or blood pressure, and may also be learned for a specific user.

In some embodiments, the computer 780 may utilize the PPG signal 783 to verify the quality of the iPPG signals. Optionally, the computer 780 may refrain from utilizing iPPG signals in calculations when they exhibit a significant difference from the PPG signal 783. For example, if a heart rate calculated based on the PPG signal 783, during a certain period, is significantly different from a heart rate calculated based on the iPPG signals during that period (e.g., a difference greater than a threshold of ±5 bpm), then that may indicate the iPPG signals during the certain period were noisy and/or unreliable.

Additionally, using the PPG signal 783, as described above, to assess various sub-regions of $ROI_2$, can serve as a quality filter to select which regions of the face should be used to perform detection of physiological responses. If a certain region displays consistently an accurate iPPG signal, it may be more reliable for detection of the physiological response than a region from which an accurate signal cannot be extracted.

Another way to describe the benefit of measuring simultaneously the PPG signal 783 and iPPG signals on the head involves the fact that often the iPPG signals are weak relative to the noise. Therefore, automatic detection of the iPPG signals requires discrimination between true PPG pulses and random fluctuations due to the noise. In one embodiment, an algorithm for the selection of the iPPG pulses is based on the values of time-segments in which the iPPG signals are expected to appear as a function of their location relative to the location of the PPG device 782. Optionally, the detected iPPG signals in these time-segments are identified as iPPG signals if they meet one or more criteria based on (i) the spatial waveform of the iPPG signals relative to the reference PPG signal, (ii) correlation between each iPPG signal in the current time-segment and a predetermined number of neighboring time-segments, and (iii) correlations between iPPG signals extracted from neighboring regions of exposed skin on the head, which are expected to show essentially the same rhythm with a bounded time delay. Optionally, the signals are taken as iPPG signals if minimal values of the criteria are obtained in several time-segments. The minimal values and the number of time-segments can be determined in order to achieve minimal standard deviation of the differences between the values of the heart rate extracted from the noisy iPPG signals and the reference heart rate extracted from the less noisy PPG signal.

In some embodiments, the iPPG signals include multiple values for different sub-regions of $ROI_2$, and the physiological response is detected based on differences between amplitudes of the values recognizable in the different sub-regions of $ROI_2$. For example, each sub-region may be captured by a subset of pixels in the images 785.

In one embodiment, the physiological response is indicative of an allergic reaction, and the sub-regions of $ROI_2$ include portions of at least two of the following areas on the user's face: nose, upper lip, lips, cheeks, temples, periorbital area around the eyes, and the forehead. Optionally, the computer 780 detects the allergic reaction based on changes in blood flow which manifest in iPPG signals corresponding to the at least two areas.

In another embodiment, the physiological response is indicative of a stroke, and the sub-regions of $ROI_2$ include at least one of the following pairs on the user's face: left and right cheeks, left and right temples, left and right sides of the forehead, and left and right sides of the periorbital area around the eyes. Optionally, the computer 780 detects the stroke based on a difference in blood flow on the two sides of the face.

In yet another embodiment, the physiological response is indicative of a migraine, and the sub-regions of $ROI_2$ include at least one of the following pairs on the user's face: left and right sides of the forehead, left and right temples, left and right sides of the periorbital area around the eyes, and left and right cheeks.

In still another embodiment, the physiological response is indicative of a blood pressure value that is calculated based on differences in pulse transit times detectable in the sub-regions of $ROI_2$. Optionally, the sub-regions comprise at least two of the following areas on the user's face: left temple, right temple, left side of the forehead, right side of the forehead, left check, right cheek, nose, periorbital area around the left eye, and periorbital area around the right eye.

And in yet another embodiment, the physiological response is indicative of at least one of stress, emotional response, and pain, which are calculated based on changes to hemoglobin concentrations observable in the iPPG signals relative to previous measurements of hemoglobin concentrations observable in the iPPG signals of the user. Optionally, the sub-regions of $ROI_2$ include at least two of the following areas on the user's face: lips, upper lip, chin, left temple, right temple, left side of the forehead, right side of the forehead, left check, right cheek, left ear lobe, right ear lobe, nose, periorbital area around the left eye, and periorbital area around the right eye.

In one embodiment, the computer 780 is a head-mounted computer. Optionally, detecting the physiological response involves performing at least the following: identifying times at which fiducial points appear in the PPG signal; calculating, based on the times, time-segments in which the fiducial points are expected to appear in imaging photoplethysmogram signals recognizable the images (iPPG signals); and detecting a physiological response based on values of the iPPG signals during the time-segments.

As part of the calculations involved in detecting the physiological response, the computer 780 may perform various filtering and/or processing procedures to the PPG signal 783, the images 785, and/or iPPG signals extracted from the images 785. Some non-limiting examples of the preprocessing include: normalization of pixel intensities (e.g., to obtain a zero-mean unit variance time series signal), and conditioning a time series signal by constructing a square wave, a sine wave, or a user defined shape, such as that obtained from an ECG signal or a PPG signal as described in U.S. Pat. No. 8,617,081.

In some embodiments, the images 785 may undergo various preprocessing to improve the signal, such as color space transformation (e.g., transforming RGB images into a monochromatic color or images in a different color space), blind source separation using algorithms such as independent component analysis (ICA) or principal component analysis (PCA), and various filtering techniques, such as detrending, bandpass filtering, and/or continuous wavelet transform (CWT). Various preprocessing techniques known in the art that may assist in extracting iPPG signals from images are discussed in Zaunseder et al. (2018), "Cardiovascular assessment by imaging photoplethysmography-a review", Biomedical Engineering 63(5), 617-634. An example of preprocessing that may be used in some embodiments is given in U.S. Pat. No. 9,020,185, titled "Systems and methods for non-contact heart rate sensing", which describes how a times-series signals obtained from video of a user can be filtered and processed to separate an underlying pulsing signal by, for example, using an ICA algorithm.

In some embodiments, detection of the physiological response may involve calculation of pulse arrival times (PATs) at $ROI_1$ and/or at one or more sub-regions of $ROI_2$. Optionally, a PAT calculated from an PPG signal represents a time at which the value representing blood volume (in the waveform represented in the PPG) begins to rise (signaling the arrival of the pulse). Alternatively, the PAT may be calculated as a different time, with respect to the pulse waveform, such as the time at which a value representing blood volume reaches a maximum or a certain threshold, or the PAT may be the average of the time the blood volume is above a certain threshold. Another approach that may be utilized to calculate a PAT from an iPPG signal is described in Sola et al. "Parametric estimation of pulse arrival time: a robust approach to pulse wave velocity", Physiological measurement 30.7 (2009): 603, which describe a family of PAT estimators based on the parametric modeling of the anacrotic phase of a pressure pulse.

Detection of the physiological response may involve the computer utilizing an approach that may be characterized as involving machine learning. In some embodiments, such a detection approach may involve the computer generating feature values based on data that includes the PPG signal 783, the images 785, and/or iPPG signals recognizable in the images 785, and optionally other data. Optionally, at least some of the feature values are based on correlations between the PPG signal 783 and the iPPG signals. The computer 780 then utilizes a previously trained model 779 to calculate one or more values indicative of whether, and/or to what extent, the user is experiencing the physiological response (which may be any one of the examples of values mentioned further above as being calculated by the computer 780 for this purpose).

Feature values generated based on PPG signals (e.g., the PPG signal 783 and/or one or more of the iPPG signals extracted from the images 785) may include various types of values, which may be indicative of dynamics of the blood flow at the respective regions to which the PPG signals correspond. Optionally, these feature values may relate to properties of a pulse waveform, which may be a specific pulse waveform (which corresponds to a certain beat of the heart), or a window of pulse waveforms (e.g., an average property of pulse waveforms in a certain window of time).

Some examples of feature values that may be generated based on a pulse waveform include: the area under the pulse waveform, the amplitude of the pulse waveform, a derivative and/or second derivative of the pulse waveform, a pulse waveform shape, pulse waveform energy, and pulse transit time (to the respective ROI). Optionally, some feature values may be derived from fiducial points identified in the PPG signals; these may include values such as magnitudes of the PPG signal at certain fiducial points, time offsets between different fiducial points, and/or other differences between fiducial points. Some examples of fiducial point-based feature values may include one or more of the following: a magnitude of a systolic peak, a magnitude of a diastolic peak, duration of the systolic phase, and duration of the diastolic phase. Additional examples of feature values may include properties of the cardiac activity, such as the heart rate and heart rate variability (as determined from the PPG signal). Additionally, some feature values may include values of other physiological signals that may be calculated based on PPG signals, such as blood pressure and cardiac output.

The aforementioned feature values may be calculated in various ways. In one example, some feature values are calculated for each PPG signal individually. In another example, some feature values are calculated after normalizing a PPG signal with respect to previous measurements from the corresponding PPG device used to measure the PPG signal. In other examples, at least some of the feature values may be calculated based on an aggregation of multiple PPG signals (e.g., different pixels/regions in images captured by an iPPG device), or by aggregating values from multiple contact PPG devices.

In some embodiments, at least some of the feature values may include values indicative of correlations between the PPG signal 783 and iPPG signals extracted from the images 785. In one example, the feature values may include values indicative of offsets between when certain fiducial points appear in the PPG signal 783, and when they appear in each of the iPPG signals. In another example, the feature values may include values indicative of offsets at which the correlation (e.g., as calculated by a dot-product) between the PPG signal 783 and the iPPG signals is maximized. In still another example, the feature values may include values indicative of maximal value of correlation (e.g., as calculated by a dot-product) between the PPG signal 783 and the iPPG signals (when using different offsets).

In some embodiments, at least some of the feature values may represent comparative values, which provide an indication of the difference in blood flow, and/or in some other property that may be derived from a PPG signal, between various regions on the head. Optionally, such feature values may assist in detecting asymmetrical blood flow (and/or changes thereto).

In some embodiments, at least some of the feature values describe properties of pulse waveforms (e.g., various types of feature values mentioned above), which are derived from the previous measurements of the user using the PPG device 782 and/or the camera 784. Optionally, these feature values may include various blood flow baselines for the user, which correspond to a certain situation the user was in when the previous measurements were taken.

In some embodiments, at least some of the feature values may be "raw" or minimally processed measurements of the PPG device 782 and/or the camera 784. Optionally, at least some of the feature values may be pixel values obtained by the camera 864. Optionally, the pixel values may be provided as input to functions in order to generate the feature values that are low-level image-based features. Some examples of low-level features, which may be derived from images, include feature generated using Gabor filters, local binary patterns (LBP) and their derivatives, algorithms such as SIFT and/or SURF (and their derivatives), image keypoints, histograms of oriented gradients (HOG) descriptors, and products of statistical procedures such independent component analysis (ICA), principal component analysis (PCA), or linear discriminant analysis (LDA). Optionally, one or more of the feature values may be derived from multiple images taken at different times, such as volume local binary patterns (VLBP), cuboids, and/or optical strain-based features. In one example, one or more of the feature values may represent a difference between values of pixels at one time t and values of other pixels at a different region at some other time t+x (which, for example, can help detect different arrival times of a pulse wave).

In some embodiments, at least some feature values may be generated based on other data sources (in addition to PPG signals). In some examples, at least some feature values may be generated based on other sensors, such as movement sensors (which may be head-mounted, wrist-worn, or carried by the user some other way), head-mounted thermal cameras, or other sensors used to measure the user. In other examples, at least some feature values may be indicative of environmental conditions, such as the temperature, humidity, and/or extent of illumination (e.g., as obtained utilizing an outward-facing head-mounted camera). Additionally, some feature values may be indicative of physical characteristics of the user, such as age, sex, weight, Body Mass Index (BMI), skin tone, and other characteristics and/or situations the user may be in (e.g., level of tiredness, consumptions of various substances, etc.)

Stress is a factor that can influence the diameter of the arteries, and thus influence calculated values that relate to the PPG signals and/or blood flow. In one embodiment, the computer 780 receives a value indicative of a stress level of the user, and generates at least one of the feature values based on the received value. Optionally, the value indicative of the stress level is obtained using a thermal camera. In one example, the system may include an inward-facing head-mounted thermal camera that takes measurements of a periorbital region of the user, where the measurements of a periorbital region of the user are indicative of the stress level of the user. In another example, the system includes an inward-facing head-mounted thermal camera that takes measurements of a region on the forehead of the user, where the measurements of the region on the forehead of the user are indicative of the stress level of the user. In still another example, the system includes an inward-facing head-mounted thermal camera that takes measurements of a region on the nose of the user, where the measurements of the region on the nose of the user are indicative of the stress level of the user.

Hydration is a factor that affects blood viscosity, which can affect the speed at which the blood flows in the body. In one embodiment, the computer 780 receives a value indicative of a hydration level of the user, and generates at least one of the feature values based on the received value. Optionally, the system includes an additional camera that detects intensity of radiation that is reflected from a region of exposed skin of the user, where the radiation is in spectral wavelengths chosen to be preferentially absorbed by tissue water. In one example, said wavelengths are chosen from three primary bands of wavelengths of approximately 1100-1350 nm, approximately 1500-1800 nm, and approximately 2000-2300 nm. Optionally, measurements of the additional camera are utilized by the computer as values indicative of the hydration level of the user.

The following are examples of embodiments that utilize additional inputs to generate feature values used to detect the physiological response. In one embodiment, the computer 780 receives a value indicative of a temperature of the user's body, and generates at least one of the feature values based on the received value. In another embodiment, the computer 780 receives a value indicative of a movement of the user's body, and generates at least one of the feature values based on the received value. For example, the computer 780 may receive the input form a head-mounted Inertial Measurement Unit (IMU 778) that includes a combination of accelerometers, gyroscopes, and optionally magnetometers, and/or an IMU in a mobile device carried by the user. In yet another embodiment, the computer 780 receives a value indicative of an orientation of the user's head, and generates at least one of the feature values based on the received value. For example, the computer 780 may receive the values indicative of the head's orientation from an outward-facing head-mounted camera, and/or from a nearby non-wearable video camera. In still another embodiment, the computer 780 receives a value indicative of consumption of a substance by the user, and generates at least one of the feature values based on the received value. Optionally, the substance comprises a vasodilator and/or a vasoconstrictor.

The model 779 utilized to detect the physiological response may be generated, in some embodiments, based on data obtained from one or more users. In the case where the physiological response is a certain medical condition (e.g., an allergic reaction and/or a migraine), at least some of the data used to train the model 779 corresponds to times in which the one or more users were not affected by the physiological response, and additional data used to train the model was obtained while the physiological response occurred and/or following that time. Thus, this training data may reflect PPG signals and/or blood flow both at normal times, and changes to PPG signals and/or blood flow that may ensue due to the physiological response. In the case where the physiological response corresponds to a value of a physiological signal (e.g., blood pressure), data used to train the model 779 may include measurements of the one or more users that are associated with a reference value for the physiological signal (e.g., the reference values may be blood pressure values measured by an external device).

The aforementioned training data may be used to generate samples, each sample including feature values generated based on PPG signals of a certain user, additional optional data (as described above), and a label. The PPG signals include measurements of the certain user (e.g., taken with the PPG device 782 and the camera 784) at a certain time, and optionally previous measurements of the user taken before the certain time. The label is a value related to the physiological response (e.g., an indication of the extent of the physiological response). For example, the label may be indicative of whether the user, at the certain time, experienced a certain physiological response (e.g., an allergic reaction or a stroke). In another example, the label may be indicative of the extent or severity of the physiological response at the certain time. In yet another example, the label may be indicative of the duration until an onset of the physiological response. In still another example, the label may be indicative of the duration that has elapsed since the onset of the physiological response.

In some embodiments, the model 779 used by the computer 780 to detect the physiological response of a specific user may be generated, at least in part, based on data that includes previous measurements of the specific user (and as such, may be considered personalized to some extent for the specific user). Additionally or alternatively, in some embodiments, the model 779 may be generated based on data of other users. Optionally, the data used to train the model 779 may include data obtained from a diverse set of users (e.g., users of different ages, weights, sexes, preexisting medical conditions, etc.). Optionally, the data used to train the model 779 includes data of other users with similar characteristics to the specific user (e.g., similar weight, age, sex, height, and/or preexisting condition).

In order to achieve a robust model, which may be useful for detecting the physiological response for a diverse set of conditions, in some embodiments, the samples used for the training of the model 779 may include samples based on data collected when users were in different conditions. Optionally, the samples are generated based on data collected on different days, while indoors and outdoors, and while different environmental conditions persisted. In one example, the model 779 is trained on samples generated from a first set of training data taken during daytime, and is also trained on other samples generated from a second set of training data taken during nighttime. In a second example, the model 779 is trained on samples generated from a first set of training data taken while users were exercising and moving, and is also trained on other samples generated from a second set of data taken while users were sitting and not exercising.

Utilizing the model 779 to detect the physiological response may involve the computer 780 performing various operations, depending on the type of model. The following are some examples of various possibilities for the model 779 and the type of calculations that may be accordingly performed by the computer 780, in some embodiments, in order to calculate a certain value indicative of an extent of the physiological response experienced by the user: (a) the model 779 comprises parameters of a decision tree. Optionally, the computer 780 simulates a traversal along a path in the decision tree, determining which branches to take based on the feature values. The certain value may be obtained at the leaf node and/or based on calculations involving values on nodes and/or edges along the path; (b) the model 779 comprises parameters of a regression model (e.g., regression coefficients in a linear regression model or a logistic regression model). Optionally, the computer 780 multiplies the feature values (which may be considered a regressor) with the parameters of the regression model in order to obtain the certain value; and/or (c) the model 779 comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer 780 provides the feature values as inputs to the neural network, computes the values of the various activation functions and propagates values between layers, and obtains an output from the network, which is the certain value In some embodiments, a machine learning approach that may be applied to calculating a value indicative of the extent of the physiological response experienced by the user may be characterized as "deep learning". In one embodiment, the model 779 may include parameters describing multiple hidden layers of a neural network. Optionally, the model 779 may include a convolution neural network (CNN). In one example, the CNN may be utilized to identify certain patterns in the images 785, such as the patterns of corresponding to blood volume effects and ballistocardiographic effects of the cardiac pulse. Due to the fact that calculating the value indicative of the extent of the physiological response may be based on multiple, possibly successive, images that display a certain pattern of change over time (i.e., across multiple frames), these calculations may involve retaining state information that is based on previous images. Optionally, the model 779 may include parameters that describe an architecture that supports such a capability. In one example, the model 779 may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LS™) architecture. In another example, the RNN may be implemented using a bidirectional recurrent neural network architecture (BRNN).

In some embodiments, the system illustrated in FIG. 2a may optionally include a head-mounted sensor 788 configured to measure a signal indicative of timing of the user's inhalation phase and/or exhalation phase (respiratory-phase signal). Optionally, the computer 780 may utilize the respiratory-phase signal to detect the physiological response. For example, the computer 780 may utilize correlations between timings of fiducial points of the iPPG signals and the respiratory-phase signal. Optionally, at least some of the feature values generated by the computer 780 (when the detection of the physiological response involves a machine learning-based approach) may be generated based on the respiratory-phase signal. For example, the feature values may include values indicating whether a certain fiducial point occurred while the user was inhaling or exhaling. The head-mounted sensor 788 used to measure the respiratory-phase signal may include one or more of the following sensors: (i) an inward-facing camera configured to take video in which movements of the nostrils and/or lips are indicative of the respiratory-phase signal, (ii) an inward-facing thermal camera configured to measure temperatures of the upper lip and/or the mouth, which are indicative of the respiratory-phase signal, and (iii) an acoustic sensor configured to record sound waves that are indicative of the respiratory-phase signal.

In addition to detecting a physiological response, the system illustrated in FIG. 2a may be utilized to authenticate the user. In one embodiment, the camera 784 is integrated in a non-wearable device (e.g., a smartphone or a tablet computer), and the computer 780 may authenticate the identity of the user and determine that the user is using the non-wearable device by checking whether correlations between the PPG signal and the iPPG signals reaches a predetermined threshold. Optionally, the predetermined threshold indicates, above a predetermined certainty, that the PPG signal 783 and the images 785 (in which the iPPG signals are recognizable) belong to the same person.

The following method for detecting physiological response may be used by systems modeled according to FIG. 2a. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, measuring a signal indicative of a PPG signal at a first region that includes exposed skin on a user's head (referred to as a PPG signal) utilizing a head-mounted contact PPG device. In one example, the head-mounted contact PPG device is the PPG device 782.

In Step 2, capturing images of a second region that includes exposed skin on the user's head utilizing a camera. Optionally, the camera is located more than 10 mm away from the user's head. Optionally, the camera used in this step is the camera 784.

And in Step 3, detecting a physiological response based on: (i) imaging photoplethysmogram signals (iPPG signals) recognizable in the images, and (ii) correlations between the PPG signal and the iPPG signals.

In some embodiments, detecting the physiological response is done utilizing a machine learning-based approach. Optionally, the method includes the following steps: generating feature values based on data that includes: (i) the iPPG signals, and (ii) correlations between the PPG signal and the iPPG signals; and utilizing a model to calculate, based on the feature values, a value indicative of the extent of the physiological response experienced by the user.

In one embodiment, the physiological response is indicative of a value of blood pressure, and is calculated based on differences in pulse transit times detectable in iPPG signals of sub-regions of the second region. Optionally, the sub-regions include at least two of the following areas on the user's face: left temple, right temple, left side of the forehead, right side of the forehead, left cheek, right cheek, nose, periorbital area around the left eye, and periorbital area around the right eye.

In another embodiment, the physiological response is indicative of at least one of stress, an emotional response, and pain, which are calculated based on changes to hemoglobin concentrations observable in the iPPG signals relative to previous measurements of hemoglobin concentrations observable in the iPPG signals of the user. Optionally, the sub-regions comprise at least two of the following areas on the user's face: lips, upper lip, chin, left temple, right temple, left side of the forehead, right side of the forehead, left check, right cheek, left ear lobe, right ear lobe, nose, periorbital area around the left eye, and periorbital area around the right eye.

In one embodiment, a low-power head-mounted iPPG system includes: (i) a head-mounted contact PPG device configured to measure a signal indicative of a PPG signal at a first region comprising exposed skin on a user's head (PPG signal), (ii) a head-mounted camera configured to capture images of a second region comprising exposed skin on the user's head; wherein the camera is located more than 10 mm away from the user's head; and (iii) a head-mounted computer configured to efficiently extract iPPG signals from the images based on focusing the iPPG calculations around pulse timings extracted from the PPG signal.

In one embodiment, a head-mounted iPPG system includes: (i) a head-mounted contact PPG device configured to measure a signal indicative of PPG signal at a first region comprising exposed skin on a user's head, (ii) a head-mounted camera configured to capture images of a second region comprising exposed skin on the user's head; wherein the camera is located more than 10 mm away from the user's head; and (iii) a head-mounted computer configured to: identify times at which fiducial points appear in the PPG signal; calculate, based on the times, time-segments in which the fiducial points are expected to appear in iPPG signals recognizable the images; and detect a physiological response based on values of the iPPG signals during the time-segments.

The following is description of additional aspects of embodiments of systems configured to detect physiological responses, including embodiments for various systems that may detect physiological responses based on thermal measurements and/or other sources of data.

A "thermal camera" refers herein to a non-contact device that measures electromagnetic radiation having wavelengths longer than 2500 nanometer (nm) and does not touch its region of interest (ROI). A thermal camera may include one sensing element (pixel), or multiple sensing elements that are also referred to herein as "sensing pixels", "pixels", and/or focal-plane array (FPA). A thermal camera may be based on an uncooled thermal sensor, such as a thermopile sensor, a microbolometer sensor (where microbolometer refers to any type of a bolometer sensor and its equivalents), a pyroelectric sensor, or a ferroelectric sensor.

Sentences in the form of "thermal measurements of an ROI" (usually denoted $TH_{ROI}$ or some variant thereof) refer to at least one of: (i) temperature measurements of the ROI ($T_{ROI}$), such as when using thermopile or microbolometer sensors, and (ii) temperature change measurements of the ROI ($\Delta T_{ROI}$), such as when using a pyroelectric sensor or when deriving the temperature changes from temperature measurements taken at different times by a thermopile sensor or a microbolometer sensor.

In some embodiments, a device, such as a thermal camera, may be positioned such that it occludes an ROI on the user's face, while in other embodiments, the device may be positioned such that it does not occlude the ROI. Sentences in the form of "the system/camera does not occlude the ROI" indicate that the ROI can be observed by a third person located in front of the user and looking at the ROI, such as illustrated by all the ROIs in FIG. 9 and FIG. 13. Sentences in the form of "the system/camera occludes the ROI" indicate that some of the ROIs cannot be observed directly by that third person, such as ROIs 19 and 37 that are occluded by the lenses in FIG. 3a, and ROIs 97 and 102 that are occluded by cameras 91 and 96, respectively, in FIG. 11.

Although many of the disclosed embodiments can use occluding thermal cameras successfully, in certain scenarios, such as when using an HMS on a daily basis and/or in a normal day-to-day setting, using thermal cameras that do not occlude their ROIs on the face may provide one or more advantages to the user, to the HMS, and/or to the thermal cameras, which may relate to one or more of the following: esthetics, better ventilation of the face, reduced weight, simplicity to wear, and reduced likelihood to being tarnished.

A "Visible-light camera" refers to a non-contact device designed to detect at least some of the visible spectrum, such as a camera with optical lenses and CMOS or CCD sensor.

The term "inward-facing head-mounted camera" refers to a camera configured to be worn on a user's head and to remain pointed at its ROI, which is on the user's face, also when the user's head makes angular and lateral movements (such as movements with an angular velocity above 0.1 rad/sec, above 0.5 rad/sec, and/or above 1 rad/sec). A head-mounted camera (which may be inward-facing and/or outward-facing) may be physically coupled to a frame worn on the user's head, may be attached to eyeglass using a clip-on mechanism (configured to be attached to and detached from the eyeglasses), or may be mounted to the user's head using any other known device that keeps the camera in a fixed position relative to the user's head also when the head moves. Sentences in the form of "camera physically coupled to the frame" mean that the camera moves with the frame, such as when the camera is fixed to (or integrated into) the frame, or when the camera is fixed to (or integrated into) an element that is physically coupled to the frame. The abbreviation "CAM" denotes "inward-facing head-mounted thermal camera", the abbreviation "$CAM_{out}$" denotes "outward-facing head-mounted thermal camera", the abbreviation "VCAM" denotes "inward-facing head-mounted visible-light camera", and the abbreviation "$VCAM_{out}$" denotes "outward-facing head-mounted visible-light camera".

Sentences in the form of "a frame configured to be worn on a user's head" or "a frame worn on a user's head" refer to a mechanical structure that loads more than 50% of its weight on the user's head. For example, an eyeglasses frame may include two temples connected to two rims connected by a bridge; the frame in Oculus Rift™ includes the foam placed on the user's face and the straps; and the frames in Google Glass™ and Spectacles by Snap Inc. are similar to eyeglasses frames. Additionally or alternatively, the frame may connect to, be affixed within, and/or be integrated with, a helmet (e.g., sports, motorcycle, bicycle, and/or combat helmets) and/or a brainwave-measuring headset.

When a thermal camera is inward-facing and head-mounted, challenges faced by systems known in the art that are used to acquire thermal measurements, which include non-head-mounted thermal cameras, may be simplified and even eliminated with some of the embodiments described herein. Some of these challenges may involve dealing with complications caused by movements of the user, image registration, ROI alignment, tracking based on hot spots or markers, and motion compensation in the IR domain.

In various embodiments, cameras are located close to a user's face, such as at most 2 cm, 5 cm, 10 cm, 15 cm, or 20 cm from the face (herein "cm" denotes to centimeters). The distance from the face/head in sentences such as "a camera located less than 15 cm from the face/head" refers to the shortest possible distance between the camera and the face/head. The head-mounted cameras used in various embodiments may be lightweight, such that each camera weighs below 10 g, 5 g, 1 g, and/or 0.5 g (herein "g" denotes to grams).

Figure 3A:
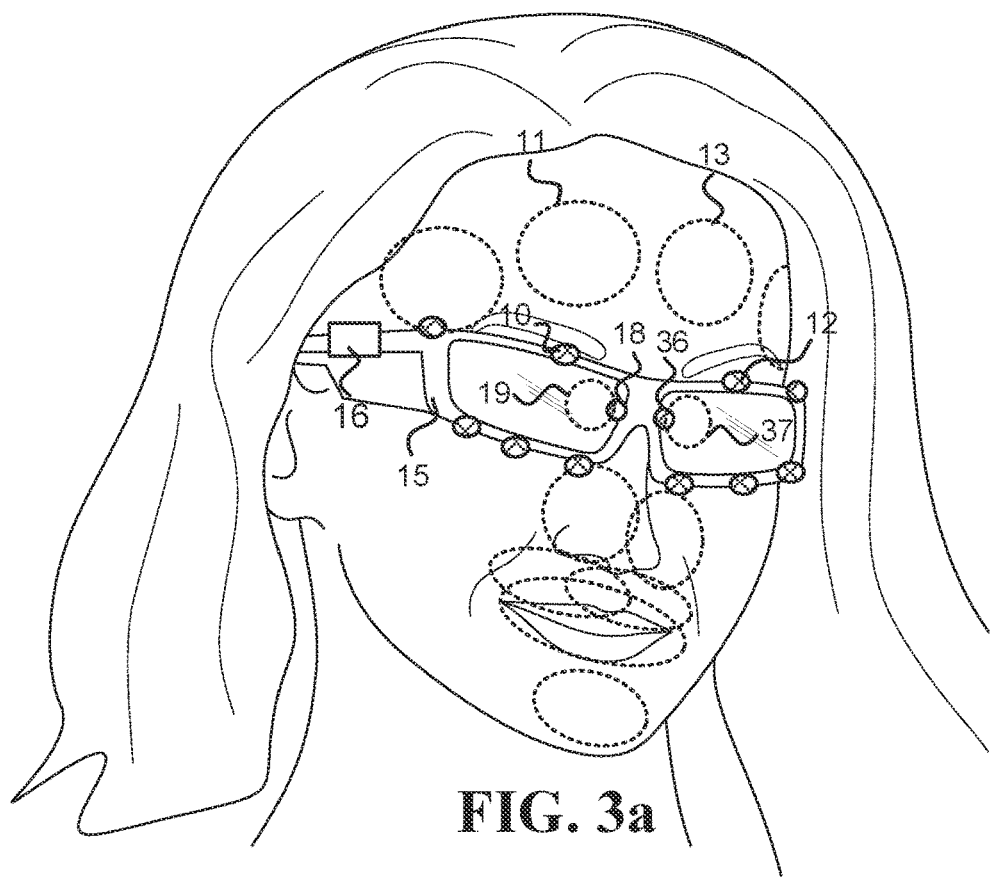
FIG. 3a and FIG. 3b illustrate various inward-facing head-mounted cameras coupled to an eyeglasses frame.
Figure 3B:
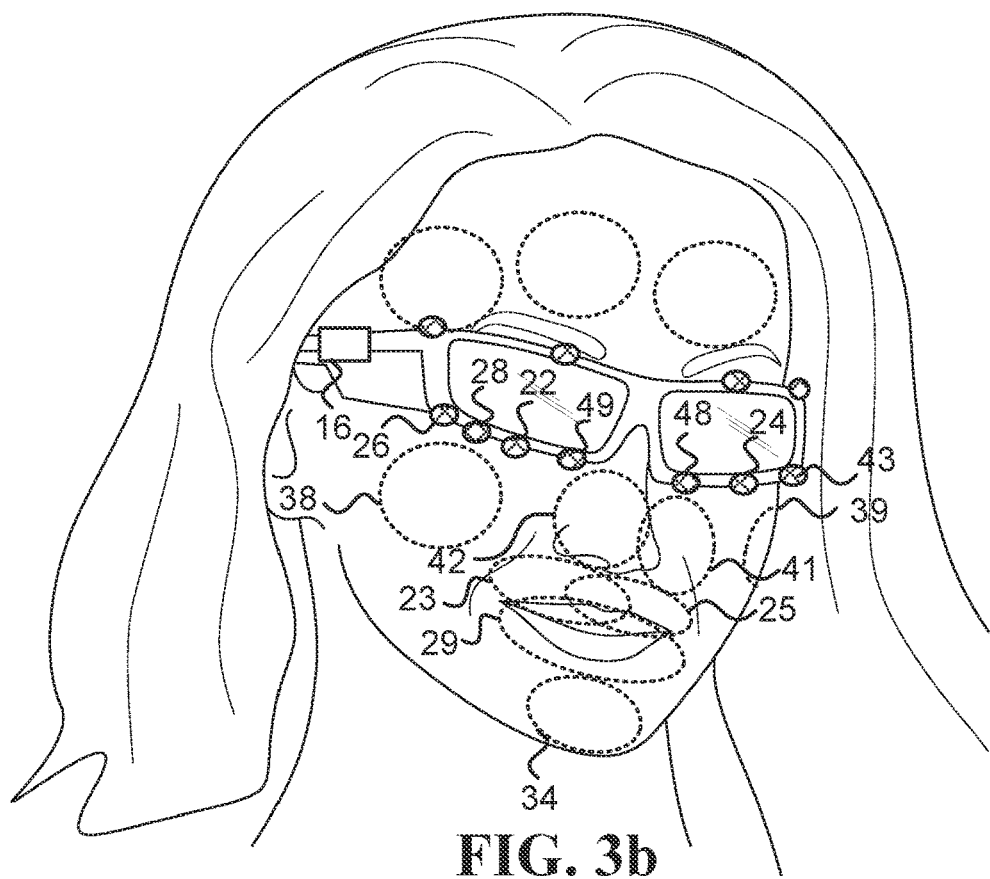

The following figures show various examples of HMSs equipped with head-mounted cameras. FIG. 3a illustrates various inward-facing head-mounted cameras coupled to an eyeglasses frame 15. Cameras 10 and 12 measure regions 11 and 13 on the forehead, respectively. Cameras 18 and 36 measure regions on the periorbital areas 19 and 37, respectively. The HMS further includes an optional computer 16, which may include a processor, memory, a battery and/or a communication module. FIG. 3b illustrates a similar HMS in which inward-facing head-mounted cameras 48 and 49 measure regions 41 and 41, respectively. Cameras 22 and 24 measure regions 23 and 25, respectively. Camera 28 measures region 29. And cameras 26 and 43 measure regions 38 and 39, respectively.

Figure 4:
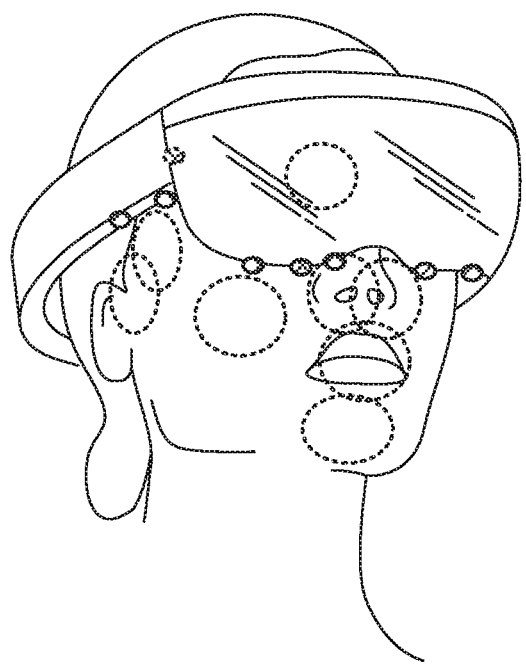
FIG. 4 illustrates inward-facing head-mounted cameras coupled to an augmented reality device.
Figure 5:
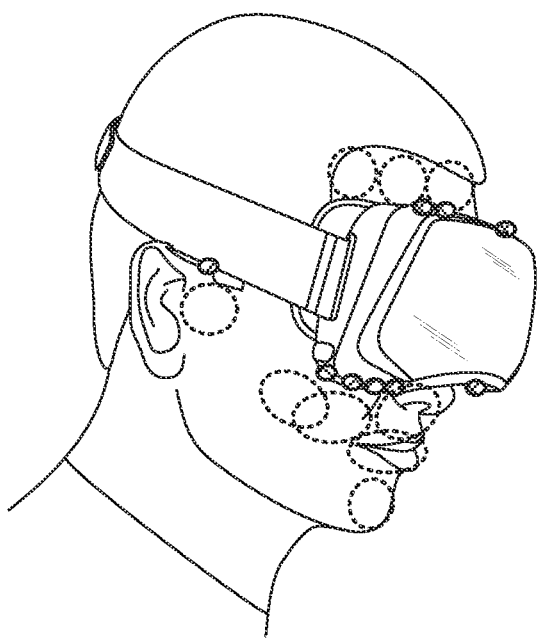
FIG. 5 illustrates head-mounted cameras coupled to a virtual reality device.
Figure 6:
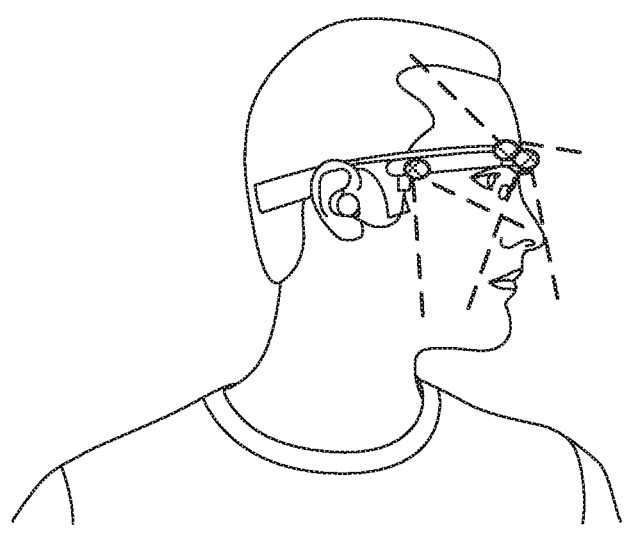
FIG. 6 illustrates a side view of head-mounted cameras coupled to an augmented reality device.
Figure 7:
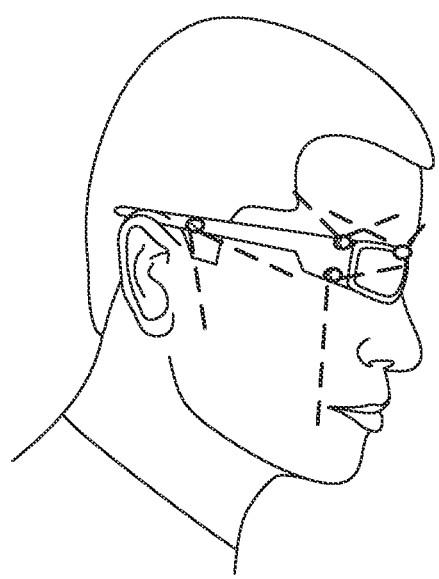
FIG. 7 illustrates a side view of head-mounted cameras coupled to a sunglasses frame.

FIG. 4 illustrates inward-facing head-mounted cameras coupled to an augmented reality device such as Microsoft HoloLens™. FIG. 5 illustrates head-mounted cameras coupled to a virtual reality device such as Facebook's Oculus Rift™. FIG. 6 is a side view illustration of head-mounted cameras coupled to an augmented reality device such as Google Glass™. FIG. 7 is another side view illustration of head-mounted cameras coupled to a sunglasses frame.

Figure 8:
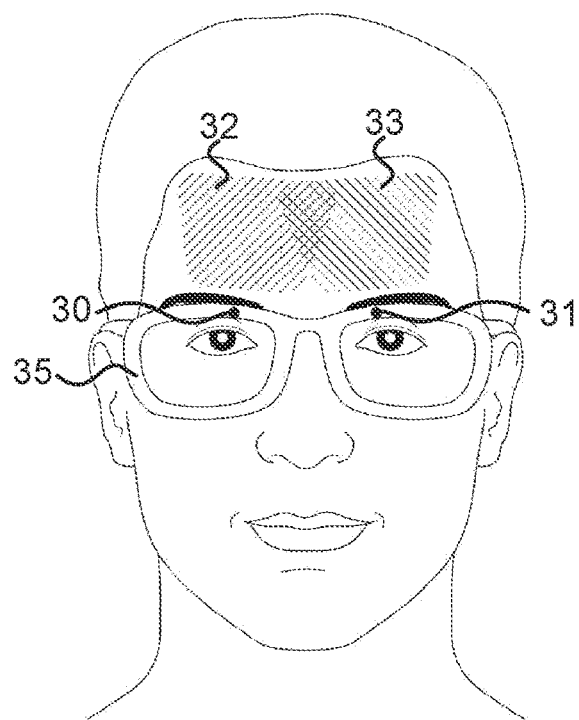
FIG. 8, FIG. 9, FIG. 10 and FIG. 11 illustrate head-mounted systems (HMSs) configured to measure various ROIs relevant to some of the embodiments describes herein.
Figure 9:
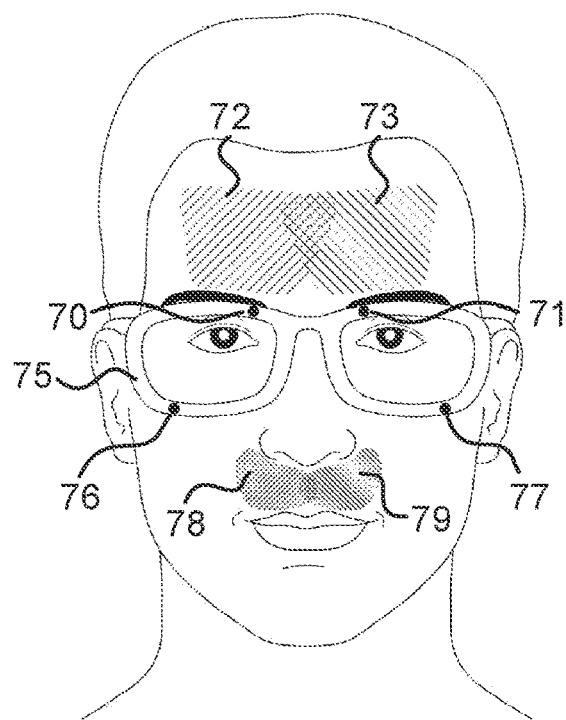
Figure 10:
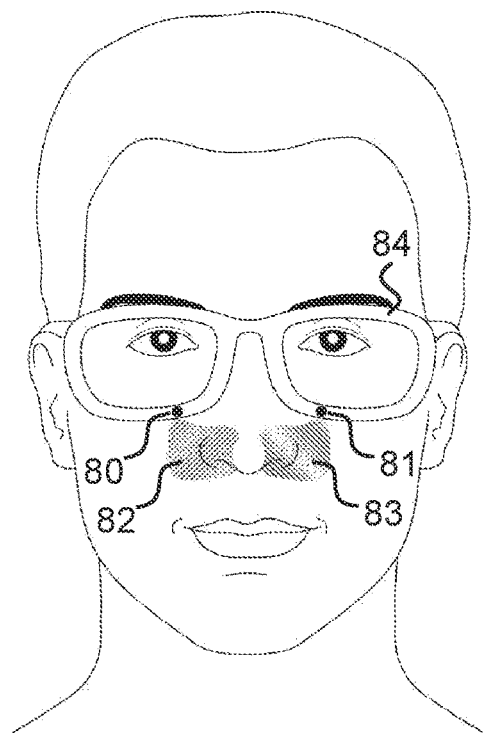
Figure 11:
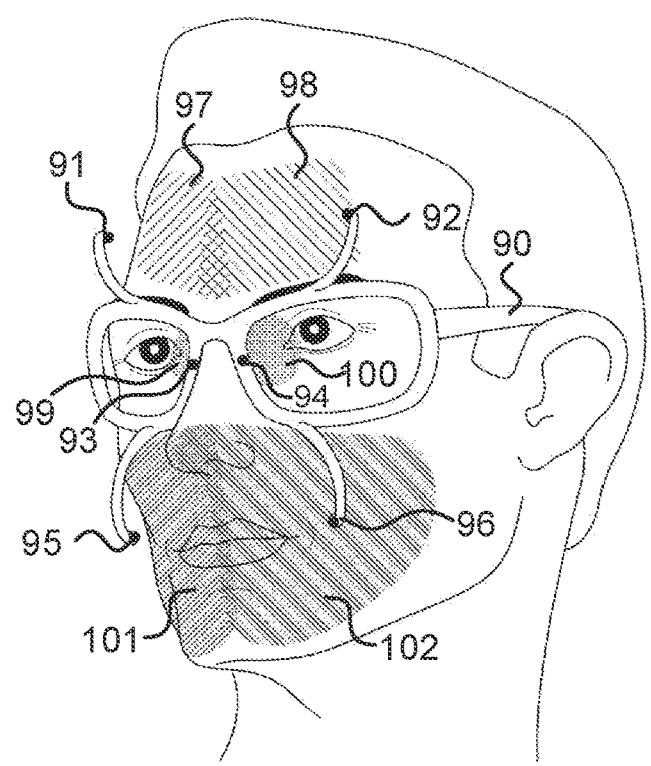

FIG. 8 to FIG. 11 illustrate HMSs configured to measure various ROIs relevant to some of the embodiments describes herein. FIG. 8 illustrates a frame 35 that mounts inward-facing head-mounted cameras 30 and 31 that measure regions 32 and 33 on the forehead, respectively. FIG. 9 illustrates a frame 75 that mounts inward-facing head-mounted cameras 70 and 71 that measure regions 72 and 73 on the forehead, respectively, and inward-facing head-mounted cameras 76 and 77 that measure regions 78 and 79 on the upper lip, respectively. FIG. 10 illustrates a frame 84 that mounts inward-facing head-mounted cameras 80 and 81 that measure regions 82 and 83 on the sides of the nose, respectively. And FIG. 11 illustrates a frame 90 that includes (i) inward-facing head-mounted cameras 91 and 92 that are mounted to protruding arms and measure regions 97 and 98 on the forehead, respectively, (ii) inward-facing head-mounted cameras 95 and 96, which are also mounted to protruding arms, which measure regions 101 and 102 on the lower part of the face, respectively, and (iii) head-mounted cameras 93 and 94 that measure regions on the periorbital areas 99 and 100, respectively.

Figure 12:
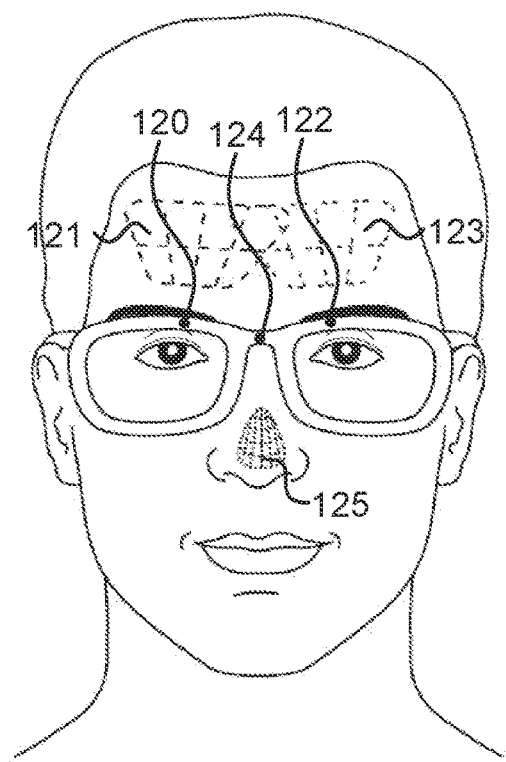
FIG. 12, FIG. 13, FIG. 14 and FIG. 15 illustrate various embodiments of systems that include inward-facing head-mounted cameras having multi-pixel sensors (FPA sensors)
Figure 13:
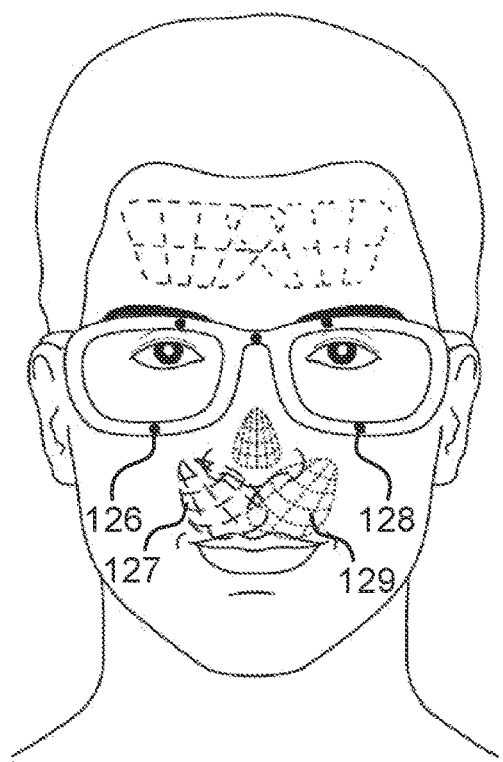
Figure 14:
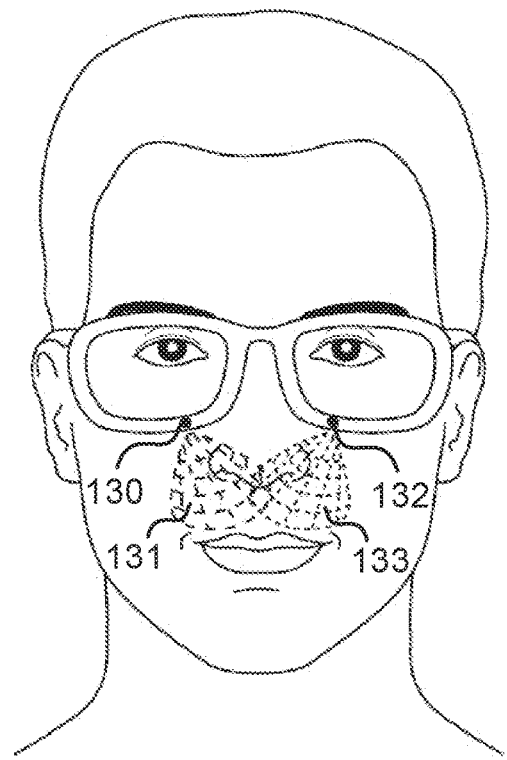
Figure 15:
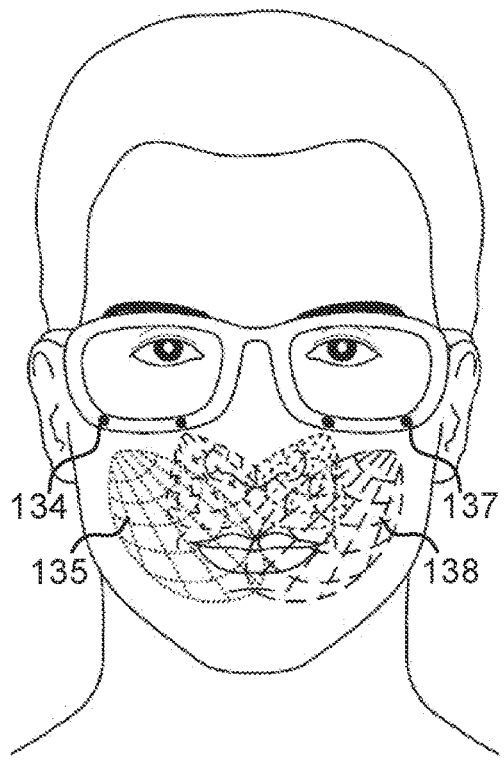

FIG. 12 to FIG. 15 illustrate various inward-facing head-mounted cameras having multi-pixel sensors (FPA sensors), configured to measure various ROIs relevant to some of the embodiments describes herein. FIG. 12 illustrates head-mounted cameras 120 and 122 that measure regions 121 and 123 on the forehead, respectively, and mounts head-mounted camera 124 that measure region 125 on the nose. FIG. 13 illustrates head-mounted cameras 126 and 128 that measure regions 127 and 129 on the upper lip, respectively, in addition to the head-mounted cameras already described in FIG. 12. FIG. 14 illustrates head-mounted cameras 130 and 132 that measure larger regions 131 and 133 on the upper lip and the sides of the nose, respectively. And FIG. 15 illustrates head-mounted cameras 134 and 137 that measure regions 135 and 138 on the right and left cheeks and right and left sides of the mouth, respectively, in addition to the head-mounted cameras already described in FIG. 14.

In some embodiments, the head-mounted cameras may be physically coupled to the frame using a clip-on device configured to be attached/detached from a pair of eyeglasses in order to secure/release the device to/from the eyeglasses, multiple times. The clip-on device holds at least an inward-facing camera, a processor, a battery, and a wireless communication module. Most of the clip-on device may be located in front of the frame (as illustrated in FIG. 16b, FIG. 17b, and FIG. 20), or alternatively, most of the clip-on device may be located behind the frame, as illustrated in FIG. 18b and FIG. 19b.

Figure 16A:
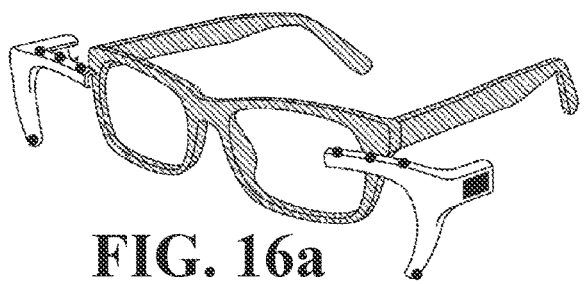
FIG. 16a, FIG. 16b, and FIG. 16c illustrate embodiments of two right and left clip-on devices that are configured to attached/detached from an eyeglasses frame.
Figure 16C:
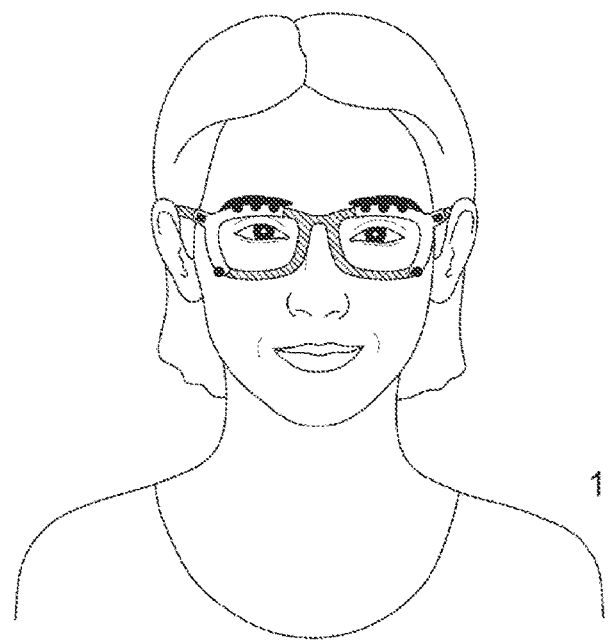
Figure 16B:
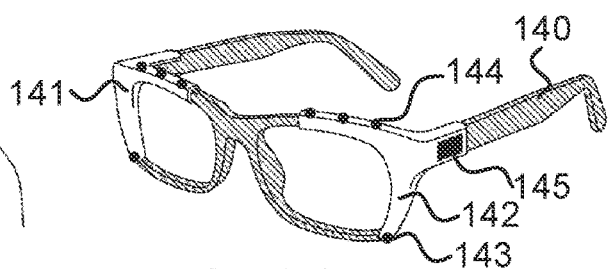

FIG. 16a, FIG. 16b, and FIG. 16c illustrate two right and left clip-on devices 141 and 142, respectively, configured to attached/detached from an eyeglasses frame 140. The clip-on device 142 includes an inward-facing head-mounted camera 143 pointed at a region on the lower part of the face (such as the upper lip, mouth, nose, and/or cheek), an inward-facing head-mounted camera 144 pointed at the forehead, and other electronics 145 (such as a processor, a battery, and/or a wireless communication module). The clip-on devices 141 and 142 may include additional cameras illustrated in the drawings as black circles.

Figure 17A:
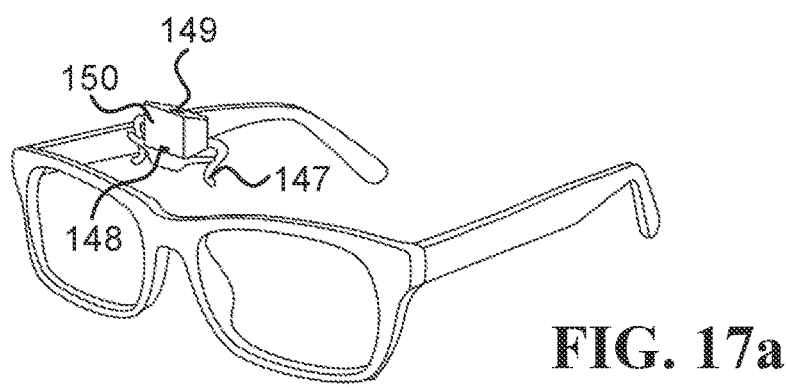
FIG. 17a and FIG. 17b illustrate an embodiment of a clip-on device that includes inward-facing head-mounted cameras pointed at the lower part of the face and the forehead.
Figure 17B:
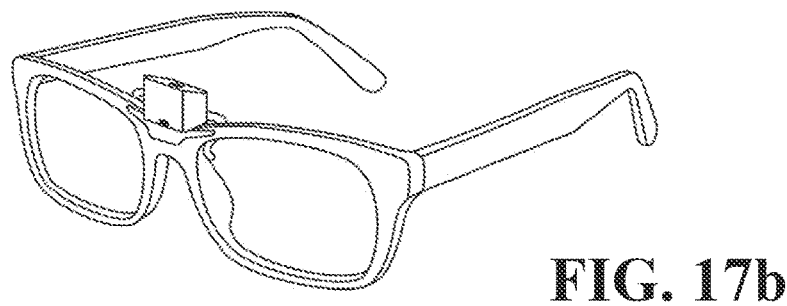

FIG. 17a and FIG. 17b illustrate a clip-on device 147 that includes an inward-facing head-mounted camera 148 pointed at a region on the lower part of the face (such as the nose), and an inward-facing head-mounted camera 149 pointed at the forehead. The other electronics (such as a processor, a battery, and/or a wireless communication module) is located inside the box 150, which also holds the cameras 148 and 149.

Figure 18A:
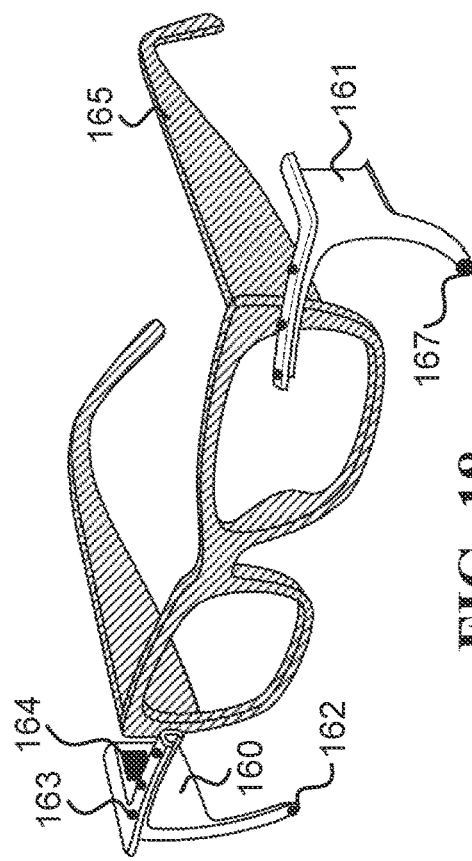
FIG. 18a and FIG. 18b illustrate embodiments of right and left clip-on devices that are configured to be attached behind an eyeglasses frame.
Figure 18B:
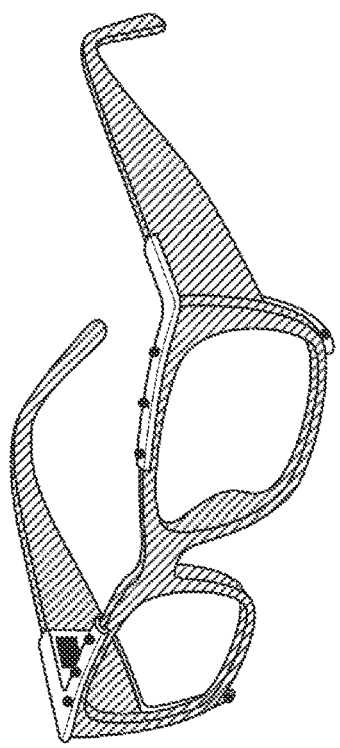

FIG. 18a and FIG. 18b illustrate two right and left clip-on devices 160 and 161, respectively, configured to be attached behind an eyeglasses frame 165. The clip-on device 160 includes an inward-facing head-mounted camera 162 pointed at a region on the lower part of the face (such as the upper lip, mouth, nose, and/or cheek), an inward-facing head-mounted camera 163 pointed at the forehead, and other electronics 164 (such as a processor, a battery, and/or a wireless communication module). The clip-on devices 160 and 161 may include additional cameras illustrated in the drawings as black circles.

Figure 19A:
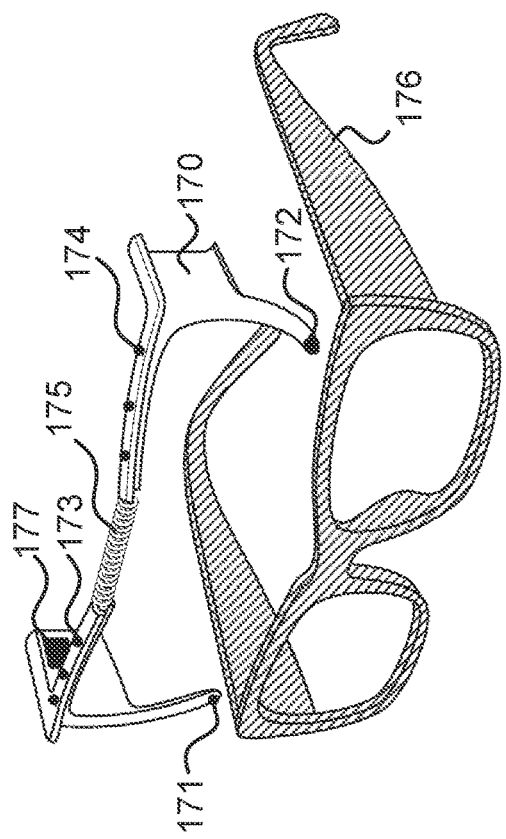
FIG. 19a and FIG. 19b illustrate an embodiment of a single-unit clip-on device that is configured to be attached behind an eyeglasses frame.
Figure 19B:
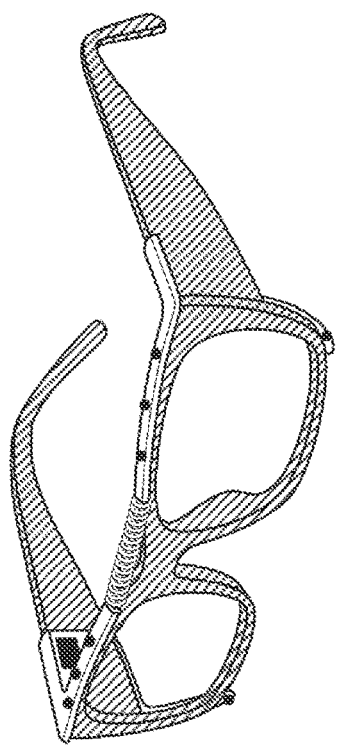
Figure 20:
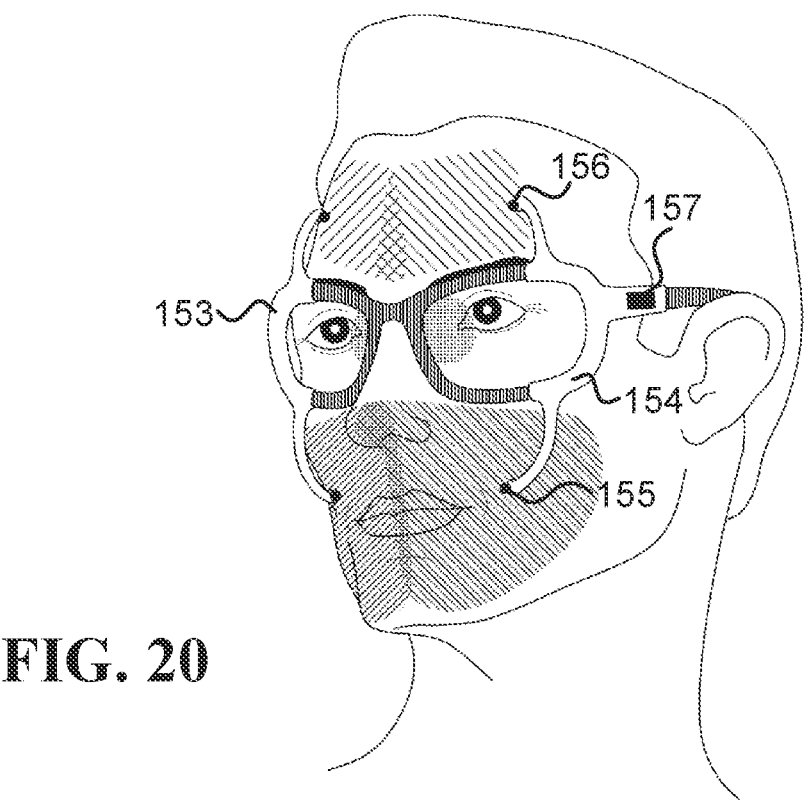
FIG. 20 illustrates embodiments of right and left clip-on devices, which are configured to be attached/detached from an eyeglasses frame, and have protruding arms to hold inward-facing head-mounted cameras.

FIG. 19a and FIG. 19b illustrate a single-unit clip-on device 170, configured to be attached behind an eyeglasses frame 176. The single-unit clip-on device 170 includes inward-facing head-mounted cameras 171 and 172 pointed at regions on the lower part of the face (such as the upper lip, mouth, nose, and/or cheek), inward-facing head-mounted cameras 173 and 174 pointed at the forehead, a spring 175 configured to apply force that holds the clip-on device 170 to the frame 176, and other electronics 177 (such as a processor, a battery, and/or a wireless communication module). The clip-on device 170 may include additional cameras illustrated in the drawings as black circles.

FIG. 20 illustrates two right and left clip-on devices 153 and 154, respectively, configured to attached/detached from an eyeglasses frame, and having protruding arms to hold the inward-facing head-mounted cameras. Head-mounted camera 155 measures a region on the lower part of the face, head-mounted camera 156 measures regions on the forehead, and the left clip-on device 154 further includes other electronics 157 (such as a processor, a battery, and/or a wireless communication module). The clip-on devices 153 and 154 may include additional cameras illustrated in the drawings as black circles.

It is noted that the elliptic and other shapes of the ROIs in some of the drawings are just for illustration purposes, and the actual shapes of the ROIs are usually not as illustrated. It is possible to calculate the accurate shape of an ROI using various methods, such as a computerized simulation using a 3D model of the face and a model of a head-mounted system (HMS) to which a thermal camera is physically coupled, or by placing a LED instead of the sensor (while maintaining the same field of view) and observing the illumination pattern on the face. Furthermore, illustrations and discussions of a camera represent one or more cameras, where each camera may have the same FOV and/or different FOVs. Unless indicated to the contrary, the cameras may include one or more sensing elements (pixels), even when multiple sensing elements do not explicitly appear in the figures; when a camera includes multiple sensing elements then the illustrated ROI usually refers to the total ROI captured by the camera, which is made of multiple regions that are respectively captured by the different sensing elements. The positions of the cameras in the figures are just for illustration, and the cameras may be placed at other positions on the HMS.

Sentences in the form of an "ROI on an area", such as ROI on the forehead or an ROI on the nose, refer to at least a portion of the area. Depending on the context, and especially when using a CAM having just one pixel or a small number of pixels, the ROI may cover another area (in addition to the area). For example, a sentence in the form of "an ROI on the nose" may refer to either: 100% of the ROI is on the nose, or some of the ROI is on the nose and some of the ROI is on the upper lip.

Various embodiments described herein involve detections of physiological responses based on user measurements. Some examples of physiological responses include stress, an allergic reaction, an asthma attack, a stroke, dehydration, intoxication, or a headache (which includes a migraine). Other examples of physiological responses include manifestations of fear, startle, sexual arousal, anxiety, joy, pain or guilt. Still other examples of physiological responses include physiological signals such as a heart rate or a value of a respiratory parameter of the user. Optionally, detecting a physiological response may involve one or more of the following: determining whether the user has/had the physiological response, identifying an imminent attack associated with the physiological response, and/or calculating the extent of the physiological response.

In some embodiments, detection of the physiological response is done by processing thermal measurements that fall within a certain window of time that characterizes the physiological response. For example, depending on the physiological response, the window may be five seconds long, thirty seconds long, two minutes long, five minutes long, fifteen minutes long, or one hour long. Detecting the physiological response may involve analysis of thermal measurements taken during multiple of the above-described windows, such as measurements taken during different days. In some embodiments, a computer may receive a stream of thermal measurements, taken while the user wears an HMS with coupled thermal cameras during the day, and periodically evaluate measurements that fall within a sliding window of a certain size.

In some embodiments, models are generated based on measurements taken over long periods. Sentences of the form of "measurements taken during different days" or "measurements taken over more than a week" are not limited to continuous measurements spanning the different days or over the week, respectively. For example, "measurements taken over more than a week" may be taken by eyeglasses equipped with thermal cameras, which are worn for more than a week, 8 hours a day. In this example, the user is not required to wear the eyeglasses while sleeping in order to take measurements over more than a week. Similarly, sentences of the form of "measurements taken over more than 5 days, at least 2 hours a day" refer to a set comprising at least 10 measurements taken over 5 different days, where at least two measurements are taken each day at times separated by at least two hours.

Utilizing measurements taken of a long period (e.g., measurements taken on "different days") may have an advantage, in some embodiments, of contributing to the generalizability of a trained model. Measurements taken over the long period likely include measurements taken in different environments and/or measurements taken while the measured user was in various physiological and/or mental states (e.g., before/after meals and/or while the measured user was sleepy/energetic/happy/depressed, etc.). Training a model on such data can improve the performance of systems that utilize the model in the diverse settings often encountered in real-world use (as opposed to controlled laboratory-like settings). Additionally, taking the measurements over the long period may have the advantage of enabling collection of a large amount of training data that is required for some machine learning approaches (e.g., "deep learning").

Detecting the physiological response may involve performing various types of calculations by a computer. Optionally, detecting the physiological response may involve performing one or more of the following operations: comparing thermal measurements to a threshold (when the threshold is reached that may be indicative of an occurrence of the physiological response), comparing thermal measurements to a reference time series, and/or by performing calculations that involve a model trained using machine learning methods. Optionally, the thermal measurements upon which the one or more operations are performed are taken during a window of time of a certain length, which may optionally depend on the type of physiological response being detected. In one example, the window may be shorter than one or more of the following durations: five seconds, fifteen seconds, one minute, five minutes, thirty minute, one hour, four hours, one day, or one week. In another example, the window may be longer than one or more of the aforementioned durations. Thus, when measurements are taken over a long period, such as measurements taken over a period of more than a week, detection of the physiological response at a certain time may be done based on a subset of the measurements that falls within a certain window near the certain time; the detection at the certain time does not necessarily involve utilizing all values collected throughout the long period.

In some embodiments, detecting the physiological response of a user may involve utilizing baseline thermal measurement values, most of which were taken when the user was not experiencing the physiological response. Optionally, detecting the physiological response may rely on observing a change to typical temperatures at one or more ROIs (the baseline), where different users might have different typical temperatures at the ROIs (i.e., different baselines). Optionally, detecting the physiological response may rely on observing a change to a baseline level, which is determined based on previous measurements taken during the preceding minutes and/or hours.

In some embodiments, detecting a physiological response involves determining the extent of the physiological response, which may be expressed in various ways that are indicative of the extent of the physiological response, such as: (i) a binary value indicative of whether the user experienced, and/or is experiencing, the physiological response, (ii) a numerical value indicative of the magnitude of the physiological response, (iii) a categorial value indicative of the severity/extent of the physiological response, (iv) an expected change in thermal measurements of an ROI (denoted $TH_{ROI}$ or some variation thereof), and/or (v) rate of change in $TH_{ROI}$. Optionally, when the physiological response corresponds to a physiological signal (e.g., a heart rate, a breathing rate, and an extent of frontal lobe brain activity), the extent of the physiological response may be interpreted as the value of the physiological signal.

One approach for detecting a physiological response, which may be utilized in some embodiments, involves comparing thermal measurements of one or more ROIs to a threshold. In these embodiments, the computer may detect the physiological response by comparing the thermal measurements, and/or values derived therefrom (e.g., a statistic of the measurements and/or a function of the measurements), to the threshold to determine whether it is reached. Optionally, the threshold may include a threshold in the time domain, a threshold in the frequency domain, an upper threshold, and/or a lower threshold. When a threshold involves a certain change to temperature, the certain change may be positive (increase in temperature) or negative (decrease in temperature). Different physiological responses described herein may involve different types of thresholds, which may be an upper threshold (where reaching the threshold means≥the threshold) or a lower threshold (where reaching the threshold means≤the threshold); for example, each physiological response may involve at least a certain degree of heating, or at least a certain degree cooling, at a certain ROI on the face.

Another approach for detecting a physiological response, which may be utilized in some embodiments, may be applicable when the thermal measurements of a user are treated as time series data. For example, the thermal measurements may include data indicative of temperatures at one or more ROIs at different points of time during a certain period. In some embodiments, the computer may compare thermal measurements (represented as a time series) to one or more reference time series that correspond to periods of time in which the physiological response occurred. Additionally or alternatively, the computer may compare the thermal measurements to other reference time series corresponding to times in which the physiological response did not occur. Optionally, if the similarity between the thermal measurements and a reference time series corresponding to a physiological response reaches a threshold, this is indicative of the fact that the thermal measurements correspond to a period of time during which the user had the physiological response. Optionally, if the similarity between the thermal measurements and a reference time series that does not correspond to a physiological response reaches another threshold, this is indicative of the fact that the thermal measurements correspond to a period of time in which the user did not have the physiological response. Time series analysis may involve various forms of processing involving segmenting data, aligning data, clustering, time warping, and various functions for determining similarity between sequences of time series data. Some of the techniques that may be utilized in various embodiments are described in Ding, Hui, et al. "Querying and mining of time series data: experimental comparison of representations and distance measures." Proceedings of the VLDB Endowment 1.2 (2008): 1542-1552, and in Wang, Xiaoyue, et al. "Experimental comparison of representation methods and distance measures for time series data." Data Mining and Knowledge Discovery 26.2 (2013): 275-309.

Herein, "machine learning" methods refers to learning from examples using one or more approaches. Optionally, the approaches may be considered supervised, semi-supervised, and/or unsupervised methods. Examples of machine learning approaches include: decision tree learning, association rule learning, regression models, nearest neighbors classifiers, artificial neural networks, deep learning, inductive logic programming, support vector machines, clustering, Bayesian networks, reinforcement learning, representation learning, similarity and metric learning, sparse dictionary learning, genetic algorithms, rule-based machine learning, and/or learning classifier systems.

Herein, a "machine learning-based model" is a model trained using machine learning methods. For brevity's sake, at times, a "machine learning-based model" may simply be called a "model". Referring to a model as being "machine learning-based" is intended to indicate that the model is trained using machine learning methods (otherwise, "model" may also refer to a model generated by methods other than machine learning).

In some embodiments, which involve utilizing a machine learning-based model, a computer is configured to detect the physiological response by generating feature values based on the thermal measurements (and possibly other values), and/or based on values derived therefrom (e.g., statistics of the measurements). The computer then utilizes the machine learning-based model to calculate, based on the feature values, a value that is indicative of whether, and/or to what extent, the user is experiencing (and/or is about to experience) the physiological response. Optionally, calculating said value is considered "detecting the physiological response". Optionally, the value calculated by the computer is indicative of the probability that the user has/had the physiological response.

Herein, feature values may be considered input to a computer that utilizes a model to perform the calculation of a value, such as the value indicative of the extent of the physiological response mentioned above. It is to be noted that the terms "feature" and "feature value" may be used interchangeably when the context of their use is clear. However, a "feature" typically refers to a certain type of value, and represents a property, while "feature value" is the value of the property with a certain instance (sample). For example, a feature may be temperature at a certain ROI, while the feature value corresponding to that feature may be 36.9° C. in one instance and 37.3° C. in another instance.

In some embodiments, a machine learning-based model used to detect a physiological response is trained based on data that includes samples. Each sample includes feature values and a label. The feature values may include various types of values. At least some of the feature values of a sample are generated based on measurements of a user taken during a certain period of time (e.g., thermal measurements taken during the certain period of time). Optionally, some of the feature values may be based on various other sources of information described herein. The label is indicative of a physiological response of the user corresponding to the certain period of time. Optionally, the label may be indicative of whether the physiological response occurred during the certain period and/or the extent of the physiological response during the certain period. Additionally or alternatively, the label may be indicative of how long the physiological response lasted. Labels of samples may be generated using various approaches, such as self-report by users, annotation by experts that analyze the training data, automatic annotation by a computer that analyzes the training data and/or analyzes additional data related to the training data, and/or utilizing additional sensors that provide data useful for generating the labels. It is to be noted that herein when it is stated that a model is trained based on certain measurements (e.g., "a model trained based on $TH_{ROI}$ taken on different days"), it means that the model was trained on samples comprising feature values generated based on the certain measurements and labels corresponding to the certain measurements. Optionally, a label corresponding to a measurement is indicative of the physiological response at the time the measurement was taken.

Various types of feature values may be generated based on thermal measurements. In one example, some feature values are indicative of temperatures at certain ROIs. In another example, other feature values may represent a temperature change at certain ROIs. The temperature changes may be with respect to a certain time and/or with respect to a different ROI. In order to better detect physiological responses that take some time to manifest, in some embodiments, some feature values may describe temperatures (or temperature changes) at a certain ROI at different points of time. Optionally, these feature values may include various functions and/or statistics of the thermal measurements such as minimum/maximum measurement values and/or average values during certain windows of time.

It is to be noted that when it is stated that feature values are generated based on data comprising multiple sources, it means that for each source, there is at least one feature value that is generated based on that source (and possibly other data). For example, stating that feature values are generated from thermal measurements of first and second ROIs ($TH_{ROI1}$ and $TH_{ROI2}$, respectively) means that the feature values may include a first feature value generated based on $TH_{ROI1}$ and a second feature value generated based on $TH_{ROI2}$. Optionally, a sample is considered generated based on measurements of a user (e.g., measurements comprising $TH_{ROI1}$ and $TH_{ROI2}$) when it includes feature values generated based on the measurements of the user.

In addition to feature values that are generated based on thermal measurements, in some embodiments, at least some feature values utilized by a computer (e.g., to detect a physiological response or train a mode) may be generated based on additional sources of data that may affect temperatures measured at various facial ROIs. Some examples of the additional sources include: (i) measurements of the environment such as temperature, humidity level, noise level, elevation, air quality, a wind speed, precipitation, and infrared radiation; (ii) contextual information such as the time of day (e.g., to account for effects of the circadian rhythm), day of month (e.g., to account for effects of the lunar rhythm), day in the year (e.g., to account for seasonal effects), and/or stage in a menstrual cycle; (iii) information about the user being measured such as sex, age, weight, height, and/or body build. Alternatively or additionally, at least some feature values may be generated based on physiological signals of the user obtained by sensors that are not thermal cameras, such as a visible-light camera, a photoplethysmogram (PPG) sensor, an electrocardiogram (ECG) sensor, an electroencephalography (EEG) sensor, a galvanic skin response (GSR) sensor, or a thermistor.

The machine learning-based model used to detect a physiological response may be trained, in some embodiments, based on data collected in day-to-day, real world scenarios. As such, the data may be collected at different times of the day, while users perform various activities, and in various environmental conditions. Utilizing such diverse training data may enable a trained model to be more resilient to the various effects different conditions can have on the values of thermal measurements, and consequently, be able to achieve better detection of the physiological response in real world day-to-day scenarios.

Since real world day-to-day conditions are not the same all the time, sometimes detection of the physiological response may be hampered by what is referred to herein as "confounding factors". A confounding factor can be a cause of warming and/or cooling of certain regions of the face, which is unrelated to a physiological response being detected, and as such, may reduce the accuracy of the detection of the physiological response. Some examples of confounding factors include: (i) environmental phenomena such as direct sunlight, air conditioning, and/or wind; (ii) things that are on the user's face, which are not typically there and/or do not characterize the faces of most users (e.g., cosmetics, ointments, sweat, hair, facial hair, skin blemishes, acne, inflammation, piercings, body paint, and food leftovers); (iii) physical activity that may affect the user's heart rate, blood circulation, and/or blood distribution (e.g., walking, running, jumping, and/or bending over); (iv) consumption of substances to which the body has a physiological response that may involve changes to temperatures at various facial ROIs, such as various medications, alcohol, caffeine, tobacco, and/or certain types of food; and/or (v) disruptive facial movements (e.g., frowning, talking, eating, drinking, sneezing, and coughing).

Occurrences of confounding factors may not always be easily identified in thermal measurements. Thus, in some embodiments, systems may incorporate measures designed to accommodate for the confounding factors. In some embodiments, these measures may involve generating feature values that are based on additional sensors, other than the thermal cameras. In some embodiments, these measures may involve refraining from detecting the physiological response, which should be interpreted as refraining from providing an indication that the user has the physiological response. For example, if an occurrence of a certain confounding factor is identified, such as strong directional sunlight that heats one side of the face, the system may refrain from detecting that the user had a stroke. In this example, the user may not be alerted even though a temperature difference between symmetric ROIs on both sides of the face reaches a threshold that, under other circumstances, would warrant alerting the user.

Training data used to train a model for detecting a physiological response may include, in some embodiments, a diverse set of samples corresponding to various conditions, some of which involve occurrence of confounding factors (when there is no physiological response and/or when there is a physiological response). Having samples in which a confounding factor occurs (e.g., the user is in direct sunlight or touches the face) can lead to a model that is less susceptible to wrongfully detect the physiological response (which may be considered an occurrence of a false positive) in real world situations.

When a model is trained with training data comprising samples generated from measurements of multiple users, the model may be considered a general model. When a model is trained with training data comprising at least a certain proportion of samples generated from measurements of a certain user, and/or when the samples generated from the measurements of the certain user are associated with at least a certain proportion of weight in the training data, the model may be considered a personalized model for the certain user. Optionally, the personalized model for the certain user provides better results for the certain user, compared to a general model that was not personalized for the certain user. Optionally, personalized model may be trained based on measurements of the certain user, which were taken while the certain user was in different situations; for example, train the model based on measurements taken while the certain user had a headache/epilepsy/stress/anger attack, and while the certain user did not have said attack. Additionally or alternatively, the personalized model may be trained based on measurements of the certain user, which were taken over a duration long enough to span different situations; examples of such long enough durations may include: a week, a month, six months, a year, and three years.

Training a model that is personalized for a certain user may require collecting a sufficient number of training samples that are generated based on measurements of the certain user. Thus, initially detecting the physiological response with the certain user may be done utilizing a general model, which may be replaced by a personalized model for the certain user, as a sufficiently large number of samples are generated based on measurements of the certain user. Another approach involves gradually modifying a general model based on samples of the certain user in order to obtain the personalized model.

After a model is trained, the model may be provided for use by a system that detects the physiological response. Providing the model may involve performing different operations. In one embodiment, providing the model to the system involves forwarding the model to the system via a computer network and/or a shared computer storage medium (e.g., writing the model to a memory that may be accessed by the system that detects the physiological response). In another embodiment, providing the model to the system involves storing the model in a location from which the system can retrieve the model, such as a database and/or cloud-based storage from which the system may retrieve the model. In still another embodiment, providing the model involves notifying the system regarding the existence of the model and/or regarding an update to the model. Optionally, this notification includes information needed in order for the system to obtain the model.

A model for detecting a physiological response may include different types of parameters. Following are some examples of various possibilities for the model and the type of calculations that may be accordingly performed by a computer in order to detect the physiological response: (a) the model comprises parameters of a decision tree. Optionally, the computer simulates a traversal along a path in the decision tree, determining which branches to take based on the feature values. A value indicative of the physiological response may be obtained at the leaf node and/or based on calculations involving values on nodes and/or edges along the path; (b) the model comprises parameters of a regression model (e.g., regression coefficients in a linear regression model or a logistic regression model). Optionally, the computer multiplies the feature values (which may be considered a regressor) with the parameters of the regression model in order to obtain the value indicative of the physiological response; and/or (c) the model comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer provides the feature values as inputs to the neural network, computes the values of the various activation functions and propagates values between layers, and obtains an output from the network, which is the value indicative of the physiological response.

A user interface (UI) may be utilized, in some embodiments, to notify the user and/or some other entity, such as a caregiver, about the physiological response and/or present an alert responsive to an indication that the extent of the physiological response reaches a threshold. The UI may include a screen to display the notification and/or alert, a speaker to play an audio notification, a tactile UI, and/or a vibrating UI. In some embodiments, "alerting" about a physiological response of a user refers to informing about one or more of the following: the occurrence of a physiological response that the user does not usually have (e.g., a stroke, intoxication, and/or dehydration), an imminent physiological response (e.g., an allergic reaction, an epilepsy attack, and/or a migraine), and an extent of the physiological response reaching a threshold (e.g., stress and/or anger reaching a predetermined level).

Various embodiments described herein involve an HMS that may be connected, using wires and/or wirelessly, with a device carried by the user and/or a non-wearable device. The HMS may include a battery, a computer, sensors, and a transceiver.

Figure 21A:
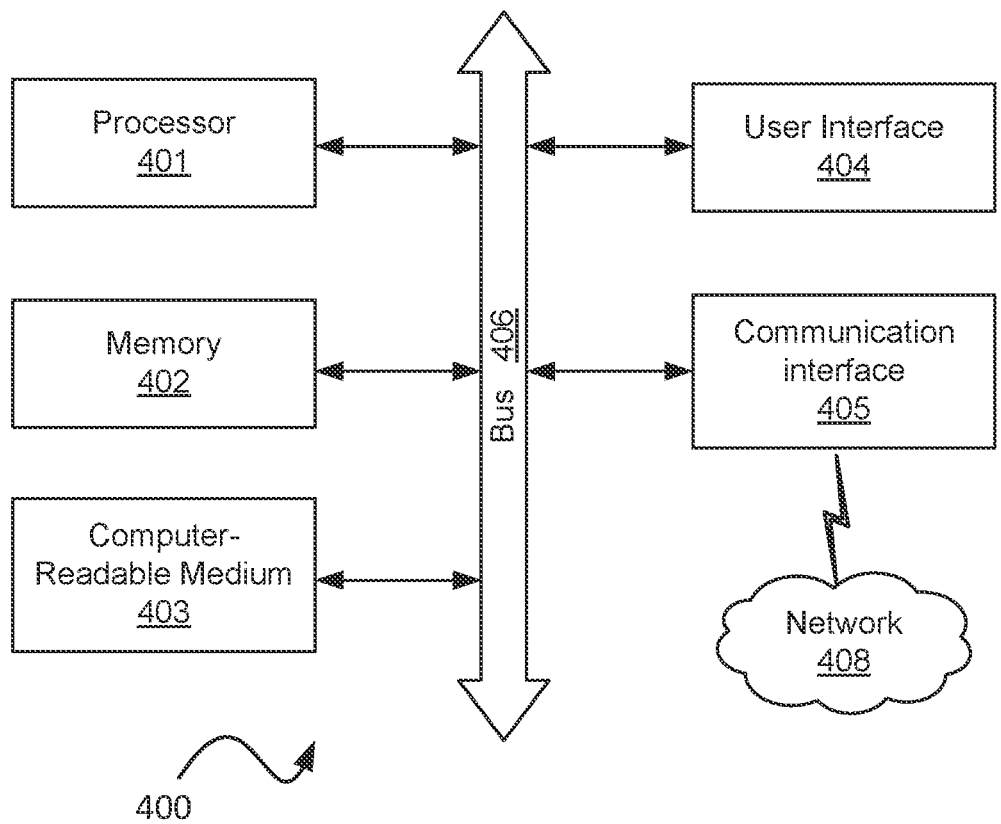
FIG. 21a and FIG. 21b are schematic illustrations of possible embodiments for computers.
Figure 21B:
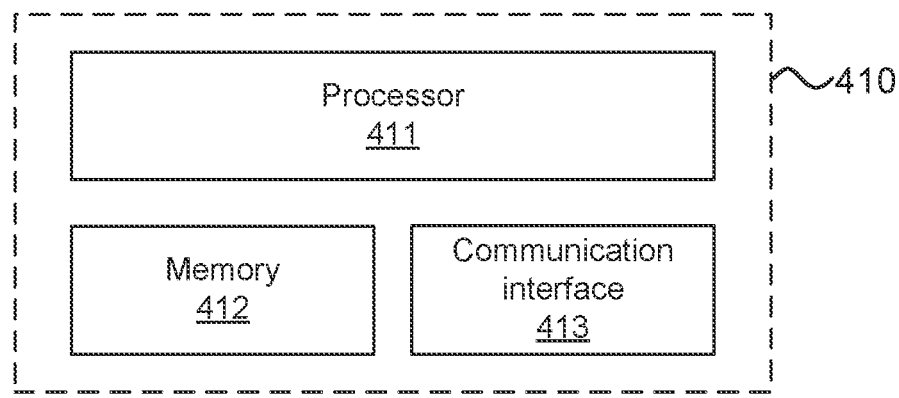

FIG. 21a and FIG. 21b are schematic illustrations of possible embodiments for computers (400, 410) that are able to realize one or more of the embodiments discussed herein that include a "computer". The computer (400, 410) may be implemented in various ways, such as, but not limited to, a microcontroller, a computer on a chip, a system-on-chip (SoC), a system-on-module (SoM), a processor with its required peripherals, a server computer, a client computer, a personal computer, a cloud computer, a network device, a handheld device (e.g., a smartphone), an head-mounted system (such as smartglasses, an augmented reality system, a virtual reality system, and/or a smart-helmet), a computing device embedded in a wearable device (e.g., a smartwatch or a computer embedded in clothing), a computing device implanted in the human body, and/or any other computer form capable of executing a set of computer instructions. Further, references to a computer or a processor include any collection of one or more computers and/or processors (which may be at different locations) that individually or jointly execute one or more sets of computer instructions. This means that the singular term "computer" is intended to imply one or more computers, which jointly perform the functions attributed to "the computer". In particular, some functions attributed to the computer may be performed by a computer on a wearable device (e.g., smartglasses) and/or a computer of the user (e.g., smartphone), while other functions may be performed on a remote computer, such as a cloud-based server.

The computer 400 includes one or more of the following components: processor 401, memory 402, computer readable medium 403, user interface 404, communication interface 405, and bus 406. The computer 410 includes one or more of the following components: processor 411, memory 412, and communication interface 413.

Thermal measurements that are forwarded to a processor/computer may include "raw" values that are essentially the same as the values measured by thermal cameras, and/or processed values that are the result of applying some form of preprocessing and/or analysis to the raw values. Examples of methods that may be used to process the raw values include analog signal processing, digital signal processing, and various forms of normalization, noise cancellation, and/or feature extraction.

Functionality of various embodiments may be implemented in hardware, software, firmware, or any combination thereof. If implemented at least in part in software, implementing the functionality may involve a computer program that includes one or more instructions or code stored or transmitted on a computer-readable medium and executed by one or more processors. Computer-readable media may include computer-readable storage media, which corresponds to a tangible medium such as data storage media, or communication media including any medium that facilitates transfer of a computer program from one place to another. Computer-readable medium may be any media that can be accessed by one or more computers to retrieve instructions, code, data, and/or data structures for implementation of the described embodiments. A computer program product may include a computer-readable medium. In one example, the computer-readable medium 403 may include one or more of the following: RAM, ROM, EEPROM, optical storage, magnetic storage, biologic storage, flash memory, or any other medium that can store computer readable data.

A computer program (also known as a program, software, software application, script, program code, or code) can be written in any form of programming language, including compiled or interpreted languages, declarative or procedural languages. The program can be deployed in any form, including as a standalone program or as a module, component, subroutine, object, or another unit suitable for use in a computing environment. A computer program may correspond to a file in a file system, may be stored in a portion of a file that holds other programs or data, and/or may be stored in one or more files that may be dedicated to the program. A computer program may be deployed to be executed on one or more computers that are located at one or more sites that may be interconnected by a communication network.

Computer-readable medium may include a single medium and/or multiple media (e.g., a centralized or distributed database, and/or associated caches and servers) that store one or more sets of instructions. In various embodiments, a computer program, and/or portions of a computer program, may be stored on a non-transitory computer-readable medium, and may be updated and/or downloaded via a communication network, such as the Internet. Optionally, the computer program may be downloaded from a central repository, such as Apple App Store and/or Google Play. Optionally, the computer program may be downloaded from a repository, such as an open source and/or community run repository (e.g., GitHub).

At least some of the methods described herein are "computer-implemented methods" that are implemented on a computer, such as the computer (400, 410), by executing instructions on the processor (401, 411). Additionally, at least some of these instructions may be stored on a non-transitory computer-readable medium.

Herein, a direction of the optical axis of a VCAM or a CAM that has focusing optics is determined by the focusing optics, while the direction of the optical axis of a CAM without focusing optics (such as a single pixel thermopile) is determined by the angle of maximum responsivity of its sensor. When optics are utilized to take measurements with a CAM, then the term CAM includes the optics (e.g., one or more lenses). In some embodiments, the optics of a CAM may include one or more lenses made of a material suitable for the required wavelength, such as one or more of the following materials: Calcium Fluoride, Gallium Arsenide, Germanium, Potassium Bromide, Sapphire, Silicon, Sodium Chloride, and Zinc Sulfide. In other embodiments, the CAM optics may include one or more diffractive optical elements, and/or or a combination of one or more diffractive optical elements and one or more refractive optical elements.

When CAM includes an optical limiter/field limiter/FOV limiter (such as a thermopile sensor inside a standard TO-39 package with a window, or a thermopile sensor with a polished metal field limiter), then the term CAM may also refer to the optical limiter. Depending on the context, the term CAM may also refer to a readout circuit adjacent to CAM, and/or to the housing that holds CAM.

Herein, references to thermal measurements in the context of calculating values based on thermal measurements, generating feature values based on thermal measurements, or comparison of thermal measurements, relate to the values of the thermal measurements (which are values of temperature or values of temperature changes). Thus, a sentence in the form of "calculating based on $TH_{ROI}$" may be interpreted as "calculating based on the values of $TH_{ROI}$", and a sentence in the form of "comparing $TH_{ROI1}$ and $TH_{ROI2}$" may be interpreted as "comparing values of $TH_{ROI1}$ and values of $TH_{ROI2}$".

Depending on the embodiment, thermal measurements of an ROI (usually denoted $TH_{ROI}$ or using a similar notation) may have various forms, such as time series, measurements taken according to a varying sampling frequency, and/or measurements taken at irregular intervals. In some embodiments, thermal measurements may include various statistics of the temperature measurements (T) and/or the changes to temperature measurements ($\Delta T$), such as minimum, maximum, and/or average values. Thermal measurements may be raw and/or processed values. When a thermal camera has multiple sensing elements (pixels), the thermal measurements may include values corresponding to each of the pixels, and/or include values representing processing of the values of the pixels. The thermal measurements may be normalized, such as normalized with respect to a baseline (which is based on earlier thermal measurements), time of day, day in the month, type of activity being conducted by the user, and/or various environmental parameters (e.g., the environment's temperature, humidity, radiation level, etc.).

As used herein, references to "one embodiment" (and its variations) mean that the feature being referred to may be included in at least one embodiment of the invention. Moreover, separate references to "one embodiment", "some embodiments", "another embodiment", "still another embodiment", etc., may refer to the same embodiment, may illustrate different aspects of an embodiment, and/or may refer to different embodiments.

Some embodiments may be described using the verb "indicating", the adjective "indicative", and/or using variations thereof. Herein, sentences in the form of "X is indicative of Y" mean that X includes information correlated with Y, up to the case where X equals Y. For example, sentences in the form of "thermal measurements indicative of a physiological response" mean that the thermal measurements include information from which it is possible to infer the physiological response. Stating that "X indicates Y" or "X indicating Y" may be interpreted as "X being indicative of Y". Additionally, sentences in the form of "provide/receive an indication indicating whether X happened" may refer herein to any indication method, including but not limited to: sending/receiving a signal when X happened and not sending/receiving a signal when X did not happen, not sending/receiving a signal when X happened and sending/receiving a signal when X did not happen, and/or sending/receiving a first signal when X happened and sending/receiving a second signal X did not happen.

Herein, "most" of something is defined as above 51% of the something (including 100% of the something). Both a "portion" of something and a "region" of something refer herein to a value between a fraction of the something and 100% of the something. For example, sentences in the form of a "portion of an area" may cover between 0.1% and 100% of the area. As another example, sentences in the form of a "region on the user's forehead" may cover between the smallest area captured by a single pixel (such as 0.1% or 5% of the forehead) and 100% of the forehead. The word "region" refers to an open-ended claim language, and a camera said to capture a specific region on the face may capture just a small part of the specific region, the entire specific region, and/or a portion of the specific region together with additional region(s).

Sentences in the form of "angle greater than 20°" refer to absolute values (which may be +20° or −20° in this example), unless specifically indicated, such as in a phrase having the form of "the optical axis of CAM is 20° above/below the Frankfort horizontal plane" where it is clearly indicated that the CAM is pointed upwards/downwards. The Frankfort horizontal plane is created by two lines from the superior aspects of the right/left external auditory canal to the most inferior point of the right/left orbital rims.

The terms "comprises," "comprising," "includes," "including," "has," "having", or any other variation thereof, indicate an open-ended claim language that does not exclude additional limitations. The "a" or "an" is employed to describe one or more, and the singular also includes the plural unless it is obvious that it is meant otherwise; for example, sentences in the form of "a CAM configured to take thermal measurements of a region ($TH_{ROI}$)" refers to one or more CAMs that take thermal measurements of one or more regions, including one CAM that takes thermal measurements of multiple regions; as another example, "a computer" refers to one or more computers, such as a combination of a wearable computer that operates together with a cloud computer.

The phrase "based on" is intended to mean "based, at least in part, on". Additionally, stating that a value is calculated "based on X" and following that, in a certain embodiment, that the value is calculated "also based on Y", means that in the certain embodiment, the value is calculated based on X and Y.

The terms "first", "second" and so forth are to be interpreted merely as ordinal designations, and shall not be limited in themselves. A predetermined value is a fixed value and/or a value determined any time before performing a calculation that compares a certain value with the predetermined value. A value is also considered to be a predetermined value when the logic, used to determine whether a threshold that utilizes the value is reached, is known before start performing computations to determine whether the threshold is reached.

The embodiments of the invention may include any variety of combinations and/or integrations of the features of the embodiments described herein. Although some embodiments may depict serial operations, the embodiments may perform certain operations in parallel and/or in different orders from those depicted. Moreover, the use of repeated reference numerals and/or letters in the text and/or drawings is for the purpose of simplicity and clarity and does not in itself dictate a relationship between the various embodiments and/or configurations discussed. The embodiments are not limited in their applications to the order of steps of the methods, or to details of implementation of the devices, set in the description, drawings, or examples. Moreover, individual blocks illustrated in the figures may be functional in nature and therefore may not necessarily correspond to discrete hardware elements.

Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination. Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the embodiments. Accordingly, this disclosure is intended to embrace all such alternatives, modifications, and variations that fall within the spirit and scope of the appended claims and their equivalents.

We claim:

1. A system configured to detect alcohol intoxication, comprising:

first and second inward-facing head-mounted cameras ($Cam_{1\&2}$), located less than 5 cm from a user's face, sensitive to wavelengths below 1050 nanometer, and configured to capture images of respective first and second regions on the user's face; wherein middles of the first and second regions are at least 4 cm apart; and a computer configured to:

calculate, based on baseline images captured with $Cam_{1\&2}$ while the user was not intoxicated, a baseline pattern comprising values indicative of first and second baseline hemoglobin concentrations at the first and second regions, respectively;

calculate, based on a current set of images captured with $Cam_{1\&2}$, a current pattern comprising values indicative of first and second current hemoglobin concentrations at the first and second regions, respectively; and detect whether the user is intoxicated based on a deviation of the current pattern from the baseline pattern.

2. The system of claim 1, wherein the computer is further configured to: calculate, based on additional baseline images captured with $Cam_{1\&2}$ while the user was intoxicated, an intoxication-baseline pattern comprising values indicative of first and second intoxication hemoglobin concentrations at the first and second regions, respectively; and base the detection of whether the user is intoxicated also on a deviation of the current pattern from the intoxication-baseline pattern.

3. The system of claim 1, wherein the first region is located above the user's eyes, and the second region is located below the user's eyes.

4. The system of claim 1, wherein the middle of the first region is located less than 4 cm from the vertical symmetric axis of the user's face, and the middle of the second region is located more than 4 cm from the vertical symmetric axis.

5. The system of claim 1, wherein the baseline images and the current set of images comprise a first channel corresponding to wavelengths that are mostly below 580 nanometers and a second channel corresponding to wavelengths mostly above 580 nanometers; the baseline pattern comprises: (i) first values, derived based on the first channel in the baseline images, which are indicative of the first and second baseline hemoglobin concentrations at the first and second regions, respectively, and (ii) second values, derived based on the second channel in the baseline images, which are indicative of third and fourth baseline hemoglobin concentrations at the first and second regions, respectively; the current pattern comprises: (i) third values, derived based on the first channel in the current set of images, which are indicative of the first and second current hemoglobin concentrations at the first and second regions, respectively, and (ii) fourth values, derived based on the second channel in the current set of images, which are indicative of third and fourth current hemoglobin concentrations at the first and second regions, respectively; whereby having separate values for different wavelengths enables to account for thermal interference from the environment when detecting whether the user is intoxicated because thermal interference from the environment is expected to affect the third values more than the fourth values.

6. The system of claim 1, wherein the computer is further configured to calculate the values indicative of the baseline and current hemoglobin concentrations based on detecting facial flushing patterns in the baseline and current images.

7. The system of claim 1, wherein the computer is further configured to calculate, based on the current set of images, a current heart rate and/or a current respiration rate of the user, and to detect whether the user is intoxicated based on the deviation of the current pattern from the baseline pattern and deviations of the current heart rate and/or the current respiration rate from a baseline heart rate and/or baseline respiration rate of the user, respectively.

8. The system of claim 1, further comprising a short-wave infrared (SWIR) inward-facing head-mounted camera configured to detect wavelengths in at least a portion of the range of 700 nm to 2500 nm; wherein the computer is further configured to utilize a deviation of a current SWIR pattern from a baseline SWIR pattern taken while the user was not intoxicated in the detection of whether the user is intoxicated.

9. The system of claim 1, wherein the computer is further configured to detect blushing based on the deviation of the current pattern from the baseline pattern, and present an alert to the user about the blushing.

10. The system of claim 1, wherein the computer is further configured to utilize one or more calibration measurements of the user's core body temperature, taken by a different device, prior to a certain time, to calculate the user's core body temperature based on a certain set of images that were taken by $Cam_{1\&2}$ after the certain time.

11. The system of claim 1, wherein the computer is further configured to calculate the user's core body temperature based on the deviation of the current pattern from the baseline pattern.

12. The system of claim 1, wherein the computer is further configured to calculate the values indicative of the baseline and current hemoglobin concentrations based on detecting imaging photoplethysmogram signals in the baseline and current images.

13. A method for detecting alcohol intoxication, comprising:
receiving, from first and second inward-facing head-mounted cameras ($Cam_{1\&2}$) sensitive to wavelengths below 1050 nanometer, images of respective first and second regions on a user's face; wherein middles of the first and second regions are at least 4 cm apart;
calculating, based on baseline images captured with $Cam_{1\&2}$ while the user was not intoxicated, a baseline pattern comprising values indicative of first and second baseline hemoglobin concentrations at the first and second regions, respectively;
calculating, based on a current set of images captured with $Cam_{1\&2}$, a current pattern comprising values indicative of first and second current hemoglobin concentrations at the first and second regions, respectively; and
detecting whether the user is intoxicated based on a deviation of the current pattern from the baseline pattern.

14. The method of claim 13, further comprising calculating, based on additional baseline images captured with $Cam_{1\&2}$ while the user was intoxicated, an intoxication-baseline pattern comprising values indicative of first and second intoxication hemoglobin concentrations at the first and second regions, respectively; and detecting whether the user is intoxicated also based on a deviation of the current pattern from the intoxication-baseline pattern.

15. The method of claim 13, wherein the baseline images and the current set of images comprise a first channel corresponding to wavelengths that are mostly below 580 nanometers and a second channel corresponding to wavelengths mostly above 580 nanometers; the baseline pattern comprises: (i) first values, derived based on the first channel in the baseline images, which are indicative of the first and second baseline hemoglobin concentrations at the first and second regions, respectively, and (ii) second values, derived based on the second channel in the baseline images, which are indicative of third and fourth baseline hemoglobin concentrations at the first and second regions, respectively; the current pattern comprises: (i) third values, derived based on the first channel in the current set of images, which are indicative of the first and second current hemoglobin concentrations at the first and second regions, respectively, and (ii) fourth values, derived based on the second channel in the current set of images, which are indicative of third and fourth current hemoglobin concentrations at the first and second regions, respectively.

16. The method of claim 13, further comprising: calculating, based on the current set of images, a current heart rate and/or a current respiration rate of the user, and detecting whether the user is intoxicated based on the deviation of the current pattern from the baseline pattern and deviations of the current heart rate and/or the current respiration rate from a baseline heart rate and/or baseline respiration rate of the user, respectively.

17. A non-transitory computer readable medium storing one or more computer programs configured to cause a processor-based system to execute steps comprising:
receiving, from first and second inward-facing head-mounted cameras ($Cam_{1\&2}$) sensitive to wavelengths below 1050 nanometer, images of respective first and second regions on a user's face; wherein middles of the first and second regions are at least 4 cm apart;
calculating, based on baseline images captured with $Cam_{1\&2}$ while the user was not intoxicated, a baseline pattern comprising values indicative of first and second baseline hemoglobin concentrations at the first and second regions, respectively;
calculating, based on a current set of images captured with $Cam_{1\&2}$, a current pattern comprising values indicative of first and second current hemoglobin concentrations at the first and second regions, respectively; and
detecting whether the user is intoxicated based on a deviation of the current pattern from the baseline pattern.

18. The non-transitory computer readable medium of claim 17, further comprising instructions for execution of the following steps: calculating, based on additional baseline images captured with $Cam_{1\&2}$ while the user was intoxicated, an intoxication-baseline pattern comprising values indicative of first and second intoxication hemoglobin concentrations at the first and second regions, respectively; and detecting whether the user is intoxicated also based on a deviation of the current pattern from the intoxication-baseline pattern.

19. The non-transitory computer readable medium of claim 17, further comprising instructions for execution of the following steps: calculating, based on the current set of images, a current heart rate and/or a current respiration rate of the user, and detecting whether the user is intoxicated also based on deviations of the current heart rate and/or the current respiration rate from a baseline heart rate and/or baseline respiration rate of the user, respectively.

20. The non-transitory computer readable medium of claim 17, further comprising instructions for execution of a step involving calculating the user's core body temperature based on the deviation of the current pattern from the baseline pattern, to detect fever.

* * * * *